United States Patent
Williams, III et al.

(10) Patent No.: US 12,280,088 B2
(45) Date of Patent: Apr. 22, 2025

(54) DRY POWDER FORMULATION OF CAVEOLIN-1 PEPTIDES AND METHODS OF USE THEREOF

(71) Applicants: BOARD OF REGENTS, THE UNIVERSITY OF TEXAS SYSTEM, Austin, TX (US); REIN THERAPEUTICS, INC., Austin, TX (US)

(72) Inventors: Robert O. Williams, III, Austin, TX (US); Alan B. Watts, Austin, TX (US); Yajie Zhang, Austin, TX (US); Sawittree Sahakijpijarn, Austin, TX (US); Dale Christensen, Austin, TX (US); John J. Koleng, Austin, TX (US)

(73) Assignees: BOARD OF REGENTS, THE UNIVERSITY OF TEXAS SYSTEM, Austin, TX (US); Rein Therapeutics, Inc., Austin, TX (US)

( * ) Notice: Subject to any disclaimer, the term of this patent is extended or adjusted under 35 U.S.C. 154(b) by 517 days.

(21) Appl. No.: 17/274,666

(22) PCT Filed: Sep. 10, 2019

(86) PCT No.: PCT/US2019/050349
§ 371 (c)(1),
(2) Date: Mar. 9, 2021

(87) PCT Pub. No.: WO2020/055824
PCT Pub. Date: Mar. 19, 2020

(65) Prior Publication Data
US 2021/0260150 A1  Aug. 26, 2021

Related U.S. Application Data

(60) Provisional application No. 62/729,010, filed on Sep. 10, 2018.

(51) Int. Cl.
| | | |
|---|---|---|
| *A61K 38/08* | (2019.01) | |
| *A61K 9/00* | (2006.01) | |
| *A61K 9/14* | (2006.01) | |
| *A61K 38/10* | (2006.01) | |
| *A61K 45/06* | (2006.01) | |
| *A61P 11/00* | (2006.01) | |
| *C07K 7/06* | (2006.01) | |
| *C07K 7/08* | (2006.01) | |

(52) U.S. Cl.
CPC .............. *A61K 38/08* (2013.01); *A61K 9/00* (2013.01); *A61K 9/0075* (2013.01); *A61K 9/14* (2013.01); *A61K 38/10* (2013.01); *A61K 45/06* (2013.01); *A61P 11/00* (2018.01); *C07K 7/06* (2013.01); *C07K 7/08* (2013.01); *C07K 2319/10* (2013.01)

(58) Field of Classification Search
CPC .... A61K 9/0073; A61K 38/08; A61K 38/177; A61K 9/0075; A61K 9/14; A61K 38/10; A61K 9/00; C07K 7/06; A61P 43/00; A61P 11/00
See application file for complete search history.

(56) References Cited

U.S. PATENT DOCUMENTS

| | | | |
|---|---|---|---|
| 8,182,838 B2 | 5/2012 | Morton | |
| 9,630,990 B2 * | 4/2017 | Shetty | ................. A61K 38/177 |
| 11,780,879 B2 | 10/2023 | Shetty | |
| 2002/0077283 A1 | 6/2002 | Sessa | |
| 2007/0154404 A1 | 7/2007 | Colombo et al. | |
| 2011/0218152 A1 * | 9/2011 | Beliveau | ................. A61P 27/06 |
| | | | 514/19.5 |
| 2013/0224163 A1 | 8/2013 | Head et al. | |
| 2016/0022577 A1 | 1/2016 | Flynn et al. | |
| 2017/0128520 A1 | 5/2017 | Eveleth et al. | |

FOREIGN PATENT DOCUMENTS

| | | | |
|---|---|---|---|
| CN | 107405379 A | 11/2017 | |
| JP | 2005-503321 | 2/2005 | |
| JP | 2018-507867 | 3/2018 | |
| KR | 2005-0003416 | 1/2005 | |
| WO | WO 02/020768 | 3/2002 | |
| WO | WO 2003/016540 | 2/2003 | |
| WO | WO 2003/094890 | 11/2003 | |
| WO | WO 2014/145389 | 9/2014 | |
| WO | WO 2016/138413 | 9/2016 | |
| WO | WO-2016138413 A1 * | 9/2016 | ............. A61K 38/08 |

OTHER PUBLICATIONS

Markarian, Jennifer, Inhalation Drug Manufacturing, Pharmaceutical Technology, 42(4). Examiner Generated pdf. (Year: 2018).*
Loh et al., Overview of milling techniques for improving the solubility of poorly water-soluble drugs, Asian Journal of Pharmaceutical Science: 10: 255-274. (Year: 2015).*
Sou et al., Designing a multi-component spray-dried formulation platform for pulmonary delivery of biopharmaceuticals: The use of polyol, disaccharide, polysaccharide and synthetic polymer to modify solid-state properties for glassy stabilization, Powder Technology; 287: 248-255. (Year: 2016).*
Li et al., L-Leucine as an excipient against moisture on in vitro aerosolization performances of highly hygroscopic spray-dried powders, European Journal of Pharmaceutics and Biopharmaceutics; 102: 132-141 (Year: 2016).*
Markarian, Optimizing Particle Engineering Methods for Inhalation Drug Products, Pharmaceutical Technology; 42(4). (Year: 2018).*

(Continued)

*Primary Examiner* — Melissa L Fisher
*Assistant Examiner* — John Cronin
(74) *Attorney, Agent, or Firm* — Parker Highlander PLLC

(57) ABSTRACT

Provided herein are compositions comprising caveolin-1 (Cav-1) peptides. Further provided are methods of using the Cav-1 peptides for the treatment of lung infections or acute or chronic lung injury, particularly lung fibrosis.

18 Claims, 18 Drawing Sheets

Specification includes a Sequence Listing.

(56) References Cited

OTHER PUBLICATIONS

Anonymous: "Caveolin-1 scaffolding domain peptide—ALX-153-064—Enzo Life Sciences", dated Aug. 28, 2018 (Aug. 28, 2018), pp. 1-2, XP055919016, Retrieved from the Internet: URL:http://web.archive.org/web/20180828064451/https://www.enzolifesciences.com/ALX-153-064/caveolin-1-scaffolding-domain-pepti de/ [retrieved on May 9, 2022].
Extended European Search Report issued in corresponding European Application No. 19859836.9, dated Jun. 3, 2022.
Irngartinger, M et al. "Pulmonary delivery of therapeutic peptides via dry powder inhalation: Effects of micronisation and manufacturing." *European Journal Of Pharmaceutics And Biopharmaceutics : Official Journal Of Arbeitsgemeinschaft fur Pharmazeutische Verfahrenstechnik e.V* vol. 58,1 (2004): 7-14. doi:10.1016/j.ejpb.2004.03.016.
Schmitz, Matthias et al. "Effect of cavtratin, a caveolin-1 scaffolding domain peptide, on oligodendroglial signaling cascades." *Cellular and molecular neurobiology* vol. 31,7 (2011): 991-7. doi:10.1007/s10571-011-9694-1.
Vandana, K R et al. "An overview on in situ micronization technique—An emerging novel concept in advanced drug delivery." *Saudi pharmaceutical journal : SPJ : the official publication of the Saudi Pharmaceutical Society* vol. 22,4 (2014): 283-9. doi:10.1016/j.jsps.2013.05.004.
Zhang, Yajie et al. "Development of an Excipient-Free Peptide Dry Powder Inhalation for the Treatment of Pulmonary Fibrosis." *Molecular pharmaceutics* vol. 17,2 (2020): 632-644. doi:10.1021/acs.molpharmaceut.9b01085.
Office Communication issued in corresponding Japanese Application No. 2021-538171, dated Jul. 7, 2023. English Translation.
Surasarang et al., "Formulation for a novel inhaled peptide therapeutic for idiopathic pulmonary fibrosis.," *Drug Development and Industrial Pharmacy*, 44(2):184-198, 2017.
De Boer, Anne H., et al. "Dry powder inhalation: past, present and future." *Expert opinion on drug delivery* 14.4 (2017): 499-512.
Office Communication issued in corresponding Chinese Application No. 201980073144.0, dated Sep. 28, 2023. English Translation.
Office Communication issued in corresponding European Application No. 19 859 836.9, dated Dec. 18, 2023. English Translation.
Office Communication issued in corresponding Japanese Application No. 2021-538171, dated Dec. 4, 2023. English Translation.
Phillips, E., et al. "Size reduction of peptides and proteins by jet-milling." *Respiratory drug delivery VI.* 1998.
Shetty, Nivedita, et al. "Physical stability of dry powder inhaler formulations." *Expert opinion on drug delivery* 17.1 (2020): 77-96.
Yamashita, Chikamasa. "The present state and future of dry powder inhalation system." *Drug Delivery System* 21.4 (2006): 417-425. English Abstract.
Zhou, J. Y., Lan Zhang, and S. R. Mao. "Recent progress of dry powder inhalation of proteins and peptides." *Yao xue xue bao=Acta Pharmaceutica Sinica* 50.7 (2015): 814-823. English Abstract.

"AFREZZA®", Highlights of prescribing information, dated Feb. 2023.
"ESUBERA®", NDA 21-868 US Package Insert, dated Jan. 27, 2007.
NCT04233814, "Safety, Tolerability and Pharmacokinetic Study of LTI-03 in Healthy Adult Subjects", dated Mar. 7, 2022, downloaded from ClinicalTrials.gov on Nov. 1, 2024.
NCT05954988, "A Study to Evaluate LTI-03 in Newly Diagnosed Idiopathic Pulmonary Fibrosis (IPF) Patients", dated Aug. 30, 2023, downloaded from ClinicalTrials.gov on Nov. 1, 2024.
O'Callaghan, Christopher, and Peter W. Barry. "The science of nebulised drug delivery." Thorax 52.Suppl 2 (1997): S31.
Office Communication issued in corresponding Korean Application No. 10-2021-7010694, dated Nov. 11, 2024. English Translation.
Aillon, Kristin L., et al. "Iodinated NanoClusters as an inhaled computed tomography contrast agent for lung visualization." *Molecular pharmaceutics* 7.4 (2010): 1274-1282.
Chan, John Gar Yan, et al. "Advances in device and formulation technologies for pulmonary drug delivery." *AAPS Pharmscitech* 15 (2014): 882-897.
Johnson, Elizabeth R., and Michael A. Matthay. "Acute lung injury: epidemiology, pathogenesis, and treatment." *Journal of aerosol medicine and pulmonary drug delivery* 23.4 (2010): 243-252.
King, Paul T. "Inflammation in chronic obstructive pulmonary disease and its role in cardiovascular disease and lung cancer." *Clinical and translational medicine* 4 (2015): 1-13.
Office Communication issued in corresponding U.S. Appl. No. 18/434,731, dated Aug. 15, 2024.
Rogliani, Paola, et al. "Optimizing drug delivery in COPD: the role of inhaler devices." *Respiratory medicine* 124 (2017): 6-14.
Rothe, Thomas et al. "Diagnosis and Management of Asthma—The Swiss Guidelines." *Respiration; international review of thoracic diseases* vol. 95,5 (2018): 364-380.
Welsh, Carolyn H., et al. "An international ISHLT/ATS/ERS clinical practice guideline: summary for clinicians. Bronchiolitis obliterans syndrome complicating lung transplantation." *Annals of the American Thoracic Society* 12.1 (2015): 118-119.
Carvalho et al., "Influence of particle size on regional lung deposition—What evidence is there?" *Int. J. Pharma.* 406:1-10, 2011.
Hübner, R.-H et al., "Standardized quantification of pulmonary fibrosis in histological samples." *Biotechniques*, 44, 507-11, 514-7, 2008.
International Preliminary Report on Patentability issued in corresponding PCT Application No. PCT/US2019/050349, mailed on Mar. 25, 2021.
International Search Report and Written Opinion issued in corresponding PCT Application No. PCT/US2019/050349, mailed on Dec. 11, 2019.
Shetty S, et al. "Induction of p53 by urokinase in lung epithelial cells." *J Biol Chem.* 280(30):28133-41, 2005.
Tepper, J. S.; Kuehl, P. J.; Cracknell, S.; Nikula, K. J.; Pei, L.; Blanchard, J. D. Symposium Summary: "breathe In, Breathe Out, Its Easy: What You Need to Know about Developing Inhaled Drugs." *Int. J. Toxicol.* 35, 376-392, 2016.

* cited by examiner

SEQUENCE LISTING

<160> NUMBER OF SEQ ID NOS: 29

<210> SEQ ID NO 1
<211> LENGTH: 178
<212> TYPE: PRT
<213> ORGANISM: Homo sapiens

<400> SEQUENCE: 1

```
Met Ser Gly Gly Lys Tyr Val Asp Ser Glu Gly His Leu Tyr Thr Val
1               5                   10                  15
Pro Ile Arg Glu Gln Gly Asn Ile Tyr Lys Pro Asn Asn Lys Ala Met
            20                  25                  30
Ala Asp Glu Leu Ser Glu Lys Gln Val Tyr Asp Ala His Thr Lys Glu
        35                  40                  45
Ile Asp Leu Val Asn Arg Asp Pro Lys His Leu Asn Asp Asp Val Val
    50                  55                  60
Lys Ile Asp Phe Glu Asp Val Ile Ala Glu Pro Glu Gly Thr His Ser
65                  70                  75                  80
Phe Asp Gly Ile Trp Lys Ala Ser Phe Thr Thr Phe Thr Val Thr Lys
                85                  90                  95
Tyr Trp Phe Tyr Arg Leu Leu Ser Ala Leu Phe Gly Ile Pro Met Ala
            100                 105                 110
Leu Ile Trp Gly Ile Tyr Phe Ala Ile Leu Ser Phe Leu His Ile Trp
        115                 120                 125
Ala Val Val Pro Cys Ile Lys Ser Phe Leu Ile Glu Ile Gln Cys Ile
    130                 135                 140
Ser Arg Val Tyr Ser Ile Tyr Val His Thr Val Cys Asp Pro Leu Phe
145                 150                 155                 160
Glu Ala Val Gly Lys Ile Phe Ser Asn Val Arg Ile Asn Leu Gln Lys
                165                 170                 175
Glu Ile
```

<210> SEQ ID NO 2
<211> LENGTH: 7
<212> TYPE: PRT
<213> ORGANISM: Artificial sequence
<220> FEATURE:
<223> OTHER INFORMATION: Synthetic amino acid

<400> SEQUENCE: 2

```
Phe Thr Thr Phe Thr Val Thr
1               5
```

<210> SEQ ID NO 3
<211> LENGTH: 9
<212> TYPE: PRT
<213> ORGANISM: Artificial sequence
<220> FEATURE:
<223> OTHER INFORMATION: Synthetic amino acid

<400> SEQUENCE: 3

```
Ala Ser Phe Thr Thr Phe Thr Val Thr
1               5
```

<210> SEQ ID NO 4
<211> LENGTH: 13
<212> TYPE: PRT
<213> ORGANISM: Artificial sequence
<220> FEATURE:
<223> OTHER INFORMATION: Synthetic amino acid

```
<400> SEQUENCE: 4

Lys Ala Ser Phe Thr Thr Phe Thr Val Thr Lys Gly Ser
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic amino acid

<400> SEQUENCE: 5

Lys Ala Ser Phe Thr Thr Phe Thr Val Thr Lys Gly Ser
1               5                   10

<210> SEQ ID NO 6
<211> LENGTH: 19
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(2)
<223> OTHER INFORMATION: X = D-Alanine
<220> FEATURE:
<221> NAME/KEY: MISC_FEATURE
<222> LOCATION: (18)..(19)
<223> OTHER INFORMATION: X = D-Alanine

<400> SEQUENCE: 6

Xaa Xaa Glu Gly Lys Ala Ser Phe Thr Thr Phe Thr Val Thr Lys Gly
1               5                   10                  15

Ser Xaa Xaa

<210> SEQ ID NO 7
<211> LENGTH: 19
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(2)
<223> OTHER INFORMATION: X = D-Alanine
<220> FEATURE:
<221> NAME/KEY: MISC_FEATURE
<222> LOCATION: (18)..(19)
<223> OTHER INFORMATION: X = D-Alanine
<220> FEATURE:
<221> NAME/KEY: MISC_FEATURE
<222> LOCATION: (19)..(19)
<223> OTHER INFORMATION: NH2 functional group present

<400> SEQUENCE: 7

Xaa Xaa Glu Gly Lys Ala Ser Phe Thr Thr Phe Thr Val Thr Lys Gly
1               5                   10                  15

Ser Xaa Xaa

<210> SEQ ID NO 8
<211> LENGTH: 19
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
```

```
<220> FEATURE:
<221> NAME/KEY: MISC_FEATURE
<222> LOCATION: (1)..(2)
<223> OTHER INFORMATION: X = D-Alanine
<220> FEATURE:
<221> NAME/KEY: MISC_FEATURE
<222> LOCATION: (18)..(19)
<223> OTHER INFORMATION: X = D-Alanine
<220> FEATURE:
<221> NAME/KEY: MISC_FEATURE
<222> LOCATION: (19)..(19)
<223> OTHER INFORMATION: NH2 functional group present

<400> SEQUENCE: 8

Xaa Xaa Glu Gly Lys Ala Ser Phe Thr Thr Phe Thr Val Thr Lys Gly
1               5                   10                  15

Ser Xaa Xaa

<210> SEQ ID NO 9
<211> LENGTH: 12
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: X = Ornithine

<400> SEQUENCE: 9

Xaa Ala Ser Phe Thr Thr Phe Thr Val Thr Xaa Ser
1               5                   10

<210> SEQ ID NO 10
<211> LENGTH: 12
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: X = Ornithine
<220> FEATURE:
<221> NAME/KEY: MISC_FEATURE
<222> LOCATION: (12)..(12)
<223> OTHER INFORMATION: NH2 functional group present

<400> SEQUENCE: 10

Xaa Ala Ser Phe Thr Thr Phe Thr Val Thr Xaa Ser
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (7)..(7)
<223> OTHER INFORMATION: NH2 functional group present

<400> SEQUENCE: 11
```

```
Phe Thr Thr Phe Thr Val Thr
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (8)..(8)
<223> OTHER INFORMATION: NH2 functional group present

<400> SEQUENCE: 12

Phe Thr Thr Phe Thr Val Thr Lys
1               5

<210> SEQ ID NO 13
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (11)..(11)
<223> OTHER INFORMATION: NH2 functional group present

<400> SEQUENCE: 13

Lys Ala Ser Phe Thr Thr Phe Thr Val Thr Lys
1               5                   10

<210> SEQ ID NO 14
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (11)..(11)
<223> OTHER INFORMATION: NH2 functional group present

<400> SEQUENCE: 14

Lys Ala Ser Phe Thr Thr Phe Thr Val Thr Lys
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: NH2 functional group present

<400> SEQUENCE: 15

Xaa Ala Ser Phe Thr Thr Phe Thr Val Thr Lys
1               5                   10
```

```
<210> SEQ ID NO 16
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: NH2 functional group present

<400> SEQUENCE: 16

Xaa Ala Ser Phe Thr Thr Phe Thr Val Thr Lys
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (13)..(13)
<223> OTHER INFORMATION: NH2 functional group present

<400> SEQUENCE: 17

Lys Ala Ser Phe Thr Thr Phe Thr Val Thr Lys Gly Ser
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (14)..(14)
<223> OTHER INFORMATION: NH2 functional group present

<400> SEQUENCE: 18

Asp Ser Gly Lys Ala Ser Phe Thr Thr Phe Thr Val Thr Lys
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (14)..(14)
<223> OTHER INFORMATION: NH2 functional group present
```

```
<400> SEQUENCE: 19

Asp Ser Gly Lys Ala Ser Phe Thr Thr Phe Thr Val Thr Lys
1               5                   10

<210> SEQ ID NO 20
<211> LENGTH: 12
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: X = Ornithine
<220> FEATURE:
<221> NAME/KEY: MISC_FEATURE
<222> LOCATION: (12)..(12)
<223> OTHER INFORMATION: NH2 functional group present

<400> SEQUENCE: 20

Xaa Ala Ser Phe Thr Thr Phe Thr Val Thr Xaa Ser
1               5                   10

<210> SEQ ID NO 21
<211> LENGTH: 9
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (9)..(9)
<223> OTHER INFORMATION: NH2 functional group present

<400> SEQUENCE: 21

His Asp Gly Ile Trp Lys Ala Ser Phe
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (9)..(9)
<223> OTHER INFORMATION: NH2 functional group present

<400> SEQUENCE: 22

His Val Thr Lys Tyr Trp Phe Tyr Arg
1               5

<210> SEQ ID NO 23
<211> LENGTH: 13
<212> TYPE: PRT
<213> ORGANISM: Artificial sequence
<220> FEATURE:
<223> OTHER INFORMATION: Synthetic amino acid

<400> SEQUENCE: 23
```

Gly Arg Lys Lys Arg Gln Arg Arg Pro Pro Gln
1               5                   10

<210> SEQ ID NO 24
<211> LENGTH: 16
<212> TYPE: PRT
<213> ORGANISM: Artificial sequence
<220> FEATURE:
<223> OTHER INFORMATION: Synthetic amino acid

<400> SEQUENCE: 24

Arg Gln Ile Lys Ile Trp Phe Gln Asn Arg Arg Met Lys Trp Lys Lys
1               5                   10                  15

<210> SEQ ID NO 25
<211> LENGTH: 26
<212> TYPE: PRT
<213> ORGANISM: Artificial sequence
<220> FEATURE:
<223> OTHER INFORMATION: Synthetic amino acid

<400> SEQUENCE: 25

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 26
<211> LENGTH: 10
<212> TYPE: PRT
<213> ORGANISM: Artificial sequence
<220> FEATURE:
<223> OTHER INFORMATION: Synthetic amino acid

<400> SEQUENCE: 26

Thr Lys Ile Glu Ser Leu Lys Glu His Gly
1               5                   10

<210> SEQ ID NO 27
<211> LENGTH: 10
<212> TYPE: PRT
<213> ORGANISM: Artificial sequence
<220> FEATURE:
<223> OTHER INFORMATION: Synthetic amino acid

<400> SEQUENCE: 27

Thr Gln Ile Glu Asn Leu Lys Glu Lys Gly
1               5                   10

<210> SEQ ID NO 28
<211> LENGTH: 26
<212> TYPE: PRT
<213> ORGANISM: Artificial sequence
<220> FEATURE:
<223> OTHER INFORMATION: Synthetic amino acid

<400> SEQUENCE: 28

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala
            20                  25

<210> SEQ ID NO 29
<211> LENGTH: 25
<212> TYPE: PRT
<213> ORGANISM: Artificial sequence

```
-continued

<220> FEATURE:
<223> OTHER INFORMATION: Synthetic amino acid

<400> SEQUENCE: 29

Gly Leu Phe Glu Ala Ile Glu Gly Phe Ile Glu Asn Gly Trp Glu Gly
1               5                   10                  15

Met Ile Glu Gly Trp Tyr Gly Cys Gly
            20                  25
```

DRY POWDER FORMULATION OF CAVEOLIN-1 PEPTIDES AND METHODS OF USE THEREOF

This application is a national phase application under 35 U.S.C. § 371 of International Application No. PCT/US2019/050349, filed Sep. 10, 2019, which claims the benefit of U.S. Provisional Patent Application No. 62/729,010, filed Sep. 10, 2018, the entirety of each of which is incorporated herein by reference.

The present invention was made as a result of activities undertaken within the scope of a joint research agreement that was in effect at the time the present invention was made. The parties to said joint research agreement are The Board of Regents of the University of Texas System and Lung Therapeutics.

REFERENCE TO AN ELECTRONIC SEQUENCE LISTING

The contents of the electronic sequence listing (UTSBP1188US_ST25.txt; Size; 11,436 bytes and Date of Creation: Mar. 9, 2021) are herein incorporated by reference in its entirety.

BACKGROUND OF THE INVENTION

1. Field of the Invention

The present invention relates generally to the fields of molecular biology, pharmaceutics and medicine. More particularly, it concerns compositions and methods for the delivery of dry powder therapeutic polypeptide compositions to subjects, such as by delivery to the respiratory system.

2. Description of Related Art

During lung injury, p53 expression increases, inducing plasminogen activator inhibitor-1 (PAI-1) while inhibiting expression of urokinase-type plasminogen activator (uPA) and its receptor (uPAR), resulting in apoptosis of lung epithelial cells (LECs). The mechanism of injury involves cell surface signaling interactions between uPA, uPAR, caveolin-1 ("Cav-1") and β1-integrin (Shetty et al., 2005). Compositions that modulate these interactions could be used in methods for inhibiting apoptosis of injured, diseased or damaged tissues. For example, for treating inflammation or fibrotic conditions such as pulmonary fibrosis. Thus, there is a need for polypeptides that could be used to prevent or treat lung injuries and diseases and, in particular, stable formulations and simple methods for therapeutic delivery of such polypeptides.

SUMMARY OF THE INVENTION

In accordance with the present disclosure, there is provided a dry powder composition of peptide comprising the amino acid sequence of SEQ ID NO: 2.

In a first embodiment, there is provided a pharmaceutical composition comprising a dry powder of a peptide, said peptide comprising a sequence of anyone of SEQ ID NOs: 2-20. In some aspects, the peptide is 7-20 amino acids in length. In a particular aspect, the peptide comprises the amino acid sequence of SEQ ID NO: 2. In further aspects, the peptide comprises at least one amino acid added to the N-terminus of a peptide of SEQ ID NO: 2. In other aspects, the peptide comprises at least one amino acid added to the C-terminus of a peptide of SEQ ID NO: 2. In another aspect, the peptide comprises at least one amino acid added to the N-terminus and the C-terminus of a peptide of SEQ ID NO: 2. In certain aspects the peptide may comprise L-amino acids or D-amino acids or both L- and D-amino acids. In additional aspects, the peptide may comprise at least one non-standard amino acid. In several aspects, the peptide comprises 2 non-standard amino acids. In a specific aspect, the non-standard amino acid is ornithine.

In further aspects, the peptide may comprise a N-terminal modification or a C-terminal modification or both a N- and C-terminal modification. In a particular aspect, the N-terminal modification is acylation. In another aspect, the C-terminal modification is amidation.

In some aspects, the peptide may comprise the amino acid sequence of SEQ ID NO: 3, SEQ ID NO: 4, SEQ ID NO: 6, SEQ ID NO: 9, SEQ ID NO: 5, SEQ ID NO: 7, SEQ ID NO: 8, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 10, or SEQ ID NO: 20. In several aspects, the peptide comprises at least two repeats of a sequence of any one of SEQ ID NOs: 2-20. In specific aspects, the at least two repeats have identical amino acid sequences. In other aspects, the at least two repeats have different amino acid sequences. In still further aspects, the pharmaceutical composition additionally comprises a cell-penetrating peptide (CPP). In certain aspects, the CPP comprises an amino acid sequence selected from the group comprising: GRKKRRQRRRPPQ (SEQ ID NO: 23), RQIKIWFQNRRMKWKK (SEQ ID NO: 24), and GIGAVLKVLTTGLPALISWIKRKRQQ (SEQ ID NO: 25).

In additional aspects, the dry powder is produced by a milling process. In several aspects, the dry powder is produced by a spray-drying process. In alternative aspects, the dry powder is produced by air jet milling, ball milling, or wet milling. In some aspects, the dry powder comprises less than 10% (by weight) of water. In another aspect, the dry powder comprises less than 1% (by weight) of water. In certain aspects, the pharmaceutical composition is essentially excipient free. In a specific aspect, the pharmaceutical composition is excipient free. In particular aspects, the pharmaceutical composition is formulated for lung delivery. In a further aspect, the pharmaceutical composition is formulated for dry powder inhalation. In other aspects, the pharmaceutical composition is formulated for inhalation pressurized metered dose inhalation. In some aspects, the pharmaceutical composition is formulated for oral administration, topical administration or injection.

In certain aspects, a dry powder formulation of the embodiments comprises a water content of less than about 10%, 9%, 8%, 7%, 6% or 5%. In further aspects, a composition comprises a water content of about 0.01% to about 10%, 0.1% to about 10%, 1.0% to about 8% or 1% to about 5%. In further aspects, a dry powder formulation of the embodiment comprises an average particle size of less than 10 μm. In certain aspects, the average particle size is about 0.01 μm to about 10 μm; about 0.1 μm to about 8 μm; about 0.5 μm to about 7 μm or about 1 μm to about 5 In some aspects, at least about 50%, 55%, 60%, 65% or 70% of a dry powder composition of the embodiments comprises a particle size of about 1 μm to about 5 μm. In certain aspects, a dry powder formulation of the peptide of the embodiments (e.g., CSP7) is composed of at least 70% (e.g. 70%-80%) particles having a size of about 1 μm to about 5 μm. In preferred aspects, at least about 70%, 75%, 80%, or 85% (e.g., 75%-95%) of particles in the dry powder formulation are less than 5 μm in size.

A further embodiment of the invention provides a nebulizer device comprising a pharmaceutical composition of the embodiment and aspects described above.

In still a further embodiment, there is provided a method of treating a subject comprising administering to the subject an effective amount of a pharmaceutical composition of the embodiment and aspects described above to a subject. In certain aspects, the subject has an inflammatory disorder. In other aspects, the subject has a fibrotic condition. In several aspects, the subject has pulmonary inflammation, acute lung injury, lung infection or lung. In another aspect, the subject has pulmonary inflammation. In a specific aspect, the subject has chronic obstructive pulmonary disorder (COPD). In further aspects, the subject may have an acute lung injury or infection, a lung infection, a chemical-induced lung injury, plastic bronchitis, asthma, acute respiratory distress syndrome (ARDS), inhalational smoke induced acute lung injury (ISALI), bronchiolitis, or bronchiolitis obliterans. In particular aspects, the lung disease is a fibrotic condition of the lungs, interstitial lung disease, or Idiopathic Pulmonary Fibrosis (IPF) or lung scarring. In additional aspects, the administering comprises dry powder inhalation. In other aspects, the administering comprises nebulizing a solution comprising the variant polypeptide.

In further aspects, the method additionally comprises administering at least one additional anti-fibrotic therapeutic. In some aspect, the at least one additional anti-fibrotic is NSAID, steroid, DMARD, immunosuppressive, biologic response modulators, or bronchodilator. In several aspects, the subject is a human.

Yet a further embodiment of the invention provides a pharmaceutical composition, comprising a peptide of SEQ ID Nos: 2-20 formulated a milled dry powder having a respirable particle size. For example, in certain aspects, the milled dry powder comprises a mass median aerodynamic diameter (MMAD) of less than about 10 microns. Methods for determining MMAD are provided for instance in Carvalho et al., 2011, which is incorporated herein by reference.

In still a further embodiment, there is provided a method of treating a subject comprising administering an effective amount of a composition of the embodiments to the subject by inhalation.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 18: Particle deposition of Aerosolized CSP7. After aerosolization using a Next Generation Impactor (NGI), all collection surfaces were rinsed with known volumes of 20 mM Tris buffer (pH 10.3). Powders deposited in the throat, pre-separator, and stages 1-MOC were extracted separately and measured. Indicated is the percentage of unprocessed or air jet milled (batch 171013) CSP7 powder (collected from collection vessel) deposited in a specific location.

FIG. 19: Aerodynamic Particle Size Distribution of Air Jet Milled CSP7. After aerosolization using a Next Generation Impactor (NGI), all collection surfaces were rinsed with known volumes of 20 mM Tris buffer (pH 10.3). Powders deposited in the capsule, device, adaptor, throat, pre-separator, and stages 1-MOC were extracted separately and measured. The locations within the mill where either unprocessed or air jet milled (batch 171027) CSP7 powder (collected from all fractions of milled powder) was determined. The percentage of the milled powder present in each location is shown.

DESCRIPTION OF ILLUSTRATIVE EMBODIMENTS

I. Definitions

Figure 1:
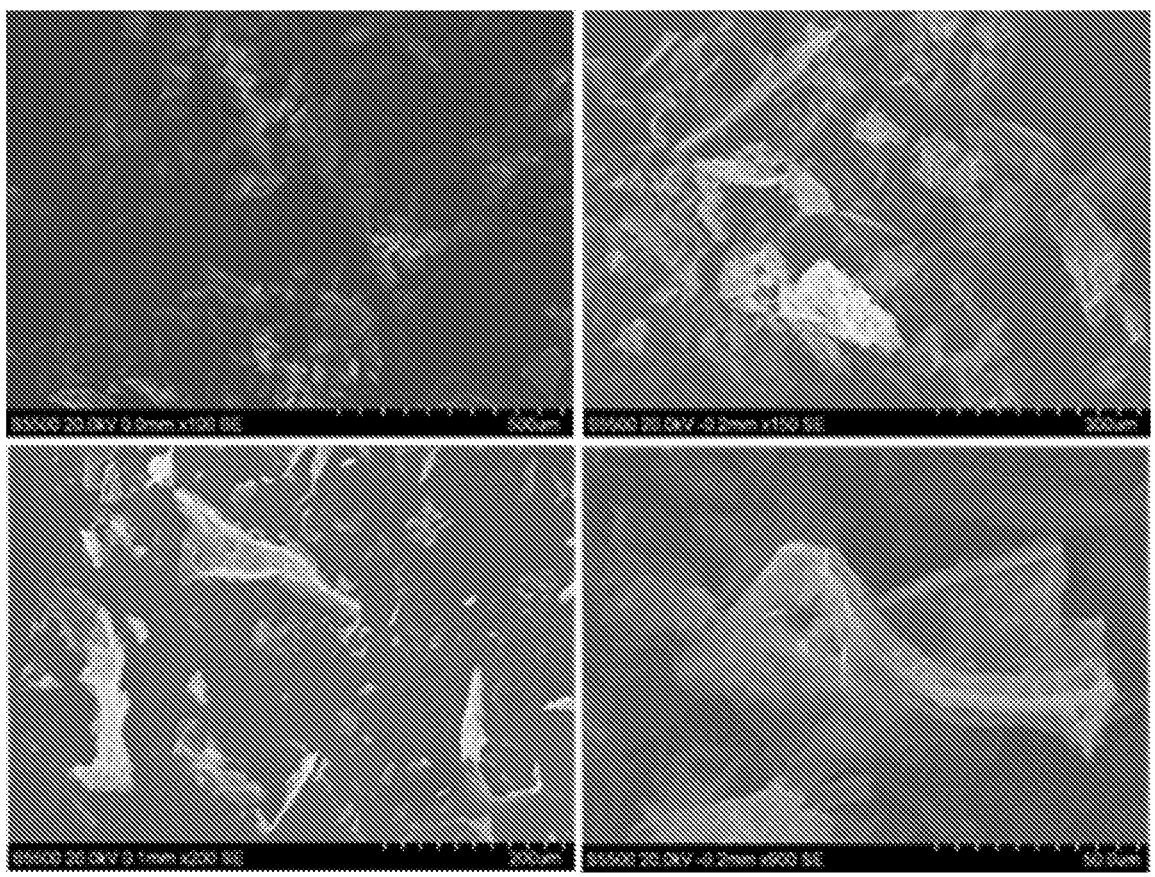
FIG. 1: Scanning Electron Microscopy Images of CSP7 Bulk Powder. Powder samples were sputtered on the sample tray and spread by blowing compressed nitrogen. Samples were viewed using a Hitachi S5500 SEM/STEM scanning electron microscope. Scale bars are pictured at the lower right of images.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. "About" means+/−10% unless otherwise noted.

The term "peptide" as used herein typically refers to a sequence of amino acids made up of a single chain of amino acids joined by peptide bonds. Generally, peptides contain at least two amino acid residues and are less than about 50 amino acids in length, unless otherwise defined. In some aspects, a peptide may be provided with a counterion. Likewise, in some cases, a peptide may include a N and/or C-terminal modification such a as blocking modification that reduced degradation.

A "biologically active" caveolin-1 (Cav-1) peptide refers to a peptide that increases p53 protein levels, reduces urokinase plasminogen activator (uPA) and uPA receptor (uPAR), and/or increases plasminogen activator inhibitor-1 (PAI-1) expression in cells, such as fibrotic lung fibroblasts. In some aspects, the biologically active peptide has at least 20% of the biological or biochemical activity of native Cav-1 polypeptide of SEQ ID NO: 1 (e.g., as measured by an in vitro or an in vivo assay). In some aspects, the biological active peptide has the same or an increase biological or biochemical activity as compared to the native Cav-1 polypeptide.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "polypeptide" or "protein" is used in its broadest sense to refer to a compound of two or more subunit amino acids, amino acid analogs, or peptidomimetics. The subunits may be linked by amide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. The term "peptidomimetic" or "peptide mimic" means that a peptide according to the invention is modified in such a way that it includes at least one non-peptidic bond such as, for example, urea bond, carbamate bond, sulfonamide bond, hydrazine bond, or any other covalent bond. A peptide of three or more amino acids is commonly called an oligopeptide if the peptide chain is short. If the peptide chain is long (e.g., longer than 50 amino acids), the peptide is commonly called a polypeptide or a protein.

The terms "subject" and "individual" and "patient" are used interchangeably herein, and refer to an animal, for example a human or non-human animal (e.g., a mammal), to whom treatment, including prophylactic treatment, with a pharmaceutical composition as disclosed herein, is provided. The term "subject" as used herein refers to human and non-human animals. The term "non-human animals" includes all vertebrates, e.g., mammals, such as non-human primates, (particularly higher primates), sheep, dogs, rodents (e.g. mouse or rat), guinea pigs, goats, pigs, cats, rabbits, cows, and non-mammals such as chickens, amphibians, reptiles etc. In one embodiment, the subject is human. In another embodiment, the subject is an experimental animal or animal substitute as a disease model. Non-human mammals include mammals such as non-human primates, (particularly higher primates), sheep, dogs, rodents (e.g. mouse or rat), guinea pigs, goats, pigs, cats, rabbits and cows. In some aspects, the non-human animal is a companion animal such as a dog or a cat.

"Treating" a disease or condition in a subject or "treating" a patient having a disease or condition refers to subjecting the individual to a pharmaceutical treatment, e.g., the administration of a drug, such that at least one symptom of the disease or condition is decreased or stabilized. Typically, when the peptide is administered therapeutically as a treatment, it is administered to a subject who presents with one or more symptoms of lung injury or lung fibrosis.

By "isolated" it is meant that the polypeptide has been separated from any natural environment, such as a body fluid, e.g., blood, and separated from the components that naturally accompany a polypeptide.

By isolated and "substantially pure" is meant a polypeptide that has been separated and purified to at least some degree from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

The term "variant" as used herein refers to a polypeptide that differs from the polypeptide by one or more amino acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments, amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

An "analog" of a molecule such as a peptide refers to a molecule similar in function to either the entire molecule or to a fragment thereof. The term "analog" is also intended to include allelic species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond. In some aspects of all the embodiments of the invention, the fusion peptides are covalently bonded.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6, digoxigenin, FITC, Cy3, Cy5, green fluorescent protein, V5 epitope tags, GST, β-galactosidase, AU1, AU5, and avidin. Half-life extenders include Fc domain and serum albumin.

The term "airway" refers herein to any portion of the respiratory tract including the upper respiratory tract, the respiratory airway, and the lungs. The upper respiratory tract includes the nose and nasal passages, mouth, and throat. The respiratory airway includes the larynx, trachea, bronchi and bronchioles. The lungs include the respiratory bronchioles, alveolar ducts, alveolar sacs and alveoli.

The terms "inhalational smoke induced acute lung injury" and "ISALI" are used interchangeably herein and refer to a form of acute lung injury (ALI) caused by smoke inhalation. ALI is also referred to as "mild Acute Respiratory Distress Syndrome; ARDS." ARDS can be defined by finding one or more of the following conditions in a subject: 1) bilateral pulmonary infiltrates on chest x-ray, 2) when measured by right heart catheterization as clinically indicated, pulmonary capillary wedge pressure <18 mmHg (2.4 kPa), and 3) $PaO_2/FiO_2 < 300$ mmHg (40 kPa). In some embodiments, treatment of ISALI includes treatment of one or more of the following conditions: reduced oxygenation, airway obstruction (including a severe airway obstruction), fibrinous airway casts or debris, and alveolar fibrin deposition.

The term "air jet mill" refers to a device or method for reducing particle size by using a jet of compressed gas to impact particles into one another, thereby pulverizing the particles. An air jet mill may be used to reduce the size of peptide particles. Other mechanical milling devices that perform the same function can also be used interchangeably with the air jet mill. Air jet milling can occur under various environmental parameters such as temperature, pressure, relative/absolution humidity, oxygen content, etc.

The term "ball mill" refers to a device or method for reducing particle size by adding the particle of interest and a grinding medium to the interior of a cylinder and rotating the cylinder. The particles of interest are broken down as the grinding medium rises and falls along the exterior of the cylinder as it rotates. A ball mill may be used to reduce the size of peptide particles. Other mechanical milling devices that perform the same function can also be used interchangeably with the air jet mill.

The term "wet mill" or "media mill" refers to a device or method for reducing particle size by adding the particle of interest to device with an agitator, containing a media comprising a liquid and a grinding medium. With the addition of the particle of interest, as the agitator rotates, the energy it disperses causes the grinding medium and particles of interest to come into contact and break down the particles of interest. Other mechanical milling devices that perform the same function can also be used interchangeably with the air jet mill.

The term "high pressure homogenization" refers to a method of reducing particle size by adding the particle of interest to a device which combines both pressure and mechanical forces to break down the particle of interest. Mechanical forces used in high pressure homogenization may include impact, shear, and cavitation, among others. Other mechanical milling devices that perform the same function can also be used interchangeably with the air jet mill.

The term "cryogenic mill" refers to a device or method for reducing particle size by first chilling a particle of interest with dry ice, liquid nitrogen, or other cryogenic liquid, and subsequently milling the particle of interest to reduce the size. Other mechanical milling devices that perform the same function can also be used interchangeably with the air jet mill.

The phrase "effective amount" or "therapeutically effective" means a dosage of a drug or agent sufficient to produce a desired therapeutic result. The desired therapeutic result can be subjective or objective improvement in the recipient of the dosage, reduced infection, reduced inflammation, increased lung growth, increased lung repair, reduced tissue edema, increased DNA repair, decreased apoptosis, a decrease in tumor size, a decrease in the rate of growth of cancer cells, a decrease in metastasis, or any combination of the above.

As used herein, "excipient" refers to pharmaceutically acceptable carriers that are relatively inert substances used to facilitate administration or delivery of an Active Pharmaceutical Ingredient (API) into a subject or used to facilitate processing of an API into drug formulations that can be used pharmaceutically for delivery to the site of action in a subject. Excipients or pharmaceutically acceptable carriers include all of the inactive components of the dosage form except for the active ingredient(s). Non-limiting examples of excipients include carrier agents, bulking agents, stabilizing agents, surfactants, surface modifiers, solubility enhancers, buffers, encapsulating agents, antioxidants, preservatives, nonionic wetting or clarifying agents, viscosity increasing agents, and absorption-enhancing agents. "Excipient free" refers to the pharmaceutical composition of interest in a formulation free of any excipients.

The phrases "pharmaceutical composition" or "pharmacologically acceptable composition" refers to molecular entities and compositions that do not produce an adverse, allergic, or other untoward reaction when administered to an animal, such as a human, as appropriate. The preparation of a pharmaceutical composition comprising a Cav-1 peptide, such as CSP7, or additional active ingredients will be known to those of skill in the art in light of the present disclosure. Moreover, for animal (e.g., human) administration, it will be understood that preparations should meet bioburden, sterility, pyrogenicity, general safety, and/or purity standards as required by the FDA or other recognized regulatory authority.

As used herein, "pharmaceutically acceptable carrier" includes any and all excipients, processing aids, aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, disintegration agents, lubricants, flavor modifiers (e.g., sweetening agents, flavoring agents), such like materials and combinations thereof, as would be known to one of ordinary skill in the art. The 10 pH and exact concentration of the various components in a pharmaceutical composition are adjusted according to well-known parameters. In some aspects, the carrier may encapsulate a therapeutic agent, but not itself be consumed or administered to a subject (e.g., a shell capsule encasing a dry powder composition, such as for use in a dry powder inhaler).

II. Caveolin-1 Peptides

Embodiments of the present disclosure provide dry powder formulation of caveolin-1 (Cav-1) peptides. The caveolin-1 (Cav-1) scaffolding domain or peptide interferes with Cav-1 interaction with Src kinases mimics the combined effect of uPA and anti-β1-integrin antibody. Native human Cav-1 has a length of 178 amino acids and a molecular weight of 22 kDa. The amino acid sequence of Cav-1 is shown below (SEQ ID NO: 1).

```
  1  MSGGKYVDSE GHLYTVPIRE QGNIYKPNNK AMADELSEKQ
     VYDAHTKEID LVNRDPKHLN

61  DDVVKIDFED VIAEPEGTHS FDGIWKASFT TFTVTKYWFY
     RLLSALFGIP MALIWGIYFA

121  ILSFLHIWAV VPCIKSFLIE IQCISRVYSI YVHTVCDPLF
     EAVGKIFSNV RINLQKEI
```

In some aspects, the peptide is a scaffolding domain peptide which comprises an amino acid sequence at least about 40%, 50%, 60%, 70%, 80%, 85%, 80%, 85%, 90%, 91%, 92%, 93%, 94%, 95%, 96%, 97%, 98% or 99% identical to SEQ ID NO: 2, FTTFTVT. The peptide may comprise 1, 2, 3, 4 or more amino acid substitutions, deletions, or insertions relative to the sequence of SEQ ID NO:1, such as to derive a polypeptide of 3, 4, 5, 6, 7, 8, 9, 10, 11, 12, 13, 14, 15, 16, 17, 18, or 19 residues. In particular aspects, the peptides are truncations of the native Cav-1 polypeptide, such as the exemplary peptides shown in Table 1.

TABLE 1

Exemplary Cav-1 peptides.

| Sequence | ID |
|---|---|
| FTTFTVT | SEQ ID NO: 2 |
| ASFTTFTVT | SEQ ID NO: 3 |
| KASFTTFTVTKGS | SEQ ID NO: 4 |
| KASFTTFTVTKGS-NH2 | SEQ ID NO: 5 |
| aaEGKASFTTFTVTKGSaa | SEQ ID NO: 6 |
| aaEGKASFTTFTVTKGSaa-NH2 | SEQ ID NO: 7 |
| Ac-aaEGKASFTTFTVTKGSaa-NH2 | SEQ ID NO: 8 |
| OASFTTFTVTOS | SEQ ID NO: 9 |
| OASFTTFTVTOS-NH2 | SEQ ID NO: 10 |
| FTTFTVT-NH2 | SEQ ID NO: 11 |
| FTTFTVTK-NH2 | SEQ ID NO: 12 |
| KASFTTFTVTK-NH2 | SEQ ID NO: 13 |
| Ac-KASFTTFTVTK-NH2 | SEQ ID NO: 14 |
| OASFTTFTVTK-NH2 | SEQ ID NO: 15 |
| Ac-OASFTTFTVTK-NH2 | SEQ ID NO: 16 |
| Ac-KASFTTFTVTKGS-NH2 | SEQ ID NO: 17 |
| DSGKASFTTFTVTK-NH2 | SEQ ID NO: 18 |
| Ac-DSGKASFTTFTVTK-NH2 | SEQ ID NO: 19 |
| Ac-OASFTTFTVTOS-NH2 | SEQ ID NO: 20 |
| H-DGIWKASF-NH2 | SEQ ID NO: 21 |
| H-VTKYWFYR-NH2 | SEQ ID NO: 22 |

(a = D-Alanine, O = Ornithine)

The peptides provided in the present disclosure are biologically active derivatives which have the activity of the native Cav-1 polypeptide in in vitro or in vivo assays of binding or of biological activity. In particular aspects, the peptide inhibits or prevents apoptosis of lung epithelial cells (LECs) induced by bleomycin in vitro or in vivo with activity at least about 20% of the activity of the native Cav-1 polypeptide, or at least about 30%, 40%, 50%, 60%, 65%, 70%, 75%, 80%, 85%, 90%, about 95%, 97%, 99%, and any range derivable therein, such as, for example, from about 70% to about 80%, and more preferably from about 81% to about 90%; or even more preferably from about 91% to about 99%. The peptide may have 100% or even greater activity than the native CAV-1 polypeptide. Assays for testing biological activity, e.g., anti-fibrotic activity, the ability to affect expression of uPA, uPAR and PAI-1 mRNAs, or inhibit proliferation of lung fibroblasts, are well-known in the art.

The peptides of the present disclosure are peptides of the native Cav-1 polypeptide or modified versions thereof. The peptides can be synthetic, recombinant, or chemically modified peptides isolated or generated using methods well known in the art. Modifications can be made to amino acids on the N-terminus, C-terminus, or internally. N-terminal modifications may be, for example but not limited to, acylation, acetylation, or C-terminal amidation. Peptides can include conservative or non-conservative amino acid changes, as described below. Polynucleotide changes can result in amino acid substitutions, additions, deletions, fusions and truncations in the polypeptide encoded by the reference sequence. Peptides can also include insertions, deletions or substitutions of amino acids, including insertions and substitutions of amino acids (and other molecules) that do not normally occur in the amino acid sequence that is the basis of the peptide for example but not limited to insertion L-amino acids, or non-standard amino acids such as ornithine, which do not normally occur in human proteins. The term conservative substitution, when describing a peptide, refers to a change in the amino acid composition of the peptide that does not substantially alter the peptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine.

Conservative amino acid substitutions result from replacing one amino acid with another having similar structural and/or chemical properties, such as the replacement of a leucine with an isoleucine or valine, an aspartate with a glutamate, or a threonine with a serine. Thus, a conservative substitution of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered conservative substitutions if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, *J. Mol Biol,* 1999, 217, 721-739 and Taylor et al, *J. Theor. Biol.* 119(1986); 205-218 and S. French and B. Robson, *J. Mol. Evol.* 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

In some aspects, the polypeptides are derivatives of the native Cav-1 polypeptide. The term "derivative" as used herein refers to peptides which have been chemically modified, for example but not limited to by techniques such as acetylation, ubiquitination, labeling, pegylation (derivatization with polyethylene glycol), lipidation, glycosylation, amidation, or addition of other molecules. A molecule is also a "derivative" of another molecule when it contains additional chemical moieties not normally a part of the molecule. Such moieties can alter the pH or improve the molecule's stability, solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., Mack Publ., Easton, Pa. (1990), incorporated herein, by reference, in its entirety.

The term "functional" when used in conjunction with "derivative" or "variant" refers to a polypeptide of the invention which possesses a biological activity (either functional or structural) that is substantially similar to a biological activity of the entity or molecule it is a functional derivative or functional variant thereof. The term functional derivative is intended to include the fragments, analogues or chemical derivatives of a molecule.

In some aspects, amino acid substitutions can be made in a polypeptide at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in a polypeptide and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the polypeptides described herein may be modified by the substitution of an amino acid, for different, but homologous amino acid with a similar hydrophilicity value. Amino acids with hydrophilicities within +/−1.0, or +/−0.5 points are considered homologous.

The Cav-1 peptides may comprise co-translational and post-translational (C-terminal peptide cleavage) modifications, such as, for example, disulfide-bond formation, glycosylation, acetylation, phosphorylation, proteolytic cleavage (e.g., cleavage by furins or metalloproteases), and the like to the extent that such modifications do not affect the anti-inflammatory properties of the isolated peptides or their capacity to improve glycemic control.

In some aspects, the Cav-1 peptide comprises non-naturally occurring amino acids. The peptides can comprise a combination of naturally occurring and non-naturally occurring amino acids, or may comprise only non-naturally occurring amino acids. The non-naturally occurring amino acids can include synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral transepithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class Il-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides.

In addition to the 20 "standard" L-amino acids, D-amino acids or non-standard, modified or unusual amino acids which are well-defined in the art are also contemplated for use in the present disclosure. Phosphorylated amino acids (Ser, Thr, Tyr), glycosylated amino acids (Ser, Thr, Asn), β-amino acids, GABA, ω-amino acids are further contemplated for use in the present disclosure. These include, for example, include β-alanine (β-Ala) and other ω-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); norleucine (Nle); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); homoarginine (hArg); N-acetyl lysine (AcLys); 2,4-diaminobutyric acid (Dbu); 2,4-diaminobutyric acid (Dab); p-aminophenylalanine (Phe(pNH2)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

Carboxy terminal modifications include acylation with carboxylic acids: formic, acetic, propionic, fatty acids (myristic, palmitic, stearic), succinic, benzoic, carbobenzoxy (Cbz); acetylation and biotinylation. Amino terminal modifications include: (i) acylation with carboxylic acids: formic, acetic, propionic, fatty acids (myristic, palmitic, stearic, etc) succinic, benzoic, carbobenzoxy (Cbz); (ii) biotinylation; (iii) amidation; (iv) attachment of dyes such as fluorescein (FITC, FAM, etc.), 7-hydroxy-4-methylcoumarin-3-acetic acid, 7-hydroxycoumarin-3-acetic acid, 7-metoxycoumarin-3-acetic acid and other coumarins; rhodamines (5-carboxyrhodamine 110 or 6G, 5(6)-TAMRA, ROX); N-[4-(4-dimethylamino)phenylazolbezoic acid (Dabcyl), 2,4-dinitrobenzene (Dnp), 5-dimethylaminonaphthalene-1-sulfonic acid (Dansyl) and other dyes; and (v) polyethyleneglycol.

The polypeptide may be capped at its N and C termini with an acyl (abbreviated "Ac")—and an amido (abbreviated "Am") group, respectively, for example acetyl ($CH_3CO$—) at the N terminus and amido (—$NH_2$) at the C terminus. A broad range of N-terminal capping functions, preferably in a linkage to the terminal amino group, is contemplated, for example: formyl;
  alkanoyl, having from 1 to 10 carbon atoms, such as acetyl, propionyl, butyryl;
  alkenoyl, having from 1 to 10 carbon atoms, such as hex-3-enoyl;
  alkynoyl, having from 1 to 10 carbon atoms, such as hex-5-ynoyl;
  aroyl, such as benzoyl or 1-naphthoyl;
  heteroaroyl, such as 3-pyrroyl or 4-quinoloyl;
  alkylsulfonyl, such as methanesulfonyl;
  arylsulfonyl, such as benzenesulfonyl or sulfanilyl;
  heteroarylsulfonyl, such as pyridine-4-sulfonyl;
  substituted alkanoyl, having from 1 to 10 carbon atoms, such as 4-aminobutyryl;
  substituted alkenoyl, having from 1 to 10 carbon atoms, such as 6-hydroxy-hex-3-enoyl;
  substituted alkynoyl, having from 1 to 10 carbon atoms, such as 3-hydroxy-hex-5-ynoyl;
  substituted aroyl, such as 4-chlorobenzoyl or 8-hydroxynaphth-2-oyl;
  substituted heteroaroyl, such as 2,4-dioxo-1,2,3,4-tetrahydro-3-methyl-quinazolin-6-oyl;
  substituted alkylsulfonyl, such as 2-aminoethanesulfonyl;
  substituted arylsulfonyl, such as 5-dimethylamino-1-naphthalenesulfonyl;
  substituted heteroarylsulfonyl, such as 1-methoxy-6-isoquinolinesulfonyl;
  carbamoyl or thiocarbamoyl;
  substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;
  substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide or ester bond with the terminal carboxyl. Capping functions that provide for an amide bond are designated as $NR^1R^2$ wherein $R^1$ and $R^2$ may be independently drawn from the following group: hydrogen;

alkyl, preferably having from 1 to 10 carbon atoms, such as methyl, ethyl, isopropyl;

alkenyl, preferably having from 1 to 10 carbon atoms, such as prop-2-enyl;

alkynyl, preferably having from 1 to 10 carbon atoms, such as prop-2-ynyl;

substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;

substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;

substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;

aroylalkyl having up to 10 carbon atoms, such as phenacyl or 2-benzoylethyl;

aryl, such as phenyl or 1-naphthyl;

heteroaryl, such as 4-quinolyl;

alkanoyl having from 1 to 10 carbon atoms, such as acetyl or butyryl;

aroyl, such as benzoyl;

heteroaroyl, such as 3-quinoloyl;

OR' or NR'R" where R' and R" are independently hydrogen, alkyl, aryl, heteroaryl, acyl, aroyl, sulfonyl, sulfinyl, or $SO_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard H, Ed: *Design of Prodrugs*, Elsevier, Amsterdam, 1985).

Judicious choice of capping groups allows the addition of other activities on the peptide. For example, the presence of a sulfhydryl group linked to the N- or C-terminal cap will permit conjugation of the derivatized peptide to other molecules.

In yet a further aspect, the peptides or fragments or derivatives thereof can be "retro-inverso peptides." A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous a-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., *Int J Pept Protein Res.* 24(6):553-6 (1984); Verdini, A and Viscomi, G. C, *J. Chem. Soc. Perkin Trans.* 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60, expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

B. Multimeric Polypeptides

Embodiments of the present disclosure also include longer polypeptides built from repeating units of Cav-1 peptides. A polypeptide multimer may comprise different combinations of polypeptide. Such multimeric polypeptides can be made by chemical synthesis or by recombinant DNA techniques as discussed herein. When produced by chemical synthesis, the oligomers preferably have from 2-5 repeats of a core polypeptide sequence, and the total number of amino acids in the multimer should not exceed about 160 residues, preferably not more than 100 residues (or their equivalents, when including linkers or spacers).

C. Peptidomimetics

The Cav-1 peptide may be a peptidomimetic compound which mimics the biological effects of the native Cav-1 polypeptide. A peptidomimetic agent may be an unnatural peptide or a non-peptide agent that recreates the stereospatial properties of the binding elements of the native Cav-1 polypeptide such that it has the binding activity and biological activity of the native Cav-1 polypeptide. Similar to a native Cav-1 polypeptide or polypeptide multimer, a peptidomimetic will have a binding face (which interacts with any ligand to which native Cav-1 binds) and a non-binding face.

In some aspects, the present disclosure also includes compounds that retain partial peptide characteristics. For example, any proteolytically unstable bond within a peptide of the invention could be selectively replaced by a non-peptidic element such as an isostere (N-methylation; D-amino acid) or a reduced peptide bond while the rest of the molecule retains its peptidic nature.

Peptidomimetic compounds, either agonists, substrates or inhibitors, have been described for a number of bioactive peptides/polypeptides such as opioid peptides, VIP, thrombin, HIV protease, etc. Methods for designing and preparing peptidomimetic compounds are known in the art (Hruby, V J, *Biopolymers* 33:1073-1082 (1993); Wiley, R A et al., *Med Res. Rev.* 13:327-384 (1993); Moore et al., *Adv. in Pharmacol* 33:91-141 (1995); Giannis et al., *Adv. in Drug Res.* 29:1-78 (1997). Certain mimetics that mimic secondary structure are described in Johnson et al., In: *Biotechnology and Pharmacy*, Pezzuto et al., Chapman and Hall (Eds.), NY, 1993. These methods are used to make peptidomimetics that possess at least the binding capacity and specificity of the native Cav-1 polypeptide and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the three-dimensional structure of a polypeptide of the invention either free or bound in complex with a ligand (e.g., soluble uPAR or a fragment thereof). Alternatively, the structure of a polypeptide of the invention bound to its ligand can be gained by the techniques of nuclear magnetic resonance spectroscopy. Greater knowledge of the stereochemistry of the interaction of the peptide with its ligand or receptor will permit the rational design of such peptidomimetic agents. The structure of a peptide or polypeptide of the invention in the absence of ligand could also provide a scaffold for the design of mimetic molecules.

D. PEGylation

The Cav-1 peptides may be conjugated with heterologous polypeptide segments or polymers, such as polyethylene glycol. The polypeptides may be linked to PEG to increase the hydrodynamic radius of the enzyme and hence increase the serum persistence. The polypeptides may be conjugated to any targeting agent, such as a ligand having the ability to specifically and stably bind to an external receptor (U.S. Patent Publ. 2009/0304666).

In certain aspects, methods and compositions of the embodiments are related to PEGylation of disclosed polypeptides. PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGS are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances, polyethylene glycol (PEG diol) is used as the precursor molecule. The diol is subsequently modified at both ends in order to make a hetero- or homodimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

E. Fusion Proteins

Certain embodiments of the present invention concern fusion proteins of the Cav-1 peptides. These molecules may have the polypeptides of the embodiments linked at the N- or C-terminus to a heterologous domain. For example, fusions may also employ leader sequences from other species to permit the recombinant expression of a protein in a heterologous host. Fusion proteins can comprise a half-life extender. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the peptide of the embodiments may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

2. Linkers

In certain embodiments, the polypeptide of the embodiments may be chemically conjugated using bifunctional cross-linking reagents or fused at the protein level with peptide linkers.

Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the polypeptide of the embodiments, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become especially popular because of their commercial availability, ease of synthesis, and the mild reaction conditions under which they can be applied.

A majority of heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine polypeptides of the embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

3. Cell Penetrating and Membrane Translocation Peptides

Furthermore, in certain aspects, the Cav-1 peptides may further comprise a cell-binding domain or cell penetrating peptide (CPP). As used herein the terms "cell penetrating peptide" and "membrane translocation domain" are used interchangeably and refer to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ (SEQ ID NO: 23)), herpes virus VP22, the *Drosophila* Antennapedia homeobox gene product, protegrin I, Penetratin (RQIKIWFQNRRMKWKK (SEQ ID NO: 24)) or melittin (GIGAVLKVLTTGLPAL-ISWIKRKRQQ (SEQ ID NO: 25)). In certain aspects the CPP comprises the T1 (TKIESLKEHG (SEQ ID NO: 26)), T2 (TQIENLKEKG (SEQ ID NO: 27)), (AALEALAEAL-EALAEALEALAEAAAA (SEQ ID NO: 28)) or INF7 (GLFEAIEGFIENGWEGMIEGWYGCG (SEQ ID NO: 29)) CPP sequence.

III. Methods of Use

One aspect of the present invention relates to the use of peptides described herein and mutants, variants, analogs or derivatives thereof. Specifically, these methods relate to administering any one of the peptides as described herein or their pharmaceutically acceptable modifications as a dry powder to a subject, a composition for use in the treatment of treating or preventing a disease, injury or infection of the lungs (e.g., a fibrotic condition of the lungs), said composition comprising a polypeptide of the embodiments in pharmaceutically acceptable carrier.

A. Pharmaceutical Compositions

It is contemplated that the Cav-1 peptides provided herein can be administered systemically or locally to inhibit cell apoptosis and for the treatment and prevention of damage to lung tissues. They can be administered intravenously, subcutaneously, intramuscularly, intrathecally, and/or intraperitoneally. For example, a dry powder formulation can be administered by installation into a subject (e.g., subcutaneous installation) or may be reconstituted in a liquid prior to injection. In particular aspects, the peptides are delivered locally to the airway, such as administration of a dry powder formulation using a dry powder inhaler. They can be administered alone or in combination with anti-fibrotic compounds.

The Cav-1 peptide dry powder may be administered in combination, simultaneously or sequentially with at least one additional therapeutic (e.g., a therapeutic for treatment of lung fibrosis). The additional therapeutic may be an NSAID, steroid, DMARD, immunosuppressive, biologic response modulators, bronchodilator or antifibrotic agent such as pirfenedone, an agent whose antifibrotic mechanism of action is not fully understood but may involve blockade of TGF-beta, nintedanib, a broad tyrosine kinase blocker or any other antifibrotic agent. Suitable NSAIDS are selected from the non-selective COX-inhibitors acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, niflu-minic acid, tolfenamic acid, diflunisal, flufenisal, piroxicam, tenoxicam, lornoxicam and nimesulide and the pharmaceutically acceptable salts thereof, the selective COX 2-inhibitors meloxicam, celecoxib and rofecoxib and the pharmaceutically acceptable salts thereof. Suitable steroids are prednisone, prednisolone, methylprednisolone, dexamethasone, budenoside, fluocortolone and triamcinolone. Suitable DMARDs are sulfasalazine, olsalazine, chloroquin, gold derivatives (Auranofin), D-penicillamine and cytostatics such as methotrexate and cyclophosphamide. Suitable immunsuppressives are cyclosporine A and derivatives thereof, mycophenolatemofetil, FK 506, OKT-3, ATG, 15-desoxyspergualin, mizoribine, misoprostol, rapamycin, reflunomide and azathioprine. Suitable biologic response modifiers are interferon β, anti-TNF-α (Etanercept), IL-10, anti-CD3 or anti-CD25. Suitable bronchodilators are ipratropium bromide, oxytropiumbromide, tiotropiumbromide, epinephrinehydrochloride, salbutamole, terbutalinsulfate, fenoterolhydrobromide, salmeterole and formoterole. In such combinations each active ingredient can be administered (e.g., orally or by inhalation) either in accordance with its usual dosage range or a dose below its usual dosage range. The dosage for the combined NSAIDs, steroids, DMARDs, immunsuppressives and biologic response modifiers is appropriately 1/50 of the lowest dose normally recommended up to 1/1 of the normally recommended dosage, preferably 1/20 to 1/2 and more preferably 1/10 to 1/5. The normally recommended dose for the combined drug should be understood to be the dose disclosed for example in Rote Liste® 2002, Editio Cantor Verlag Aulendorf, Germany, or in Physician's Desk Reference.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more of the polypeptides of the embodiments or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one polypeptide of the embodiments isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet bioburden, sterility, pyrogenicity, general safety, and/or purity standards as required by the FDA Office of Biological Standards or other appropriate regulatory authority.

Certain embodiments of the present invention may comprise different types of carriers depending on whether it is to be administered in solid, liquid, or aerosol form, and whether it needs to be sterile for the route of administration, such as injection. The compositions can be administered intravenously, intrathecally, intradermally, transdermally, intrathecally, intraarterially, intraperitoneally, intranasally, intravaginally, intrarectally, intramuscularly, subcutaneously, mucosally, orally, topically, locally, by inhalation (e.g., inhalation of a nebulized formulation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). The choice of injection volume and needle size may be chosen by the person of ordinary skill in the art based on site of injection, syringeability and injectability, which includes considering the viscosity of the solution or suspension to be injected and drug concentration, pH, and osmolality. In some instances, the particle size of the active agent can be chosen in order to provide a desired rate of dissolution upon administration (e.g., by subcutaneous injection).

The peptides presented herein may be formulated into a composition in a free base, neutral, zwitterion or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier can comprise, in some aspects, aerosol, gas, liquid, semi-solid, i.e., pastes, or solid carriers. Except insofar as any conventional media, agent, diluent, or carrier is detrimental to the recipient or to the therapeutic effectiveness of a composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates or lyoprotectants, such as dextrose, mannose, galactose, fructose, lactose, sucrose, maltose, sorbitol, mannitol, etc.

In some aspects, a pharmaceutical formulation comprises one or more surfactant. Surfactants used in accordance with the disclosed methods include ionic and non-ionic surfactants. Representative non-ionic surfactants include polysorbates such as TWEEN®-20 and TWEEN-80® surfactants (ICI Americas Inc. of Bridgewater, N.J.); poloxamers (e.g., poloxamer 188); TRITON® surfactants (Sigma of St. Louis, Mo.); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or (e.g., lauroamidopropyl); myristamidopropyl-, palmidopropyl-, or isostearamidopropyl-dimethylamine; sodium methyl cocoyl-, or disodium methyl oleyl-taurate; MONAQUAT™ surfactants (Mona Industries Inc. of Paterson, N.J.); polyethyl glycol; polypropyl glycol; block copolymers of ethylene and propylene glycol such as PLURONIC® surfactants (BASF of Mt. Olive, N.J.); oligo (ethylene oxide) alkyl ethers; alkyl (thio) glucosides, alkyl maltosides; and phospholipids. For example, the surfactant can be present in a formulation in an amount from about 0.01% to about 5% (weight of surfactant relative to total weight of other solid components of the formulation; "w/w"), from about 0.03% to about 0.5% (w/w), from about 0.05% to about 0.5% (w/w), or from about 0.1% to about 0.5% (w/w). However, in further aspects, a pharmaceutical formulation of the embodiments is essentially free of non-ionic surfactants or essentially free of all surfactants.

With respect to the therapeutic methods of the invention, it is not intended that the administration of the one or more peptides as disclosed herein or a mutant, variant, analog or derivative thereof and be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat the inflammation-related disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the one or more polypeptides as disclosed herein or a mutant, variant, analog or derivative thereof may be provided at a dose of 0.0001, 0.01, 0.01 0.1, 1, 5, 10, 25, 50, 100, 500, or 1,000 mg/kg or g/kg. Effective doses may be extrapolated from dose-response curves derived from in vitro or animal model test bioassays or systems.

Dosages for a particular patient or subject can be determined by one of ordinary skill in the art using conventional considerations, (e.g., by means of an appropriate, conventional pharmacological protocol). A physician may, for example, prescribe a relatively low dose at first, subsequently increasing the dose until an appropriate response is obtained. The dose administered to a patient is sufficient to affect a beneficial therapeutic response in the patient over time, or, e.g., to reduce symptoms, or other appropriate activity, depending on the application. The dose is determined by the efficacy of the particular formulation, and the activity, stability or serum half-life of the one or more polypeptides as disclosed herein or a mutant, variant, analog or derivative thereof and the condition of the patient, as well as the body weight or surface area of the patient to be treated.

In some aspects, a subject is given a single dose, given once daily for treating a subject, preferably a mammal, more preferably human who his suffering from or susceptible to pulmonary fibrosis resulting therefrom is between about 0.2 mg/kg and about 250 mg/kg, such as between about 10 mg/kg and about 50 mg/kg, for example, via instillation (by inhalation). Such a dose can be administered daily for anywhere from about 3 days to one or more weeks. Chronic administration is also possible, though the dose may need to be adjusted downward as is well-understood in the art. The foregoing ranges are, however, suggestive, as the number of variables in an individual treatment regime is large, and considerable excursions from these preferred values are expected.

For continuous administration, e.g., by a pump system such as an osmotic pump that was used in some of the experiments described below, a total dosage for a time course of about 1-2 weeks is preferably in the range of 1 mg/kg to 1 g/kg, preferably 20-300 mg/kg, more preferably 50-200 mg/kg. After such a continuous dosing regimen, the total concentration of the active compound is preferably in the range of about 0.5 to about 50 µM, preferably about 1 to about 10 µM.

An effective concentration of the active compound for inhibiting or preventing apoptosis in vitro is in the range of about 0.5 nM to about 100 nM, more preferably from about 2 nM to about 20 nM. Effective doses and optimal dose ranges may be determined in vitro using the methods described herein.

B. Dry Powder Particle Size Reduction and Dry Powder Inhalation Devices.

The particle sizes of the formulations can be reduced by any suitable method, including but not limited to milling, grinding, thin film freezing, spray drying, or crushing. Milling may be performed by any method known in the art, such as by air jet mill, ball mill, wet mill, media mill, high pressure homogenization, or cryogenic mill.

Peptide stability following particle size reduction can be assessed using known techniques in the art, including size exclusion chromatography; electrophoretic techniques; HPLC; mass spectrometry; spectroscopic techniques such as UV spectroscopy and circular dichroism spectroscopy, and activity (measured in vitro or in vivo). To perform in vitro assays of protein stability, an aerosol composition can be collected and then distilled or absorbed onto a filter. To perform in vivo assays, or for pulmonary administration of a composition to a subject, a device for dry powder dispersion is adapted for inhalation by the subject. For example, protein stability can be assessed by determining the level of protein aggregation. Preferably, a dry powder composition of the invention is substantially free of protein aggregates. The presence of soluble aggregates can be determined qualitatively using dynamic light scattering (DLS) (Dyna-Pro-801TC, Protein Solutions Inc. of Charlottesville, Va.) and/or by UV spectrophotometry.

In some embodiments, treatment of a patient with milled CSP7 may comprise modulated drug release. In some embodiments, milled CS7 may be formulated for slow- or delayed-release. In some embodiments, milled CSP7 may be formulated for fast-release. In further embodiments, milled CSP7 may be formulated for both slow and fast release (i.e., dual release profile).

In some embodiments, the present disclosure provides methods for the administration of the inhalable CSP7 composition provided herein. Administration may be, but is not limited, to inhalation of milled CSP7 using an inhaler. In some embodiments, an inhaler is a passive dry powder inhaler (DPI), such as a Plastiape RSO1 monodose DPI. In a dry powder inhaler, dry powder is stored in a reservoir and is delivered to the lungs by inhalation without the use of propellants.

In some embodiments, an inhaler is a single-dose DPI, such as a DoseOne™ Spinhaler, Rotohaler®, Aerolizer®, or Handihaler. In some embodiments, an inhaler is a multidose DPI, such as a Plastiape RS02, Turbuhaler®, Twisthaler™, Diskhaler®, Diskus®, or Ellipta™. In some embodiments, an inhaler is a plurimonodose DPI for the concurrent delivery of single doses of multiple medications, such as a Plastiape RS04 plurimonodose DPI. Typically, dry powder inhalers have medication stored in an internal reservoir, and medication is delivered by inhalation with or without the use of propellants. Other types of dry powder inhalers have medication in pre-divided doses stored in a capsule (e.g., cellulose or gelatin base) or foil pouch, each of which is punctured by the device to release the dose to the patient. Dry powder inhalers may require an inspiratory flow rate greater than 30 L/min for effective delivery, such as between about 30-120 L/min. In some embodiments, efficient aerosolization of milled CSP7 is independent of inspiratory force. In some embodiments, the dry powder inhaler has a flow resistance of between 0.01 kPa$^{0.5}$ min/L and 0.05 kPa$^{0.5}$ min/L, such as between 0.02 kPa$^{0.5}$ min/L and 0.04 kPa$^{0.5}$ min/L. The dry powder inhaler (e.g., high resistance, low resistance, passive, active) is chosen based on the patient population and their inspiratory capabilities.

In some embodiments, the inhaler may be a metered dose inhaler. Metered dose inhalers deliver a defined amount of medication to the lungs in a short burst of aerosolized medicine aided by the use of propellants. Metered dose inhalers comprise three major parts: a canister, a metering valve, and an actuator, and may utilize a spacer device to de-accelerate the emitted particles and facilitate inhalation of the aerosolized cloud by the patient. The medication formulation, including propellants and any required excipients, are stored in the canister. The metering valve allows a defined quantity of the medication formulation to be dispensed. The actuator of the metered dose inhaler, or mouthpiece, contains the mating discharge nozzle and typically includes a dust cap to prevent contamination. The required inspiratory flow rate required for the use of a metered dose inhaler may be less than 90 L/min, such as between about 15-90 L/min, preferably about 30 L/min. In some embodiments, efficient aerosolization of milled CSP7 is independent of inspiratory force.

In some embodiments, an inhaler is a nebulizer. A nebulizer is used to deliver medication in the form of an aerosolized mist inhaled into the lungs. The medication formulation is aerosolized by compressed gas, or by ultrasonic waves. A jet nebulizer is connected to a compressor. The compressor emits compressed gas through a liquid medication formulation at a high velocity, causing the medication formulation to aerosolize. Aerosolized medication is then inhaled by the patient. An ultrasonic wave nebulizer generates a high frequency ultrasonic wave, causing the vibration of an internal element in contact with a liquid reservoir of the medication formulation, which causes the medication formulation to aerosolize. Aerosolized medication is then inhaled by the patient. A nebulizer may utilize a flow rate of between about 3-12 L/min, such as about 6 L/min. In some examples, the milled active (e.g., CSP7) can be suspended in a pharmaceutically acceptable liquid carrier vehicle and administered by nebulization (e.g., air jet nebulization). In further aspects, a composition of the embodiments can be administered by a vaporization method (e.g., rapid vaporization) such as by a e-cigarette device.

In some embodiments, the composition may be administered on a routine schedule. As used herein, a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In some embodiments, a peptide (e.g., CSP7) is administered once per day. In preferred embodiments, a peptide is administered less than once per day, such as every other day, every third day, or once per week. In some embodiments, a complete dose of a peptide of the embodiments (e.g., CSP7) is between 1-100 mg, such as 20-100, 50-100, 10-20, 20-40, 50-70, or 80-90 mg.

In some embodiments, a peptide of the embodiments (e.g., CSP7) may be provided in a unit dosage form (e.g., pre-divided dose), such as in a capsule, blister or a cartridge, wherein the unit dose comprises at least 1 mg of a peptide, such as at least 5 mg, 10 mg, 15 mg or 20 mg of a peptide of the embodiments (e.g., CSP7) per dose. In some aspects, the unit dose is 1-10 mg (e.g., about 5 mg) of a peptide. In particular aspects, the unit dosage form does not comprise the administration or addition of any excipient and is merely used to hold the powder for inhalation (i.e., the capsule, blister, or cartridge is not administered). In some aspects, more than one of the unit dose forms in administered to a subject. For example, in the case of a dry powder inhaler, peptides of the embodiments may be provided in unit dose capsules and more than one unit dose capsules (e.g., 3-4) can be administered to a subject by inhalation. In some embodiments, peptides such as CSP7 may be administered in a high emitted dose, such as at least 10 mg, preferably at least 15 mg, even more preferably 20 mg. In some embodiments, administration of milled a peptide of the embodiments (e.g., CSP7) results in a high fine particle dose into the deep lung such as greater than 5 mg. Preferably, the fine particle dose into the deep lung is at least 10 mg, even more preferably at least 15 mg. In some aspects the particle dose is produced from 1, 2, 3, 4 or 5 or more capsules comprising doses of a peptide of the embodiments (e.g., CSP7). In some aspects, the fine particle dose is at least, 50%, such as at least 60, 65, 70, 75, or 80% of the emitted dose.

In some embodiments, changes in inhalation pressure drop result in a change in emitted dose. In some embodiments, changes in inhalation pressure of 3 kPa, such as from 4 kPa to 1 kPa, result in a reduction of emitted dose of less than 25%, such as 24%, 23%, 22%, 21%, 20%, 19%, 18%, 17%, 16%, 15%, 14%, 13%, 12%, 11%, 10%, 9%, 8%, 7%, 6%, 5% or less. In some embodiments, changes in inhalation pressure result in a change in fine particle dose. In some embodiments, changes in inhalation pressure of 3 kPa, such as from 4 kPa to 1 kPa result in a reduction of fine particle dose of less than 15%, such as 14%, 13%, 12%, 11%, 10%, 9%, 8%, 7%, 6%, 5% or less.

IV. Pulmonary Conditions for Treatment

Peptides of the present invention can be used to treat a variety of pulmonary conditions. Pulmonary conditions for treatment may be acute or chronic. Acute pulmonary conditions may be acute lung injury, infection or chemical-induced. Chronic pulmonary conditions maybe the result of injury, infection or disease.

A. Lung Injuries

In some aspects, the subject has an acute lung injury (ALI) or infection or a chemical-induced lung injury. In specific aspects, the subject has plastic bronchitis, asthma, chronic obstructive airway/pulmonary (COPD), acute respiratory distress syndrome (ARDS) inhalational smoke induced acute lung injury (ISALI), bronchiectasis, inhalational toxin-induced airway disease (e.g., chlorine or other induced airways disease), exposure to mustard gas, exposure to particulate matter (e.g., silica dust), bronchiolitis obliterans, bronchiolitis obliterans organizing pneumonia, collagen vascular lung disease (e.g., from lupus, scleroderma or mixed connective tissue disease), interstitial lung disease (e.g., idiopathic pulmonary fibrosis or sarcoidosis), drug induced lung disease and accelerated pulmonary fibrosis (e.g., that occurs after acute lung injury including ARDS). Lung diseases including chronic obstructive pulmonary disease, asthma, infections, as well as acute and chronic lung injury leading to fibrosis, constitute the third leading cause of death world-wide (Murray et al., 1997; Rabe et al., 2007; Tsushima et al., 2009). Acute lung injury (ALI) is a serious medical problem amongst American military personnel. ALI during combat can result from very broad etiologies.

ALI from inhalational injury has been treated with inhaled anticoagulants, steroids, beta-agonists, high frequency ventilation, and extra-corporeal membrane oxygenation, with variable and, in general, suboptimal results. No effective preventive measures are available other than barriers with respiratory masks. The management of ARDS has progressed significantly but remains largely supportive with watchful waiting for endogenous healing mechanisms to take effect; and in-hospital mortality remains above 40% (Matthay et al., 2012). Survivors of ALI often suffer chronic respiratory disability with reduced quality of life. Any modalities that can accelerate recovery and/or prevent later complications such as chronic respiratory insufficiency and pulmonary fibrosis will be highly desirable. There is a dire need to improve the early diagnosis and much more importantly, prevention and therapy of ALI. The pathophysiology of ALI from direct inhalational lung injury or ARDS consequent to systemic illness is extremely complex and heterogeneous, encompassing systemic as well as local cardiopulmonary factors such as increased membrane permeability, influx of inflammatory cytokines, oxidative cellular damage, compartmental fluid shifts, deranged ion channels, and many others (Matthay et al., 2012). Clearly, novel treatments are needed for treating and preventing lung disorders such as ALI.

In some embodiments, there is provided a method of treating or preventing acute lung injury, lung infection or lung disease in a subject comprising administering to the subject an effective amount of peptide comprising the amino acid sequence of FTTFTVT (SEQ ID NO: 2) or a variant thereof, wherein the peptide maintains the biological activity of caveolin-1 (Cav-1). In some aspects, a method of administering a pharmaceutical formulation of the peptides comprises dry powder inhalation. In particular aspects, the subject is a human.

B. Lung Diseases

Lung diseases include pulmonary fibrosis, pulmonary inflammation, idiopathic pulmonary fibrosis, cystic fibrosis, chronic obstructive pulmonary disease (COPD), bronchitis, bronchiolitis, bronchiolitis obliterans, asthma, and pulmonary infections, as well as acute and chronic lung injury leading to fibrosis (Murray et al., 1997; Rabe et al., 2007; Tsushima et al., 2009). These diseases constitute the third leading cause of death world-wide.

Cystic fibrosis is an inherited disease of the exocrine glands and exocrine sweat glands which primarily affects the digestive and respiratory systems. This disease usually characterized by chronic respiratory infections, pancreatic insufficiency, abnormally viscid mucous secretions and premature death. Cystic fibrosis (CF) is characterized by progressive airflow obstruction. Subsets of individuals with CF also develop airway hyper-responsiveness to inhaled cholinergic agonists (Weinberger, 2002 and Mitchell et al., 1978) and reversibility of airflow limitation in response to bronchodilators (van Haren et al., 1991 and van Haren et al., 1992). The presence of bronchial hyper-responsiveness and airway obstruction suggest a possible shared etiology of disease between CF and other diseases of airway narrowing such as asthma or chronic obstructive pulmonary disease (COPD) where airway smooth muscle dysfunction is thought to contribute to the disease processes.

A pulmonary infection may be a bacterial infection. The infectious bacteria may be *Pseudomonas aeruginosa, Bacillus anthraces, Listeria monocytogenes, Staphylococcus aureus, Salmenellosis, Yersina pestis, Mycobacterium leprae, M. africanum, M. asiaticum, M. aviuin-intracellulaire, M. chelonei abscessus, M. fallax, M. fortuitum, M kansasii, M leprae, M. malmoense, M. shimoidei, M. simiae, M. szulgai, M. xenopi, M. tuberculosis, Brucella melitensis, Brucella suis, Brucella abortus, Brucella canis, Legionella pneumonophilia, Francisella tularensis, Pneurnocystis carinii, mycoplasma,* or *Burkholderia cepacia*. The bacterial infection may result in pneumonia.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S., accounting for 122,283 deaths in 2003. The cost to the USA for COPD was approximately $20.9 billion in direct health care expenditures in 2003. Chronic bronchitis is inflammation of the bronchial airways. The bronchial airways connect the trachea with the lungs. When inflamed, the bronchial tubes secrete mucus, causing a chronic cough.

In emphysema, the alveolar sacs are overinflated as a result of damage to the elastin skeleton of the lung. Inflammatory cells in emphysematous lung release elastase enzymes, which degrade or damage elastin fibers within the lung matrix. Emphysema has a number of causes, including smoking, exposure to environmental pollutants, alpha-one antitrypsin deficiency, and aging.

Bronchiolitis is most commonly caused by viral lower respiratory tract infections, and primarily characterized by acute inflammation, edema, necrosis of epithelial cells lining small airways, and increased mucus production (Ralston et al., 2014). Signs and symptoms typically begin with rhinitis and cough, which may progress to tachypnea, wheezing, rales, use of accessory muscles, and/or nasal flaring.

Bronchiolitis obliterans is a progressive airflow reduction as a result of abnormal remodeling of the small airways in the lungs (Meyer et al., 2014). Bronchiolitis obliterans syndrome is a major complication of lung transplantations and is often used to describe a delayed allograft dysfunction that results in persistent decline in forced expiratory volume and force that is not caused by other known causes (Meyer et al., 2014).

The term "asthma" may refer to acute asthma, chronic asthma, intermittent asthma, mild persistent asthma, moderate persistent asthma, severe persistent asthma, chronic persistent asthma, mild to moderate asthma, mild to moderate persistent asthma, mild to moderate chronic persistent asthma, allergic (extrinsic) asthma, non-allergic (intrinsic) asthma, nocturnal asthma, bronchial asthma, exercise induced asthma, occupational asthma, seasonal asthma, silent asthma, gastroesophageal asthma, idiopathic asthma and cough variant asthma. During asthma, the airways are persistently inflamed and may occasionally spasm.

In some embodiments, there is provided a method of treating or preventing lung infection or lung disease in a subject comprising administering to the subject an effective amount of a dry powder peptide comprising the amino acid sequence of FTTFTVT (SEQ ID NO: 2; referred to herein as CSP7), wherein the dry powder peptide maintains the biological activity of caveolin-1 (Cav-1). In some aspects, a method of administering a pharmaceutical formulation of the embodiments comprises dry powder inhalation of the peptide. In particular aspects, the subject is a human.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Methods and Materials

Preparation of dry powder peptides. CSP7 peptide (SEQ ID NO: 2), lot #: AHF66//470103 was synthesized by Polypeptide Laboratories (San Diego, USA).

Manufacture of CSP7 mixes and spray drying. CSP7 formulations containing either CSP7 alone (CSP7), or a 75%/25% mix of CSP7/Leucine, CSP7/Trehalose, or CSP7/Sodium Citrate, or a 75%/15%/10% mix of CSP7/Leucine/Trehalose were prepared in pH 10 water (adjusted with NH$_4$OH) and spray dried using a BLD-35 with 2" cyclone.

Reduction of dry powder CSP7 particle size by Thin Film Freezing (TFF). 0.3 mg/ml CSP7 bulk powder and 0.9 mg/ml Mannitol (mass ratio 1:3) were dissolved in 10 mM Tris buffer, and the pH was adjusted to 8.05. The solution was then filtered with a 0.45 µm membrane and dropped onto a rolling chamber filled with liquid nitrogen. The metered freezing temperature was between −55 and −65° C. The frozen flakes were then lyophilized in a VirTis AdVantage Freeze Dryer (VirTis Company Inc., NY, US). The lyophilization conditions were as follows: equilibration: hold at −55° C., 100 mTorr for 30 min; primary drying: ramp temperature up to −30° C., 100 mTorr over 250 min; hold at −30° C., 100 mTorr for 660 min; secondary drying: ramp to 30° C., 100 mTorr over 720 min; and hold at 30° C., 100 mTorr for 240 min. The TFF processed sample is referred to as batch 171014.

Reduction of dry powder CSP7 particle size by Cryogenic Milling. One gram of CSP7 bulk powder is added into a small cryomill tube and then loaded in 6870 Freeze/Mill (SPEX Certiprep™, NJ, USA). Milling was done in 5 cycles, a 10 minute precool, and each cycle having a 5 minute run time at 10 CPS followed by a cooling of 2 minutes. Milled sample was retrieved and weighed, and yield was calculated to be 73.5% based on retrieved weight over loaded weight.

Reducing particle size of CSP7 powder by Ball Mill (BM). CSP7 bulk powder was suspended in its antisolvent, ethanol (anhydrous), to a concentration of 1 mg/ml. Approximately half of the solvent volume of Zirconium balls (2 mm) were added to the suspension. The suspension was then loaded into an 8000M Mixer/Mill (SPEX SamplePrep, NJ, USA) to mill. Samples were collected from the milling process to test at 5 min, 10 min, and 30 min, respectively.

Reduction of particle size of CSP7 powder using a Rotor-stator. CSP7 bulk powder was dispersed into ethanol to a concentration of 1 mg/ml. The tip (5 mm*75 mm flat bottom) of the Rotor-stator was submerged in the suspension and homogenization was performed to reduce the particle size.

High Performance Liquid Chromatography Analysis. Samples were dissolved in 20 mM Tris buffer (pH 10.3), and run on a Phenomenex Luna® C18(2) liquid chromatography column with 5 μm particle size and 100 Å pore size. The Phenomenex Security Guard Guard Cartridge Kit was used as a guard column. Mobile phase A was $H_2O$+0.1% (v/v) Trifluoroacetic acid (TFA), and mobile phase B was 80% acetonitrile+20% $H_2O$+0.09% (v/v) TFA. The sample was injected in a volume of 20 μL. The samples were run for 25 min each, and the column was kept at 25° C., at a flow rate of 1 ml/min. The samples were detected at a wavelength of 220 nm. The buffer gradient was set to the conditions specified in Table 2.

TABLE 2

| Materials, conditions, and methods for HPLC | |
|---|---|
| Separation Column | Phenomenex Luna ® 5 μm C18(2) 100 Å, LC Column 150 × 4.6 mm |
| Guard Column | Phenomenex Security Guard Guard Catridge Kit |
| Mobil Phase A | $H_2O$ + 0.1% Trifluoroacetic acid (TFA) |
| Mobil Phase B | 80% Acetonitrile + 20% $H_2O$ + 0.09% TFA |

TABLE 2-continued

| Materials, conditions, and methods for HPLC | | | |
|---|---|---|---|
| Injection Volume | 20 μL | | |
| Run Time | 25 min | | |
| Column Temp. | 25° C. | | |
| Flow | 1 ml/min | | |
| Wavelength | 220 nm | | |
| Gradient | Time (min) | A % | B % |
| | 0 | 75 | 25 |
| | 20 | 65 | 35 |
| | 21 | 75 | 25 |
| | 25 | 75 | 25 |

Determination of aerodynamic particle size distribution of milled CSP7 bulk powder. Around 3.5 mg of milled CSP7 powder was manually filled into size 3 HPMC capsules (Capsugel, Peapack, N.J.). CSP7 capsules were then aerosolized using a RS01 Monodose Dry Powder Inhaler (high resistance) and aerodynamic particle size distribution was measured by a Next Generation Impactor (NGI, MSP Corp., Shoreview, Minn.). Aerosols were produced over 4 s at an air flow rate of 60 L/min for the inhaler to achieve an inhalation volume of 4 L and 4 kPa pressure drop across the device. Before each run, NGI collection surfaces were coated with 5% (v/v) polysorbate 20 in methanol. One capsule was shot for each run and each sample was ran in triplicate repetitions (three capsules). After aerosolization, all collection surfaces were rinsed with specific volumes of 20 mM Tris buffer (pH 10.3) to collect the drug. Powders deposited in the capsule, device, adaptor, throat, pre-separator, and stages 1-MOC were extracted respectively.

For each test, delivered dose is defined as the mass of CSP7 that entered the NGI. Geometric standard deviation (GSD), mass median aerodynamic diameter (MMAD) and fine particle fraction % (FPF %) are calculated and analyzed with Copley Inhaler Testing Data Analysis Software (CITDAS, Copley Scientific, Nottingham UK), based on the doses deposited on stages 1-MOC of NGI. The FPF is defined as the mass fraction of particles less than 5.0 μm with the delivered dose.

Preparation and lysis of lung tissues. Female mice, ages 6-8 weeks are ordered from Jackson Laboratories, stock: 000664 C57BL/6J are cared for and housed according to IACUC guidelines. The following week, mice are weighed, anesthetized with an IP injection of 80 mg/kg Ketamine & 6 mg/kg Xylazine (approx. 115 ul/mouse) and subjected to a single intratracheal installation of bleomycin. Briefly, a 26G plastic catheter is inserted into the trachea and mice receive, via pipette, 2×20 ul installations (spaced 30 s apart to allow clearance from the airways) of 0.8 U/kg bleomycin (Biotang, Cat #RB003). Controls receive the same volume of saline only. Weight is tracked (approximately 10% weight loss occurs in injured animals) and animals are subjected to a dry powder inhalation protocol (CH technologies) daily for one week. The dry powder dosing was based on the minimum efficacious dose of previous nebulization formulation which was estimated to be a lung delivered dose of 0.7 mcg/animal (Tepper et al., 2016, incorporated herein by reference). In summary, an exposure time of 12 min/day matched a '1×' dose and a '5×' dose designated a 60 min/day treatment equivalent to 3.5 mcg/animal. Animals were exposed for seven consecutive days (d14-20; during the fibrotic phase of bleomycin injury) and sacrificed 24 hrs following the last dose lethal dose of heparinized ketamine/xyalizine cocktail (25% heparin). A subset of whole lungs were harvested for histology. Briefly, a transcardiac perfusion with 10 mls of saline clears the blood from the lung. Then, the lungs were inflated with saline for 1 min, followed by 4% PFA for 1 min from 20 cm above the dissection stage. The trachea was tied off and the lung was excised, fixed, embedded and sectioned to 4 microns to achieve visualization of the maximum surface area, and stained with hematoxylin and eosin. Images were captured with Aperio AT2 high volume, digital whole slide scanner and lungs were scored for fibrotic injury according to modified Ashcroft scoring protocol (Hubner et al., 2008, incorporated herein by reference). For molecular analyses, whole lungs were homogenized in RIPA buffer and protease inhibitors (Santa Cruz) as well as 1% DTT (to inhibit RNAses), homogenized in parallel at 4C (Precellys Evolution, Bertin Instruments) and processed for downstream assays. Collagen content of lung homogenate was assayed according using Total Collagen Assay (Quickzyme) using the collagen standard provided by the manufacturer and according to manufacturer's instructions. The colormetric assay was read on a microplate reader (FilterMax F5, Molecular Devices, 580 nm). In addition, RNA was extracted from homogenate (Zymogen Research) and reverse transcribed to cDNA (Qiagen, QuantiNova Reverse Transcription 205413). Results of these studies are show in FIGS. 29-32.

Homogenization buffer for 28 samples was prepared by adding 224 µL of cocktail inhibitor, 224 µL of NaOV4, 224 µL of PMSF, and 0.22 g of DTT to 22.4 mL of RIPA buffer. 800 µL of homogenization buffer was added per sample. Samples were homogenized using the Precellys Evolution with CK28 beads. The homogenization protocol used was for hard tissue and performed twice at 4° C. for each sample. The homogenized samples were then aliquoted out, with 400 µL stored for BCA concentration determination and protein assays, 200 µL for RNA isolation, and 200 µL for the collagen assay.

Collagen assay. Collagen standard was prepared for use by adding 125 µL of the Quickzyme collagen standard to 125 µL of 12 M HCL, and 200 µL of each sample to 200 µL of 12 M HCl. The samples and standard were incubated at 95° C. for 20 hours, and vortex briefly after 20 minutes. Following incubation, samples were centrifuged for 10 minutes at 13,000×g. The standard was prepared according to the manufacturer's instructions (Quickzyme). 100 µL of each sample was then diluted into 50 µL of water. 10 µL of each diluted sample was then further diluted into 100 µL of 4M HCl. Duplicates of the standards and each of the samples were pipetted into plates. 75 µL of assay buffer was added to each well, and the plate was covered before shaking for 20 minutes. 75 µL of detection reagent mix was added per well, and the plate was mixed before incubating at 60° C. for one hour. Plates were then read as indicated above.

RNA isolation. RNA isolation was performed using the Qiagen RNeasy kit, according to the manufacturers instructions. Briefly 25 µL of RLT buffer and 75 µL of 70% ethanol were added to 50 µL of sample in RIPA buffer, yielding a total of 150 µL of starting material. 50 µL of the starting material for each sample was then added to 50 µL of RNase free water. Then, 350 µL of buffer RLT was added, and the samples were mixed well. 250 µL of 95-100% ethanol were then added to each, and the samples were mixed again. 700 µL of each sample were then added to their respective spine columns and centrifuged at 8000×g, and the flowthrough was discarded. 500 µL of RPE was added to each column, and the columns were centrifuged again. 500 µL of RPE was added again, and this time the samples were centrifuged for 2 min at 8000×g. Samples were transferred to a new microcentrifuge tube, and RNA was eluted with 40 µL of RNase free water by centrifugation for 1 min at 8000×g. Samples were quantified by nanodrop and analyzed as described above.

Example 2—Characterization of CSP7 Bulk Powder

Scanning Electron Microscopy. Bulk powder samples of CSP7 were sputtered on the sample tray and spread by blowing compressed nitrogen. Samples were imaged by scanning electron microscopy (FIG. 1). SEM indicates the existence of large (>5 µm) particles. Further, most of the particles appeared to be large (>5 µm), and thus out of the respirable range.

CSP7 Particle Size Evaluation. Particle sizes were examined using Spraytec laser diffraction and Sympatec laser diffraction instrument HELOS-R system, equipped with solid or wet dispersion attachment, to determine whether bulk powder is within the respirable range. The size of CSP7 bulk powder particles was determined to be larger than the respirable particle size using the dry dispersion method. Table 3 shows the particle sizes for the particles evaluated to be at Dv 10, Dv 50 (median), and Dv 90 within the distribution. As can be seen in Table 3, greater than 50% of all CSP7 particles analyzed had a particle size of 5.3 µm or larger, which is larger than the respirable range.

TABLE 3

Particle size of CSP7 bulk powder by Sympatec laser diffraction dry dispersion

| Dv 10 (µm) | Dv 50 (µm) | Dv 90 (µm) |
|---|---|---|
| 1.4 ± 0.0 | 5.3 ± 0.0 | 22.0 ± 1.7 |

The particle sizes were next determined by Sympatec laser diffraction by a wet dispersion method. CSP7 was dissolved in ethanol +0.05% Tween 80 as dispersion medium and sonicated 10 min. The results of the size determination of CSP7 particles using wet dispersion are shown in Table 4. As shown in Table 4, the average particle size (Dv 50) of the wet dispersion particles was 29.0±0.8, far outside of the respirable range.

TABLE 4

Particle size of CSP7 bulk powder by Sympatec laser diffraction wet dispersion

| Dv 10 (µm) | Dv 50 (µm) | Dv 90 (µm) |
|---|---|---|
| 7.2 ± 0.1 | 29.0 ± 0.8 | 63.9 ± 3.8 |

Average particle size was further evaluated using the Spraytec laser diffraction instrument, again using a dry dispersion method. The CSP7 bulk powder was dispersed at 40 PSI, and again the average particle size (8.6±1.5 µm) was above the respirable range (Table 5).

TABLE 5

Particle size of CSP7 bulk powder by Spraytec laser diffraction dry dispersion

| Dv 10 (µm) | Dv 50 (µm) | Dv 90 (µm) | % V < 5 µm % |
|---|---|---|---|
| 1.7 ± 0.2 | 29.0 ± 0.8 | 63.9 ± 3.8 | 34.5 ± 4.1 |

The percentage of the dry powder particles found to be smaller than 5 µm was found to be only 34.5±4.1%. Given that each of the laser diffraction methods found the majority of the bulk powder to have a particle size outside the respirable range, any dry powder used for treatment would need to be processed in some way to reduce particle size.

Figure 2:
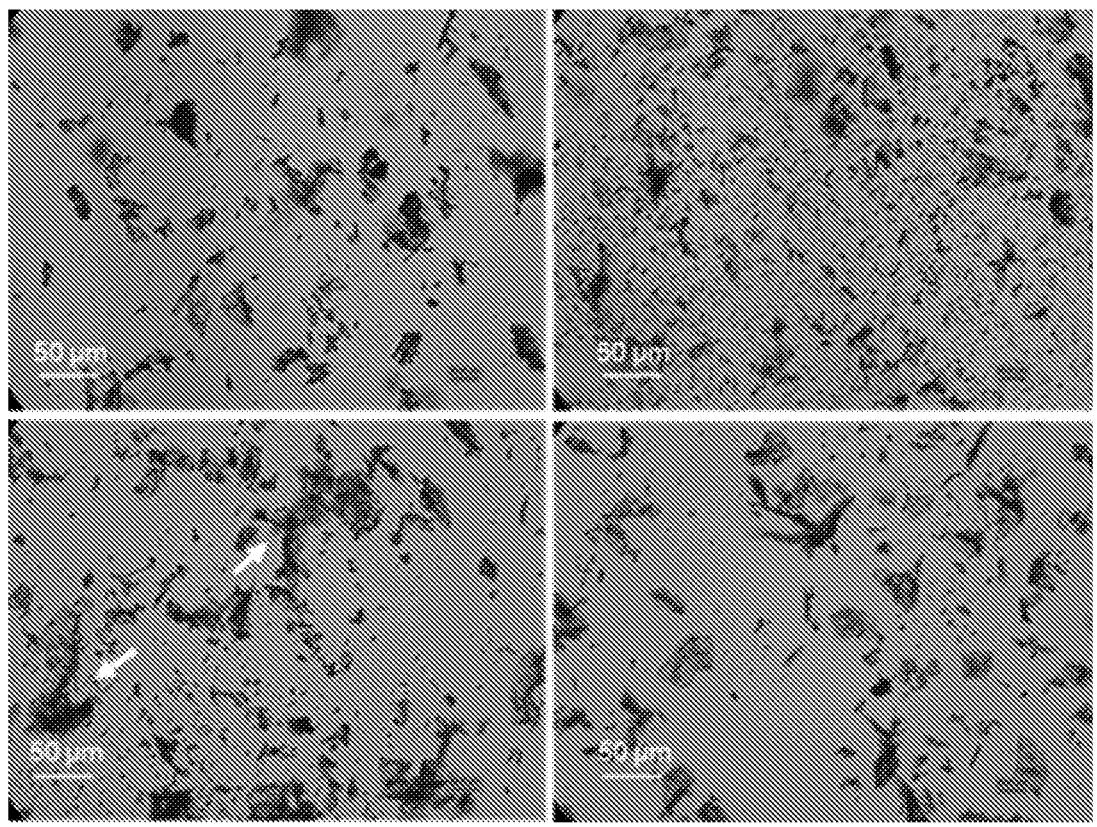
FIG. 2: Optical Microscopy Images of CSP7 Bulk Powder. Powder samples were sputtered on the glass slides and viewed using a Leica optical microscope (Leica CTR6500). Scale bars are indicated in the lower left hand corner of each image. Arrows point to agglomerated particles of neat CSP7 powder.
Figure 3:
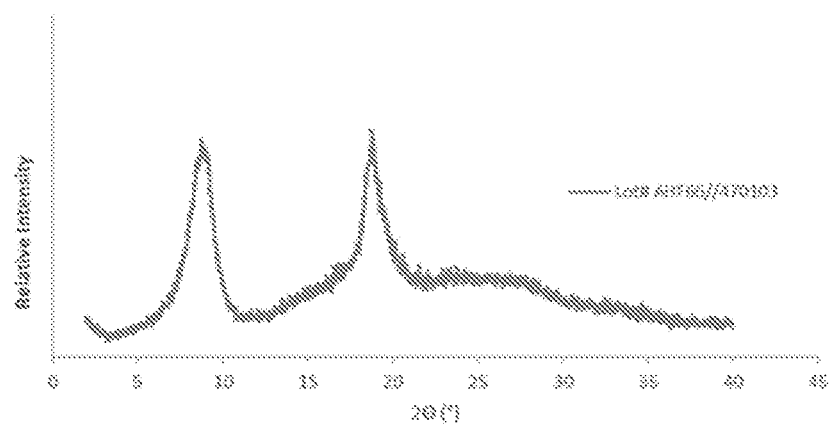
FIG. 3: X-ray Powder Diffraction of CSP7 Bulk Powder Particles. CSP7 bulk powder particles were evaluated using X-ray powder diffraction to determine the crystallinity. Powder is measured from 2 to 40 2θ degrees using a step size of 0.025 2θ degrees and a speed of 2 degree/min.
Figure 4:
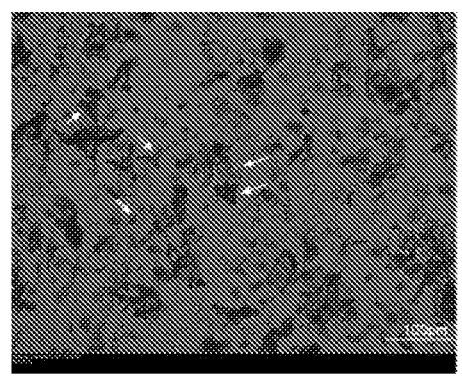
FIG. 4: Polarized Light Microscopy of CSP7 Bulk Powder. Crystallinity was evaluated by polarized light microscopy. Pictured is a representative image. White arrows point to crystalline regions.

Morphology of Bulk CSP7 powder. Bulk powder CSP7 samples were sputtered onto glass slides and viewed by optical microscopy (FIG. 2). Optical microscopy confirmed the SEM, indicating the presence of large (>5 um) particles. Optical microscopy also shows the presence of particle agglomerates, visible in FIG. 2 by arrows.

Determination of Crystallinity of CSP7 Bulk Powder Particles. CSP7 bulk powder particles were evaluated using X-ray powder diffraction (FIG. 3). It was found that neat CSP7 exhibits some crystallinity by X-ray powder diffraction (FIG. 3). To confirm the X-ray diffraction results, crystallinity was evaluated by polarized light microscopy (FIG. 4). As can be seen in FIG. 4, there is crystalline CSP7 present in the bulk CSP7 powder, and certain typical crystalline forms are indicated by white arrows in the image.

Thermo-analysis of CSP7 Bulk Powder. Differential Scanning calorimetry was used to determine the melting point of neat CSP7 (FIG. 5). As determined by DSC, the melting point of CSP7 was determined to be 211.03° C. (FIG. 5). Analysis was continued using Thermogravimetric analysis (TGA) (FIG. 6). The TGA indicates that the weight of neat CSP7 starts dramatically decreasing above 216° C. (FIG. 6).

Moisture Content of CSP7 Bulk Powder. The moisture content of bulk powder CSP7 was evaluated by Karl Fischer-Volumetric (KF-V) titration using a Mettler Toledo Karl Fischer Titrator, and performed in triplicate. Table 6 shows the moisture content of each test, and the average moisture content from the 3 tests.

TABLE 6

Moisture content of CSP7 bulk powder.

| Test | Moisture Content |
|---|---|
| 1 | 2.9% |
| 2 | 3.0% |
| 3 | 3.1% |
| Average | 3.0% |

Next, the moisture sorption of CSP7 bulk powder was analyzed using dynamic vapor sorption, DVS (FIG. 7). The CSP7 sample was run for a full sorption/desorption cycle, and the sample was found to have a 6.32% moisture desorption in relative humidity of zero. The mass change was found to be 10.54% when the relative humidity is 90% (FIG. 7).

Example 3—Characterization of CSP7 Powders Following Particle Size Reduction

Particle Size Reduction of CSP7 Powder. In order to effectively inhale and deposit a powder into the lungs, the particle size should generally have a mass median aerodynamic diameter of less than about 5 μm. A variety of techniques were performed to reduce particle size of the neat material, including air jet milling (AJM), ball milling (BM), cryogenic milling (CM), thin film freezing (TFF), and spray drying. First, AJM was performed to reduce the particle size of the CSP7 bulk powder, and the milled CSP7 was collected from several locations within the mill. Yield and particle size distribution of a first batch of milled powder (Batch 171013) collected from the indicated positions are shown in Tables 5 and 6. Particle size distribution was determined by Sympatec laser diffraction dry dispersion (Table 8), or Sympatec laser diffraction wet dispersion (Table 9), as above.

TABLE 8

Particle size distribution and yield of CSP7 powder (Batch 171013) using dry dispersion

| Position | Dv 10 (μm) | Dv 50 (μm) | Dv 90 (μm) | % 1-5 μm | Yield % |
|---|---|---|---|---|---|
| BFC + Grinding Chamber | 1.2 ± 0.0 | 2.7 ± 0.1 | 5.1 ± 0.2 | 83.7 ± 1.3 | 18% |
| Cyclone | 1.0 ± 0.0 | 2.7 ± 0.2 | 5.7 ± 0.0 | 73.6 ± 0.1 | 9% |
| Vessel | 1.0 ± 0.0 | 2.5 ± 0.0 | 4.9 ± 0.1 | 82.3 ± 0.8 | 6% |
| Adapter Vessel | 1.1 ± 0.0 | 2.5 ± 0.1 | 4.9 ± 0.1 | 82.6 ± 1.4 | 10% |

TABLE 9

Particle size distribution and yield of CSP7 powder (Batch 171013) using wet dispersion

| Position | Dv 10 (μm) | Dv 50 (μm) | Dv 90 (μm) | % 1-5 μm | Yield % |
|---|---|---|---|---|---|
| BFC + Grinding Chamber | 1.2 ± 0.0 | 3.1 ± 0.0 | 6.4 ± 0.1 | 80.0 ± 11.2 | 18% |
| Cyclone | 1.0 ± 0.0 | 3.4 ± 0.1 | 7.4 ± 0.2 | 61.3 ± 1.0 | 9% |
| Vessel | 1.1 ± 0.0 | 3.0 ± 0.0 | 5.9 ± 0.1 | 75.3 ± 0.9 | 6% |
| Adapter Vessel | 1.2 ± 0.0 | 2.9 ± 0.0 | 5.8 ± 0.0 | 78.2 ± 0.6 | 10% |

The second batch (Batch 171027) of CSP7 was milled from 10 grams of neat bulk powder using the same conditions as above. Again, powder size distribution and yield were assessed from the same locations and are listed in Table 10.

TABLE 10

Particle size distribution and yield of CSP7 powder (Batch 171027) using dry dispersion

| Position | Dv 10 (μm) | Dv 50 (μm) | Dv 90 (μm) | % 1-5 μm | Yield % |
|---|---|---|---|---|---|
| Bag + bag adaptor | 0.7 ± 0.0 | 1.4 ± 0.0 | 3.2 ± 0.1 | 68.3 ± 0.6 | 19.0 |
| BFC + Grinding Chamber | 1.0 ± 0.0 | 2.6 ± 0.1 | 5.0 ± 0.2 | 81.0 ± 1.3 | 16.9 |
| Cyclone | 0.9 ± 0.0 | 2.7 ± 0.1 | 5.6 ± 0.1 | 73.1 ± 1.2 | 17.2 |
| Vessel | 0.9 ± 0.0 | 2.3 ± 0.0 | 4.7 ± 0.1 | 80.3 ± 1.2 | 7.3 |
| Adaptor collection vessel | 0.9 ± 0.0 | 2.3 ± 0.0 | 4.4 ± 0.1 | 82.2 ± 1.2 | 15.9 |
| Total | | | | | 76.3 |

A third batch of CSP7 dry powder was subjected to thin film freezing (TFF) (batch 171014) and analyzed as above, using both Sympatec Laser Diffraction Dry Dispersion (Table 11) and Wet Dispersion (Table 12).

TABLE 11

Particle size distribution and yield of CSP7 powder (Batch 171014) using dry dispersion

| Dv 10 (μm) | Dv 50 (μm) | Dv 90 (μm) | % 1-5 μm |
|---|---|---|---|
| 2.1 ± 0.0 | 5.7 ± 0.1 | 10.4 0.3 | 37.0 ± 0.6 |

TABLE 12

Particle size distribution and yield of CSP7 powder (Batch 171014) using wet dispersion

| Dv 10 (μm) | Dv 50 (μm) | Dv 90 (μm) | % 1-5 μm |
|---|---|---|---|
| 3.8 ± 0.0 | 7.1 ± 0.0 | 13.3±0.2 | 24.6 ± 0.7 |

Another batch of CSP7 dry powder was subjected to cryogenic milling (CM) to reduce the particle size. The particle size of the CM CSP7 was assessed by laser diffraction using dry dispersion (Table 13) and wet dispersion (Table 14) as above.

TABLE 13

Particle size distribution and yield of CM CSP7 powder (dry dispersion)

| Dv 10 (μm) | Dv 50 (μm) | Dv 90 (μm) | % 1-5 μm |
|---|---|---|---|
| 0.7 ± 0.0 | 2.7 ± 0.2 | 17.4 0.9 | 42.7 ± 0.5 |

TABLE 14

Particle size distribution and yield of CM CSP7 powder (wet dispersion)

| Dv 10 (μm) | Dv 50 (μm) | Dv 90 (μm) | % 1-5 μm |
|---|---|---|---|
| 1.5 ± 0.0 | 10.5 ± 0.1 | 38.5 ± 0.7 | 28.2 ± 0.1 |

Another batch of CSP7 bulk powder was subjected to ball milling (BM) to reduce the particle size. The particle size distributions of BM CSP7 powder taken from several time points during the milling process are presented in Table 15.

TABLE 15

Particle size distribution and yield of BM CSP7 powder (wet dispersion)

| Duration | Dv 10 (μm) | Dv 50 (μm) | Dv 90 (μm) | % 1-5 μm |
|---|---|---|---|---|
| 5 min | 0.8 ± 0.0 | 3.8 ± 0.2 | 12.5 ± 0.4 | 43.0 ± 0.7 |
| 10 min | 0.7 ± 0.0 | 2.3 ± 0.1 | 9.2 ± 0.2 | 49.0 ± 0.6 |
| 30 min | 0.6 ± 0.0 | 1.4 ± 0.0 | 5.3 ± 0.3 | 55.5 ± 0.7 |

Figure 8:
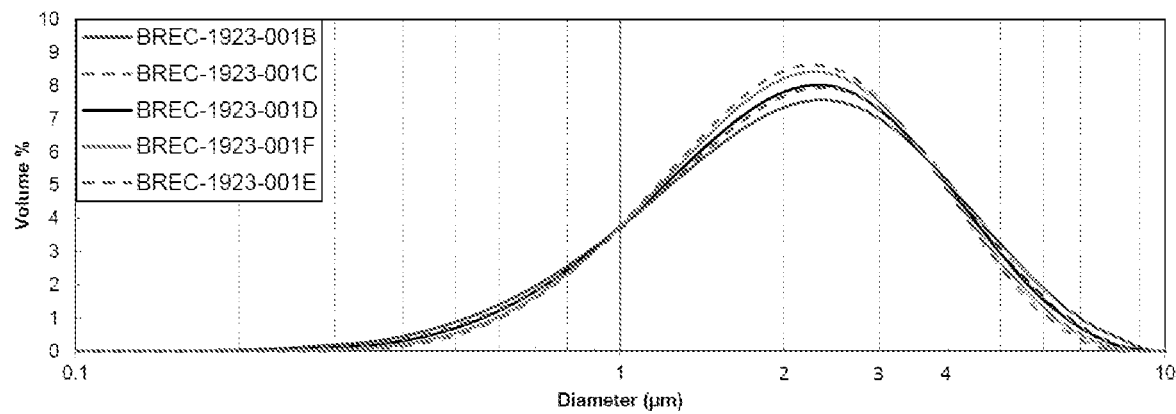
FIG. 8: Particle Size Distribution of Spray Dried CSP7. CSP7 was mixed with either leucine, trehalose, sodium citrate, or leucine and trehalose, and spray dried. Particle size was evaluated by Malvern Mastersizer 2000 (laser light diffraction, Fraunhofer approximation; dispersive air pressure: 3.0 Bar). Pictured are curves of each spray dried mixture.
Figure 9:
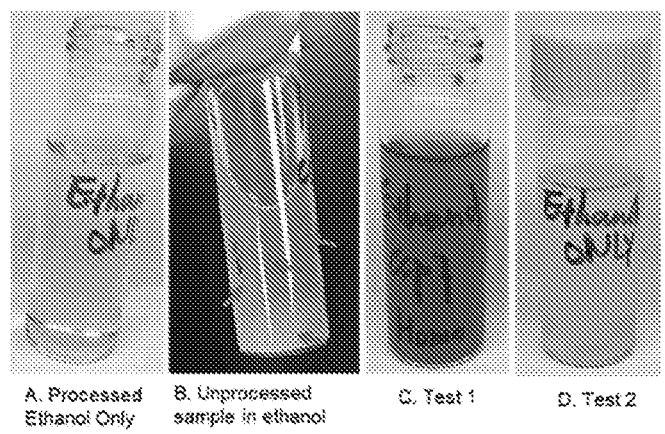
FIG. 9: Visual observation of homogenized CSP7 suspension. A. Ethanol processed with the highest power of rotor-stator for 1 min; B. Unprocessed CSP7-ethanol suspension, red arrow indicates large particles/aggregates; C. CSP7-ethanol suspension processed with the highest power of rotor-stator for 1 min, suspension turns dark grey; D. CSP7-ethanol suspension processed with the lowest power of rotor-stator for 1 min, suspension turns light grey.

Further batches were produced with mixtures of CSP7 (also referred to by the assigned development acronym, CSP7) and leucine, trehalose, sodium citrate, or leucine and trehalose, and subjected to spray drying to reduce particle size. The size of spray dried particles was examined by dry dispersion laser diffraction (FIG. 8, Table 16). Again, relative to Bulk CSP7, spray drying significantly reduced the size of the CSP7 particles.

TABLE 16

Spray dry manufacturing of CSP7 mixtures

Figure 10:
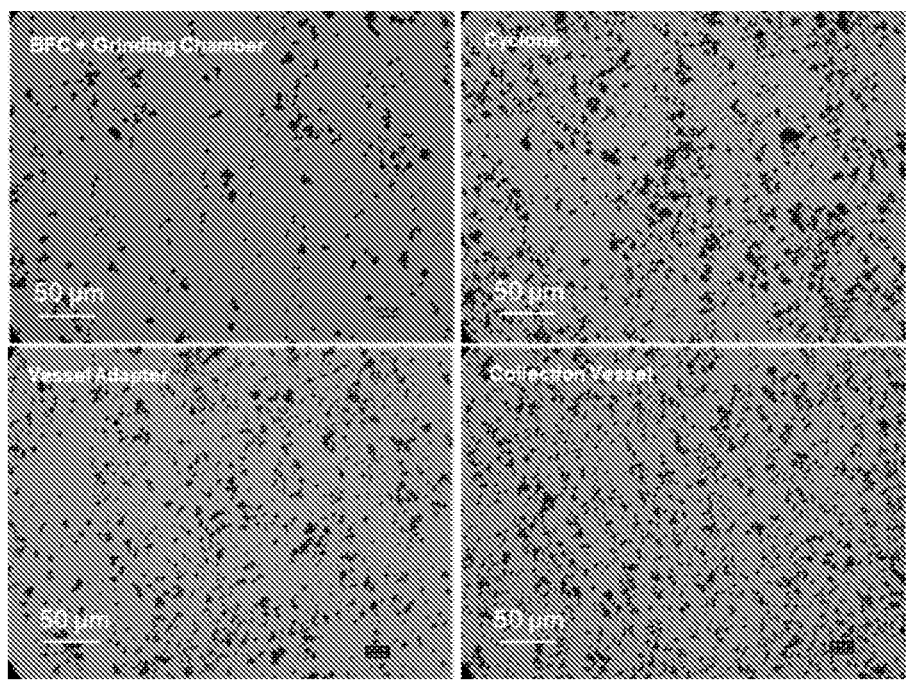
FIG. 10: Optical Microscopy of Air Jet Milled CSP7 Powder. Powder samples collected from the indicated locations of the air jet mill were imaged by optical microscopy. Pictured are representative images.
Figure 11:
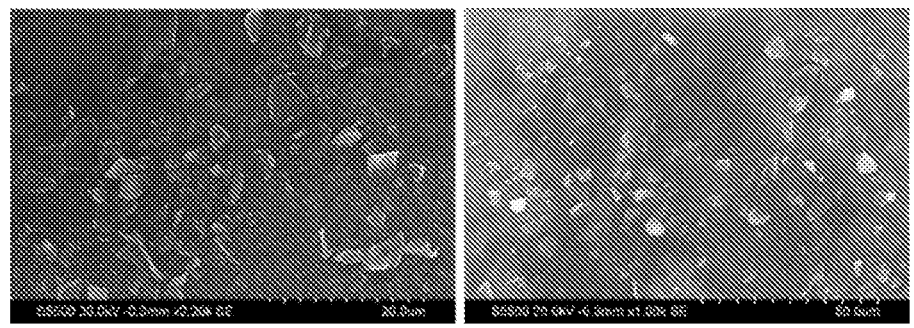
FIG. 11: Scanning Electron Microscopy of Air Jet Milled CSP7 Powder. Milled CSP7 powder (batch 171027) was imaged by Scanning Electron Microscopy (SEM) under identical conditions to the bulk CSP7 powder. Pictured is a representative SEM image of the milled CSP7 powder.
Figure 12:
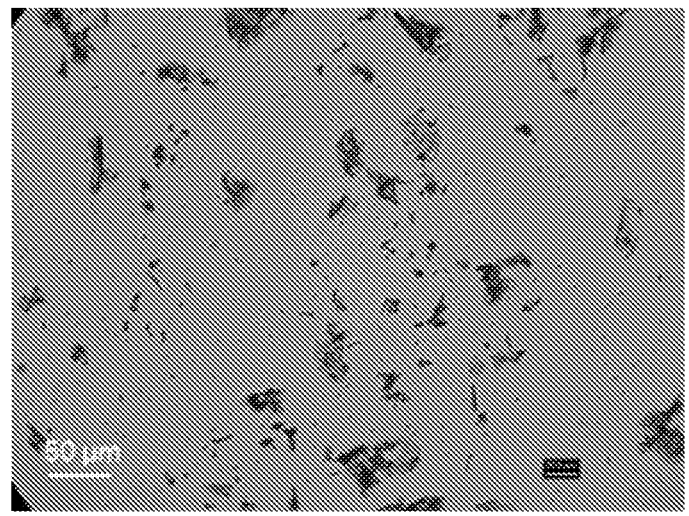
FIG. 12: Light Microscopy of CSP7 Following Thin Film Freezing. Powder samples were sputtered on the glass slides and viewed using a Leica optical microscope (Leica CTR6500). Scale bars are indicated in the lower left hand corner of each image.
Figure 13:
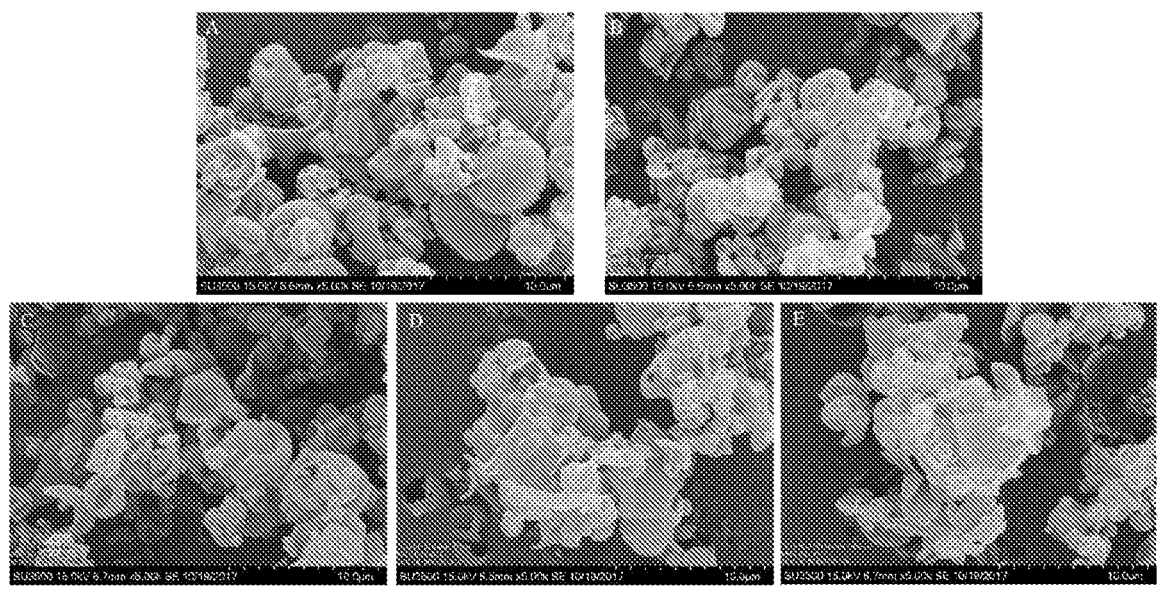
FIG. 13: Scanning Electron Microscopy of Spray Dried CSP7. Particle morphology of spray dried CSP7 mixtures (A=100% LTI, B=leucine, C=trehalose, d=sodium citrate, e=leucine and trehalose) was examined using SEM. Representative images are pictured.

| Lot ID Formulation | BREC-1923-001B 100% CSP7 | BREC-1923-001C 75/25 CSP7/ Leucine | BREC-1923-001D 75/25 CSP7/ Trehalose | BREC-1923-001E 75/25 CSP7/Sodium Citrate | BREC-1923-001F 75/15/10 CSP7/Leucine/ Trehalose |
|---|---|---|---|---|---|
| Dryer | BLD-35 with 2' cyclone | | | | |
| Solvent | pH = ~10 water (adjusted with $NH_4OH$) | | | | |
| Nozzle | 2-Fluid | | | | |
| Batch Size (g) | 4 | 4 | 4 | 2 | 4 |
| Mass Yield (g) | 3.07 | 2.98 | 3.12 | 1.60 | 3.04 |
| % Yield | 77 | 75 | 78 | 79 | 76 |
| D(v,0.1) (μm) | 0.81 ± 0.04 | 0.91 ± 0.00 | 0.85 ± 0.04 | 0.84 ± 0.04 | 0.89 ± 0.01 |
| D(v,0.5) (μm) | 1.99 ± 0.01 | 1.96 ± 0.00 | 1.98 ± 0.02 | 1.99 ± 0.01 | 1.97 ± 0.02 |
| D(v,0.9) (μm) | 4.20 ± 0.12 | 3.79 ± 0.01 | 4.01 ± 0.10 | 4.06 ± 0.11 | 3.88 ± 0.03 |

CSP7 particle size was dramatically reduced following each of the methods for reducing the particle size (air jet milling, thin film freezing, cryogenic milling, ball milling, and spray drying), both when measured by solid dispersion, and wet dispersion (Compare Tables 1 and 2 to Tables 5, 6, 10, 13, 14, 16, 17, 18 and 19). Following air jet milling, the majority of the CSP7 particles fall within the respirable range, however thin film freezing, cryogenic milling, and ball milling were not quite as effective, with smaller percentages of the milled powders falling within the respirable range when measured by laser diffraction using solid dispersion or liquid dispersion.

Particle size was also reduced using a rotor-stator handheld homogenizer (FIG. 9). CSP7 changed color in ethanol following homogenization to either light or dark grey, depending on the duration and power of homogenization FIG. 9, and it is clear that homogenization reduced particle size, though the method was not further pursued due to the observed color change.

Morphology of milled CSP7 powders. Morphology of each of the milled samples was examined using optical microscopy or Scanning Electron Microscopy. The powder samples from the air jet mill were examined as above and the optical microscopy indicated that the particle size was reduced to a size of 1 µm> particle size>5 µm, and homogenous (FIG. 10). Further, the milled CSP7 particles were free of agglomerates (FIG. 10). SEM indicated that the homogenized and reduced particle size of the air jet milled particles was between 1 and 5 µm (FIG. 11). The powder samples obtained after TFF were also examined, and while particle sizes were larger, the sample was found to be free of agglomerate (FIG. 12). Further analysis included assessment of the particle morphology of the spray dried formulations by scanning electron microscopy. Representative SEM images of the formulations are shown in FIG. 13.

Figure 14:
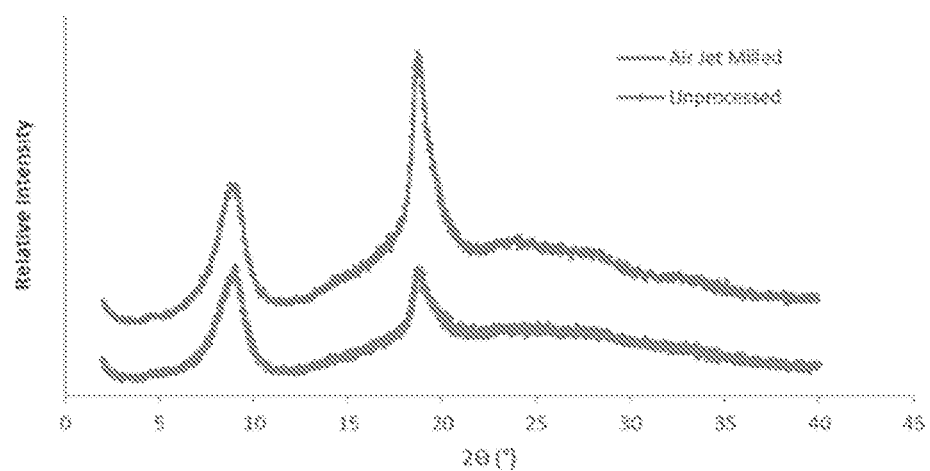
FIG. 14: X-ray Powder Diffraction of Air Jet Milled CSP7 Powder. X-ray powder diffraction profiles of milled (batch 171027) and unprocessed bulk CSP7 powder are shown. Diffraction curves indicate a decrease in crystallinity in the milled CSP7.
Figure 15:
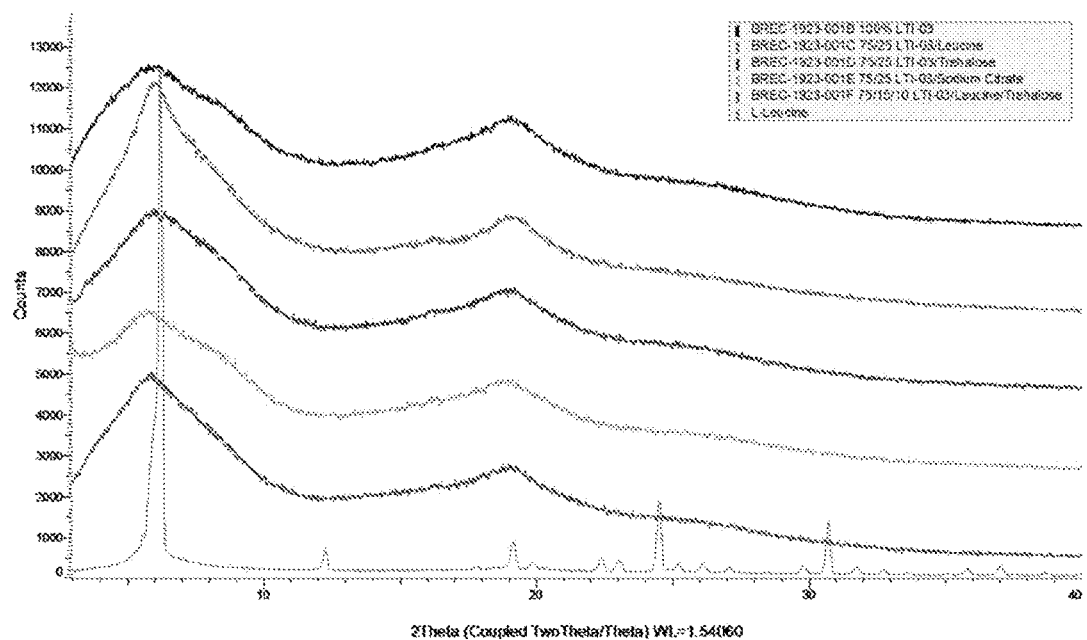
FIG. 15: Physical State of Spray Dried CSP7. Spray dried CSP7 mixtures were examined by X-ray diffraction. Curves indicating the crystallinity or lack thereof of each spray dried mixture of CSP7 are shown.

Crystallinity of AJM CSP7. Milled CSP7 powder (batch 171027) was evaluated by X-ray diffraction and crystallinity exhibited in diffractogram (FIG. 14). Crystallinity of spray dried CSP7 was also examined by X-ray diffraction and the curves are pictured in FIG. 15. The formulations of CSP7

$$Potency = \frac{Free\ CSP7\ peptide\ conc.\ from\ HPLC\ result}{Free\ CSP7\ peptide\ conc.\ from\ mass\ balance} \times 100\%$$

It is clear from Table 26, that milling had no deleterious effect on the potency of any of the samples collected. Similarly, when Batch 171027 was tested, the chemical potency was determined to be 100.14%

TABLE 26

Potency of milled CSP7 powder (Batch 171013)

| Position | Collection Vessel | Vessel Adaptor | Cyclone | BCF + Chamber |
|---|---|---|---|---|
| Potency by HPLC | 100.7% | 101.3% | 102.6% | 100.7% |

Figure 16:
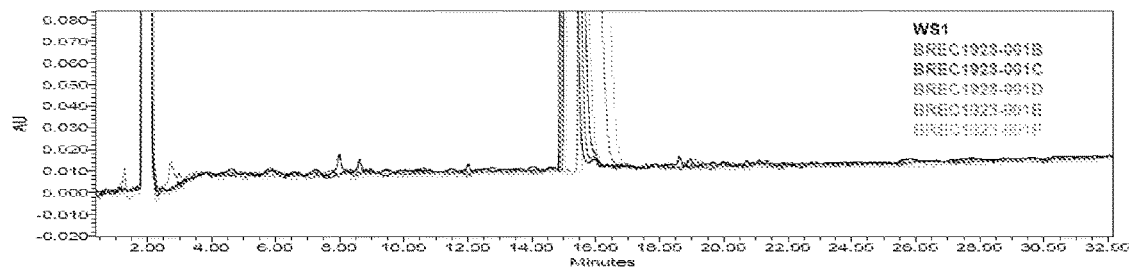
FIG. 16: HPLC Analysis of Spray Dried CSP7. The purity of spray dried CSP7 mixtures were examined by assaying their chemical potency using HPLC.

The spray dried CSP7 mixtures was examined by RP-HPLC to examine purity (Table 17, FIG. 16). Similar to the air jet milled CSP7 powder, the spray dried CSP7 retains roughly 100% purity.

TABLE 17

Purity of spray dried formulations of CSP7

| Relative Abundance >LOQ | | | Impurity #1 | Impurity #2 | Impurity #3 | Primary ACTIVE Peak | Impurity #4 | Impurity #5 | Total Impurities |
|---|---|---|---|---|---|---|---|---|---|
| Retention Time | | | 7.99 | 8.62 | 12.03 | 14.93 | 18.30 | 18.86 | |
| Relative Ret. Time | | | 0.54 | 0.58 | 0.81 | 1.00 | 1.23 | 1.26 | |
| API standard | 1/0/00 | | 0.60 | 0.26 | — | 99.01 | — | 0.13 | 0.99 |
| API standard | 1/0/00 | | 0.27 | 0.26 | 0.14 | 99.16 | — | 0.16 | 0.84 |
| 100% CSP7 | BREC1923-001B | A1 | — | — | — | 100.00 | — | — | — |
| 100% CSP7 | BREC1923-001B | A2 | — | — | — | 99.64 | — | 0.36 | 0.36 |
| 75/25 CSP7/Leucine | BREC1923-001C | B1 | — | — | — | 100.00 | — | — | — |
| 75/25 CSP7/Leucine | BREC1923-001C | B2 | — | — | — | 99.79 | — | 0.21 | 0.21 |
| 75/25 CSP7/Trehalose | BREC1923-001D | C1 | — | — | — | 99.63 | 0.14 | 0.23 | 0.37 |
| 75/25 CSP7/Trehalose | BREC1923-001D | C2 | — | — | — | 99.53 | 0.16 | 0.31 | 0.47 |
| 75/25 CSP7/Sodium Citrate | BREC1923-001E | D1 | — | — | — | 99.72 | 0.11 | 0.17 | 0.28 |
| 75/25 CSP7/Sodium Citrate | BREC1923-001E | D2 | — | — | — | 99.82 | 0.18 | — | 0.18 |
| 75/15/10 CSP7/Leucine/Trehalose | BREC1923-001F | E1 | — | — | — | 99.84 | 0.16 | — | 0.16 |
| 75/15/10 CSP7/Leucine/Trehalose | BREC1923-001F | E2 | — | — | — | 99.84 | 0.16 | — | 0.16 | alone, or CSP7 coupled with trehalose or sodium citrate are amorphous, while CSP7 coupled with leucine or leucine and trehalose appear to contain crystalline leucine character, as shown by the sharp peaks in FIG. 15.

Figure 17:
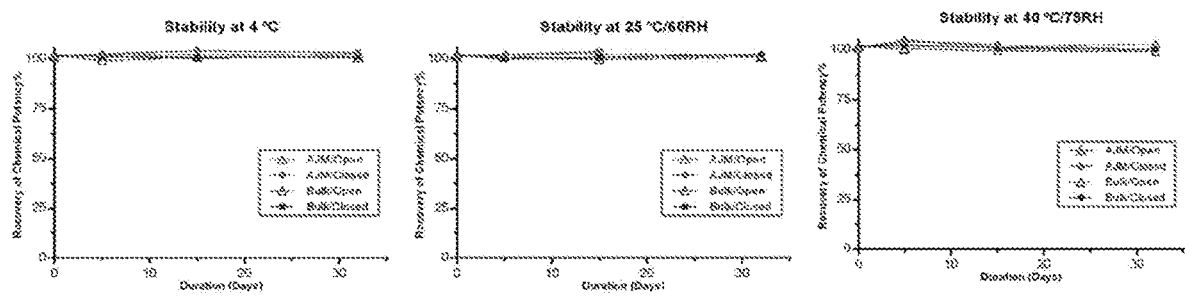
FIG. 17: HPLC analysis of Air Jet Milled CSP7 Stability. The stability of both unprocessed bulk CSP7 powder, as well as air jet milled CSP7 (batch 171027) were examined by assaying their chemical potency using HPLC. A sample of each was stored in 3 different conditions (4° C., 25° C./60 RH, 40° C./75 RH) with open/closed vial lid before assaying the chemical potency at 5, 15, and 32 days of storage.

HPLC Evaluation of Milled or Spray Dried CSP7 Powder. To determine whether milling the CSP7 bulk powder had any effect on chemical potency, samples of milled CSP7 powder were collected from various parts of the mill were assessed using HPLC performed under the conditions listed in Table 2. Potency was evaluated using the equation:

CSP7 stability. The stability of both unprocessed bulk CSP7 powder, as well as air jet milled CSP7 (batch 171027) were examined by assaying their chemical potency using HPLC. A sample of each was stored in 3 different conditions before assaying the chemical potency at 5, 15, and 32 days of storage (FIG. 17). Stability of spray dried CSP7 over a period of 24 hours was also examined by HPLC (method described earlier in specification) to understand its short term stability. Each of the formulations was found to be stable, with no increase in impurities after 2 or 24 hours (Table 31).

TABLE 31 stability of spray dried CSP7

| | 100% LTI-03 | | | 100% LTI-03 | | | 75% CSP7 25% Leucine | | | 75% CSP7 25% Trehalose | | | 75% CSP7 25% Sodium Citrate | | | WS |
|---|---|---|---|---|---|---|---|---|---|---|---|---|---|---|---|---|
| Base Used | Ammonium hydroxide | | | Sodium hydroxide | | | Ammonium hydroxide | | | Ammonium hydroxide | | | Ammonium hydroxide | | | NA |
| Time Point | 0 hr | 2 hr | 24 hr | Initial | 2 hr | 24 hr | Initial | 2 hr | 24 hr | Initial | 2 hr | 24 hr | 0 hr | 2 hr | 24 hr | 0 hr |
| Purity (% main peak) | 99.7 | 99.6 | 99.5 | 99.6 | 99.6 | 99.3 | 99.6 | 99.7 | 99.6 | 99.6 | 99.6 | 99.6 | 99.6 | 99.6 | 99.6 | 98.9 |

Figures 18, 19:
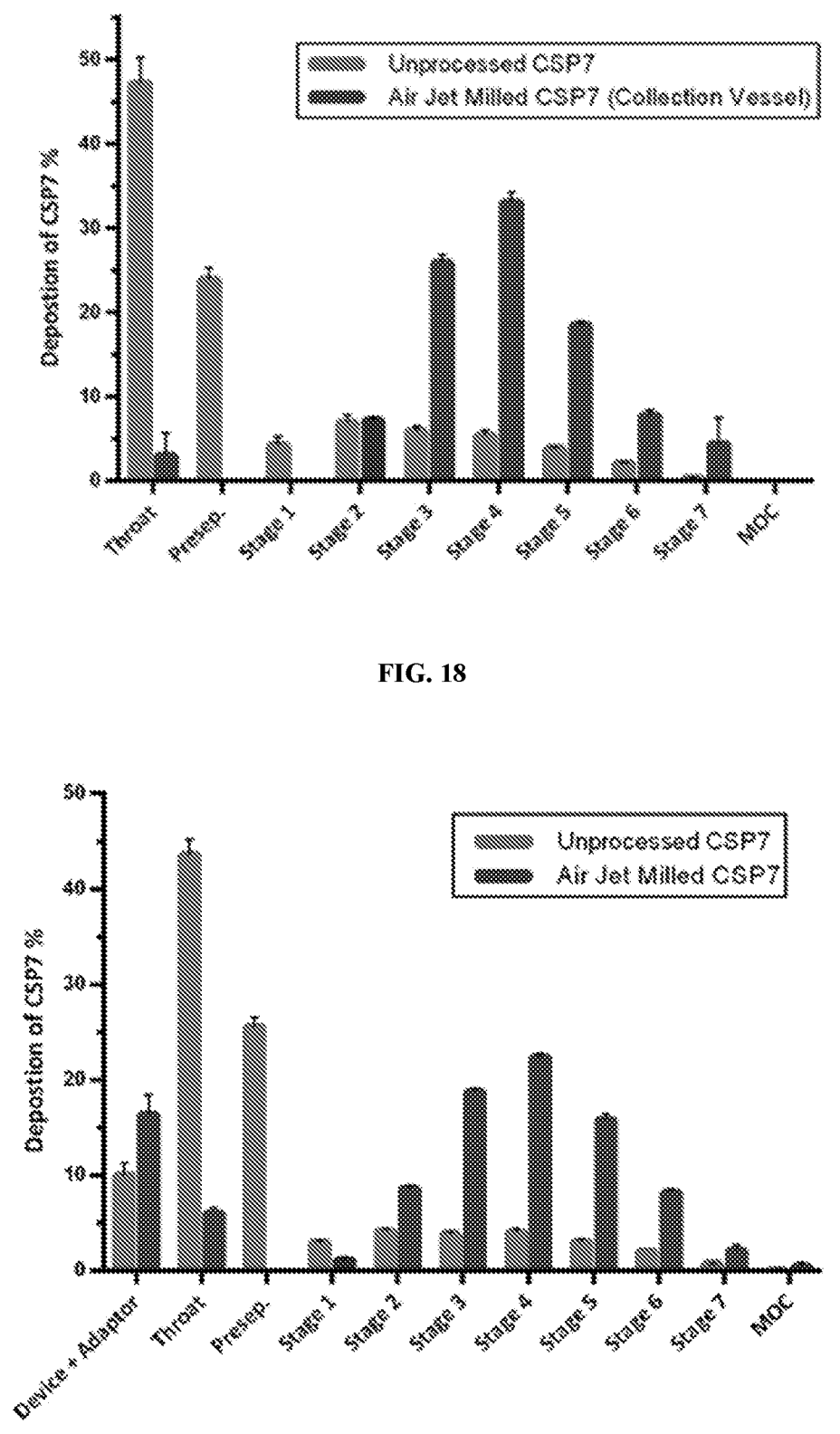

Aerodynamic particle size distribution of milled CSP7. To determine aerodynamic particle size distribution of milled CSP7, the amount of powder deposited in various locations of the NGI collector were extracted separately. The delivered dose was measured as the mass of CSP7 that entered the NGI collector after aerosolization, and the amount of CSP7 that was deposited on individual surfaces was extracted and measured separately. The amount of CSP7, either unprocessed or air jet milled (batch 171013) that was left in the capsule, or deposited within the device, adaptor, throat, pre-separator, and stages 1-MOC are shown in FIG. 18 as a percentage of the total amount of CSP7 delivered. The fine particle fraction percentage (FPF %), mass mean aerodynamic diameter (MMAD), and geometric standard deviation (GSD) of both milled and untreated (e.g., unmilled or unprocessed) CSP7 are presented in Table 9.

TABLE 9

Geometric properties of AJM CSP7 powder (Batch 171013)

| | FPF % (<5 μm) | MMAD (μm) | GSD (μm) |
|---|---|---|---|
| Unprocessed CSP7 | 19.3 ± 1.4 | 3.5 ± 0.2 | 2.3 ± 0.2 |
| Air Jet Milled CSP7 | 93.7 ± 3.1 | 2.2 ± 0.1 | 1.7 ± 0.0 |

The aerodynamic particle size distribution of the second milled CSP7 batch (171027) was determined as above, except using about 4.25 mg of powder per size 3 HPMC capsule. The GSD, FPF %, and MMAD are presented in Table 11, and the percentage of CSP7 deposited in each location is presented in FIG. 19, again as a percentage of the total amount of CSP7 delivered.

TABLE 11

Geometric properties of CSP7 powder batch 171027

| | FPF % (<5 μm) | MMAD (μm) | GSD (μm) |
|---|---|---|---|
| Unprocessed CSP7 | 16.4 ± 0.9 | 3.0 ± 0.3 | 2.5 ± 0.0 |
| Air Jet Milled CSP7 | 84.5 ± 0.7 | 2.2 ± 0.0 | 1.9 ± 0.0 |

Figure 20:
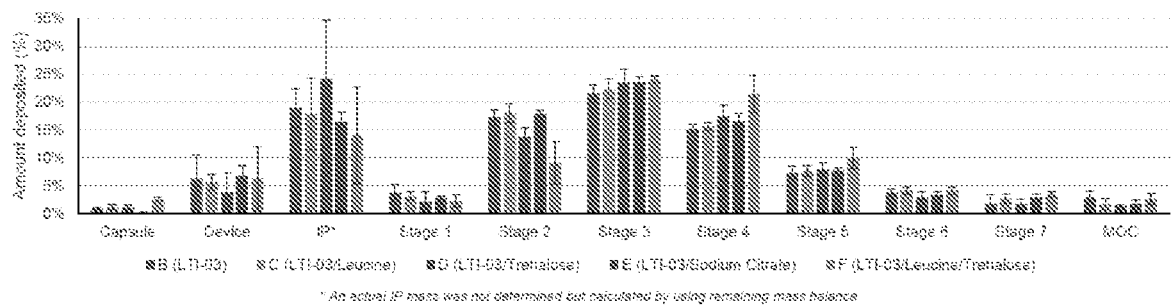
FIG. 20: Aerosol Performance of Spray Dried CSP7 Mixtures. After aerosolization by NGI, all collection surfaces were rinsed with known volumes of 20 mM Tris buffer (pH 10.3). Powders deposited in the capsule, device, adaptor, throat, pre-separator, and stages 1-MOC were extracted separately and measured. Indicated is the percentage of powder deposited in a specific location.

Aerosolization of the spray dried formulations were examined as well (FIG. 20). Each of the formulations exhibited a fine powder fraction of greater than 60%, with each formulation having a MMAD of between 2.5 um and 3 um (Table 25). A summary of the results of the analyses of the spray dried formulations, including water content, is presented in Table 25.

TABLE 25

Analytical summary of spray dried CSP7 mixtures

| Lot ID Formulation | BREC1923-001B 100% CSP7 | BREC1923-001C 75/25 CSP7/ Leucine | BREC1923-001D 75/25 CSP7/ Trehalose | BREC1923-001E 75/25 CSP7/Sodium Citrate | BREC1923-001F 75/15/10 CSP7/Leucine/ Trehalose |
|---|---|---|---|---|---|
| Water Content (wt %) | 2.1 ± 0.1 | 1.8 ± 0.0 | 2.1 ± 0.0 | 2.5 ± 0.1 | 1.8 ± 0.1 |
| Assay (mg A/g, % target) | 1059 ± 14 (106%) | 782 ± 0 (104%) | 784 ± 3 (105%) | 745 ± 9 (99%) | 757 ± 12 (101%) |
| Purity (% main peak) | 99.8 ± 0.3 | 99.9 ± 0.2 | 99.6 ± 0.1 | 99.8 ± 0.1 | 99.8 ± 0.0 |
| Particle Morphology (SEM) | Collapsed shells with some fragments | Collapsed shells | Collapsed shells | Collapsed shells with some fragments | Collapsed shells with some fragments |
| Physical State (PXRD) | Amorphous | Primarily Amorphous w/crystalline leucine character | Amorphous | Amorphous | Primarily Amorphous w/crystalline leucine character |
| Thermal Properties(DSC) Midpoint Tg (° C.) | 132.4 ± 6.3 | 97.4 ± 1.6 | 77.1 ± 2.2 | 80.4 ± 0.4 | 79.6 ± 2.3 |

TABLE 25-continued

Analytical summary of spray dried CSP7 mixtures

| | Lot ID Formulation | | BREC1923-001B 100% CSP7 | BREC1923-001C 75/25 CSP7/ Leucine | BREC1923-001D 75/25 CSP7/ Trehalose | BREC1923-001E 75/25 CSP7/Sodium Citrate | BREC1923-001F 75/15/10 CSP7/Leucine/ Trehalose |
|---|---|---|---|---|---|---|---|
| Aerosol Results | MMAD (μm) | | 2.97 ± 0.16 | 2.95 ± 0.05 | 2.83 ± 0.04 | 2.94 ± 0.06 | 2.46 ± 0.26 |
| | GSD | | 1.8 ± 0.1 | 1.7 ± 0.0 | 1.8 ± 0.2 | 1.7 ± 0.0 | 1.7 ± 0.0 |
| | EF (%) | | 93 ± 4 | 93 ± 2 | 95 ± 4 | 93 ± 2 | 91 ± 6 |
| | FPF (%) | | 64 ± 7 | 67 ± 6 | 65 ± 9 | 69 ± 3 | 77 ± 9 |

Figure 21:
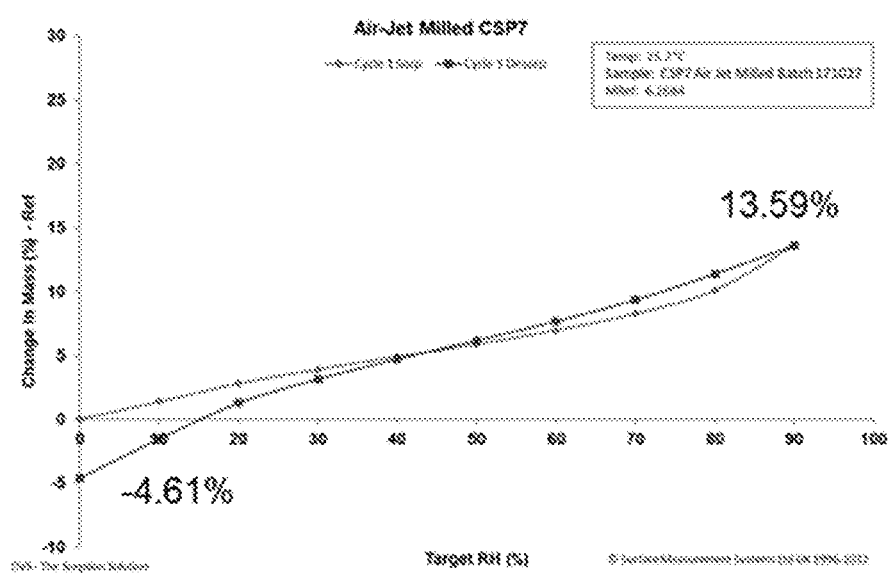
FIG. 21: Dynamic Vapor Sorption of Air Jet Milled CSP7 Powder. Milled CSP7 powder (batch 171027) was run on a Surface Measurement Systems DVS instrument for a full sorption/desorption cycle from 0% to 90% relative humidity in steps of 10% at 25° C. Moisture desorption at 0% humidity and mass change at 90% humidity are indicated.

MMAD-mass median aerodynamic diameter
GSD-geometric standard deviation
EF-emitted fraction
FPF-fine particle fraction Determination of moisture content of milled CSP7. Under the same conditions used to analyze the bulk CSP7, air jet milled CSP7 powder (batch 171027) was analyzed using Dynamic Vapor Sorption (FIG. 21). Similar to the bulk neat powder, the milled CSP7 had a moisture desorption of 4.61% in relative humidity of 0% (FIG. 21). The KF-V analysis which found a moisture content of 4.9% (Table 7), though there was an increase in mass change to 13.59% when the relative humidity of 90% (FIG. 21).

TABLE 7

KF-C of CSP7 batch 171027

| Test | Moisture Content |
|---|---|
| 1 | 4.8% |
| 2 | 4.9% |
| 3 | 5.0% |
| Average | 4.9% |

Figure 22:
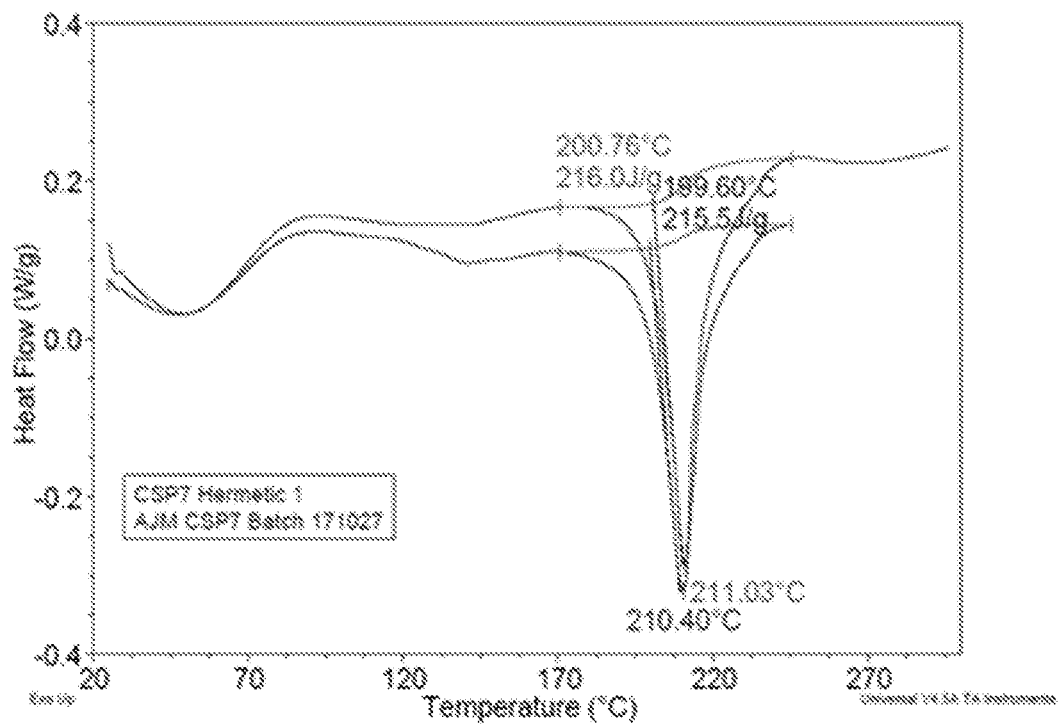
FIG. 22: Thermal analysis of Air Jet Milled CSP7 Powder. Differential Scanning calorimetry (DSC) was performed on milled CSP7 (batch 171027) using a calorimeter as above. Pictured is a curve from DSC with a frequency of 1° C./60 s and a rate of 2° C./min, ramping from 25 to 300° C.
Figure 23:
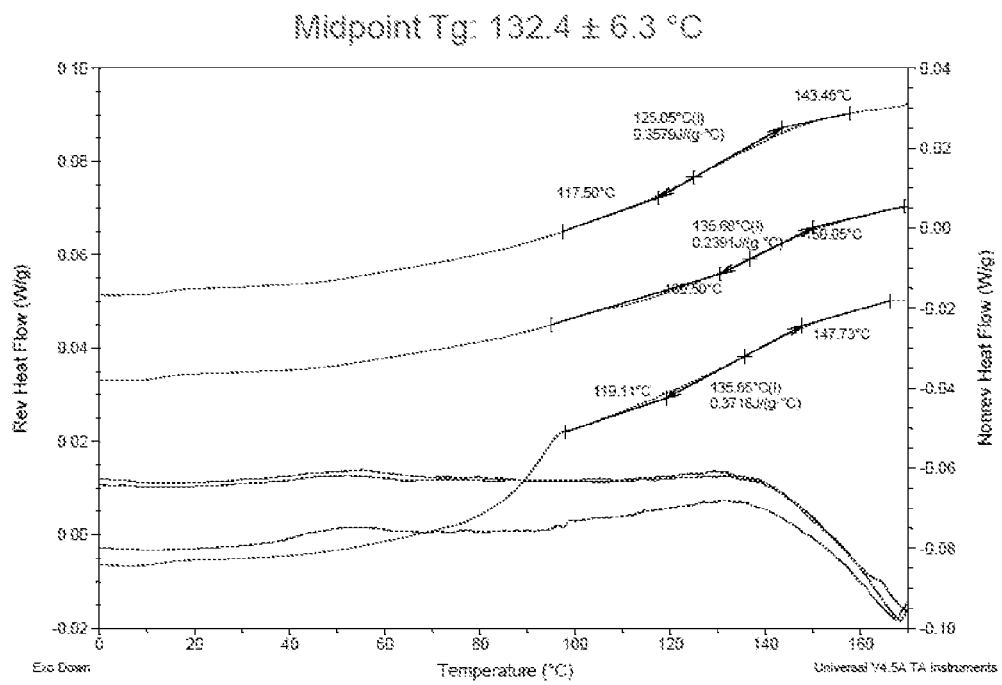
FIG. 23: Thermal Properties of Spray Dried 100% CSP7. Excipient free spray dried CSP7 was analyzed by modulated differential scanning calorimetry. Pictured is the mDSC curve.
Figure 24:
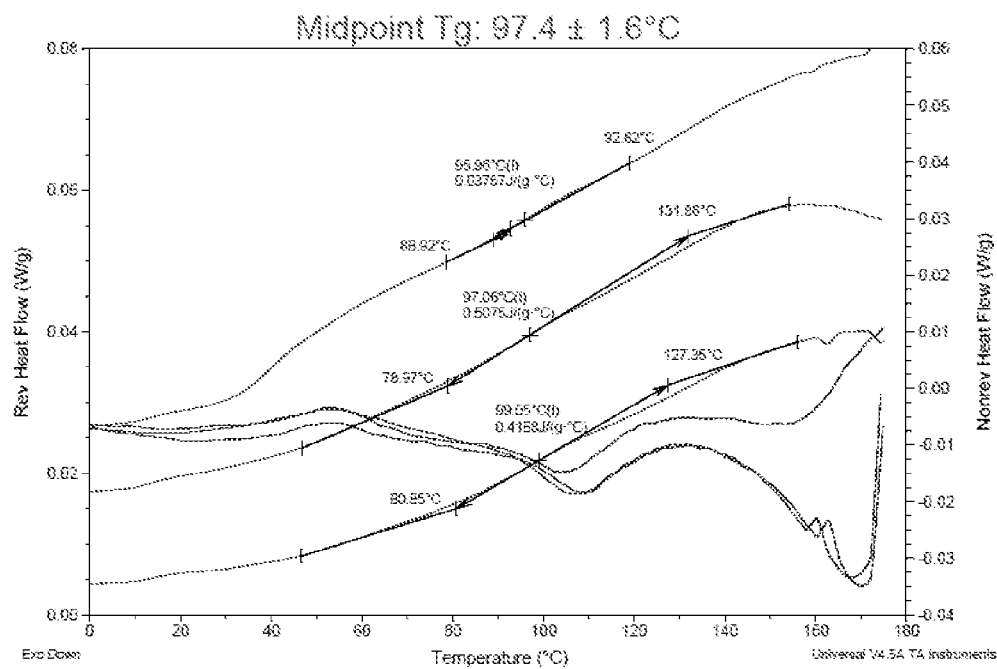
FIG. 24: Thermal Properties of Spray Dried CSP7 with Leucine. Spray dried CSP7 mix containing 25% leucine was analyzed by modulated differential scanning calorimetry. Pictured is the mDSC curve.
Figure 25:
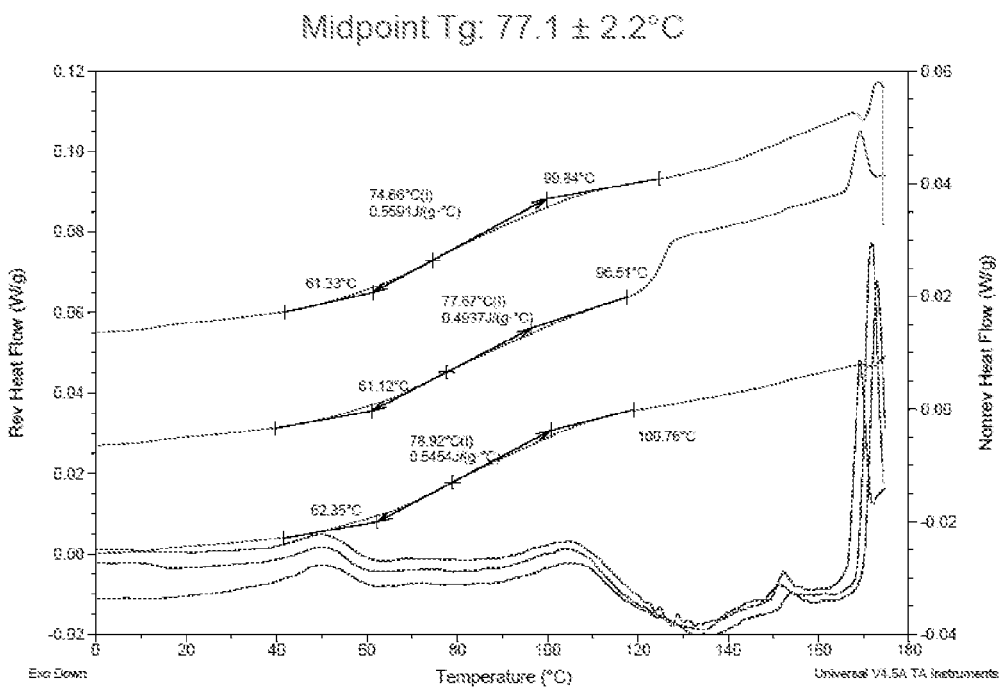
FIG. 25: Thermal properties of Spray Dried CSP7 with Trehalose. Spray dried CSP7 mix containing 25% trehalose was analyzed by modulated differential scanning calorimetry. Pictured is the mDSC curve.
Figure 26:
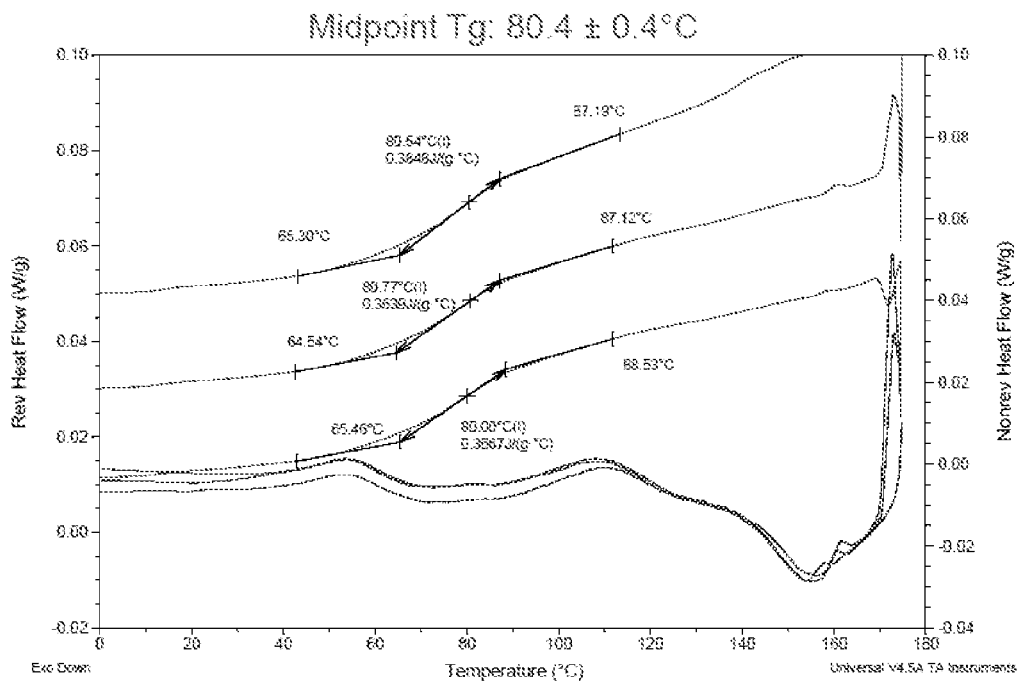
FIG. 26: Thermal properties of Spray Dried CSP7 with Sodium Citrate. Spray dried CSP7 mix containing 25% sodium citrate was analyzed by modulated differential scanning calorimetry. Pictured is the mDSC curve.
Figure 27:
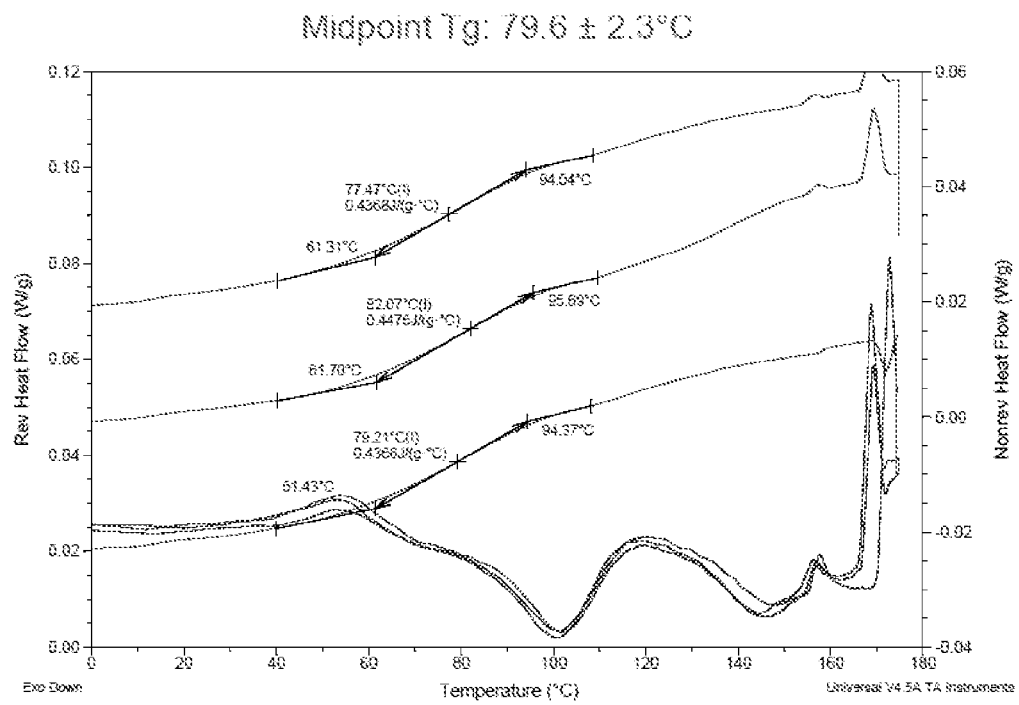
FIG. 27: Thermal properties of Spray Dried CSP7 with Leucine and Trehalose. Spray dried CSP7 mix containing 15% leucine and 10% trehalose was analyzed by modulated differential scanning calorimetry. Pictured is the mDSC curve.
Figure 28:
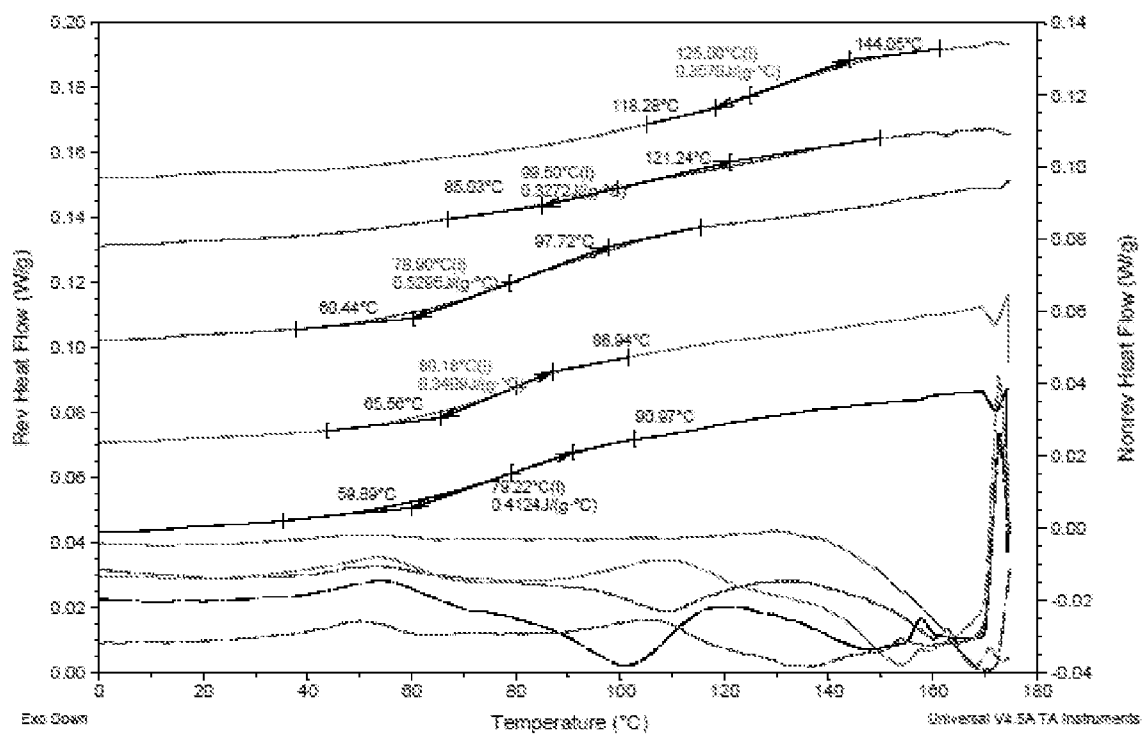
FIG. 28: Thermal properties of All Spray Dried CSP7 Mixtures. Each of the manufactured spray dried CSP7 mixtures was analyzed by mDSC. All mDSC curves for these powders are pictured.

Thermogravimetric analysis of reduced particle size CSP7 powders. Thermogravimetric analysis was performed on milled CSP7 (batch 171027) in an identical manner to bulk CSP7, and it was found that the milled CSP7 had very similar properties to the unprocessed CSP7 (FIG. 22). The thermal properties of the spray dried formulations were also evaluated and are shown in Table 24 and FIGS. 23-27 (summarized in FIG. 28). Notably, the midpoint Tg of the mixed formulations was significantly lower than the spray dried CSP7 alone (Compare 001C-F to 001B in Table 24).

The results presented herein indicate that a variety of methods for reducing the particle size of CSP7 powder are effective, and that the resulting powders exhibit very similar characteristics.

Figure 29:
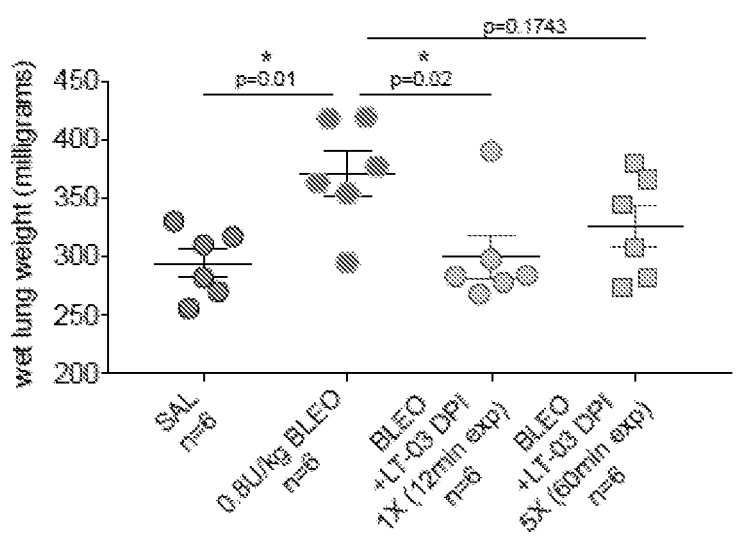
FIG. 29: Wet Weight of Dissected Lung Tissues from Mice. Euthanized mice were dissected and their lungs removed and weighed. Mice were either saline treated, bleomycin treated to induce lung fibrosis, or bleomycin treated and treated with CSP7 peptide for 12 or 60 min.

Example 4—Treatment of Bleomycin Induced Lung Fibrosis by Inhalation of CSP7 Dry Powder Induction and CSP7 treatment of fibrosis in mice. Lung fibrosis was induced in mice by treatment with Bleomycin. Mice were dosed with 0.8 U/kg bleomycin intranasally and wait for 14 days to develop disease before treatment. Mice were then left untreated, or treated by dry powder inhalation of CSP7 for 12 minutes, or treated by dry powder inhalation of CSP7 for 60 minutes. Mice were euthanized at the last day of the treatment and lungs were removed, flash frozen, and stored at −80° C. Flash frozen lungs were weighed prior to further analysis (FIG. 29).

Figure 30:
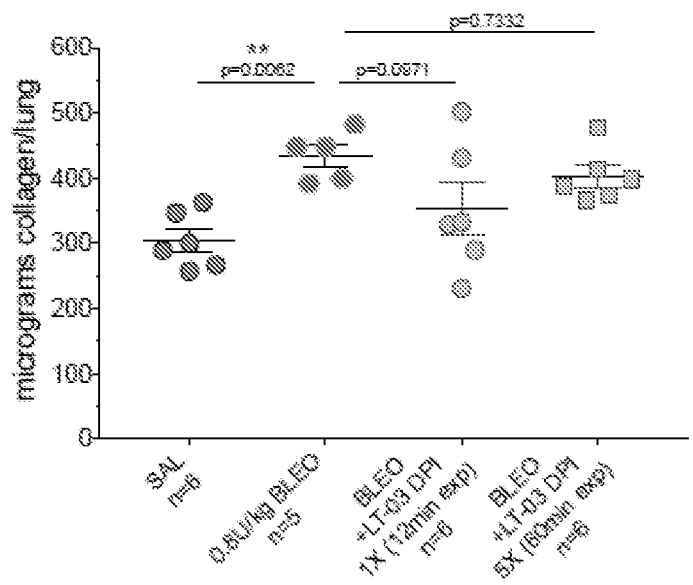
FIG. 30: Collagen Content of Murine Lung Tissue. Untreated, bleomycin treated, or bleomycin and CSP7 treated lung tissues were homogenized and collagen content was analyzed using the Quickzyme collagen assay. Graph depicts total collagen content of the lungs.
Figure 31:
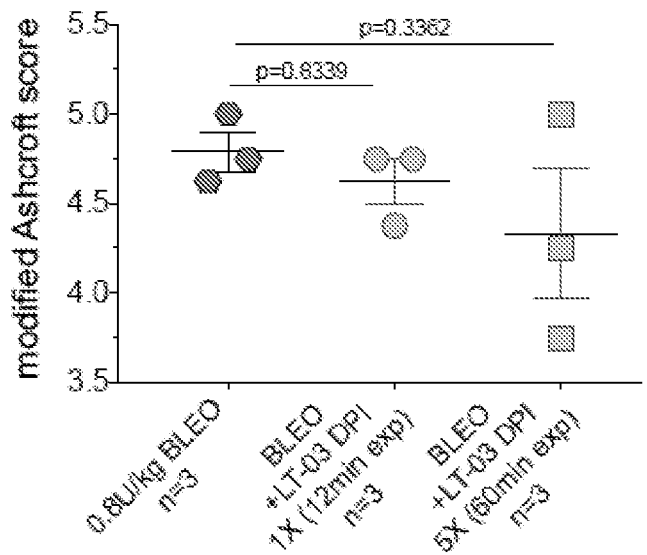
FIG. 31: Ashcroft Scores of Murine Lung Tissues. Untreated, bleomycin treated, or bleomycin and CSP7 treated lung tissues were homogenized and collagen content was analyzed using the Quickzyme collagen assay. Ashcroft scores were determined as described by Hubner et al. 2008, incorporated herein by reference. Graph depicts total collagen content of the lungs.
Figure 32:
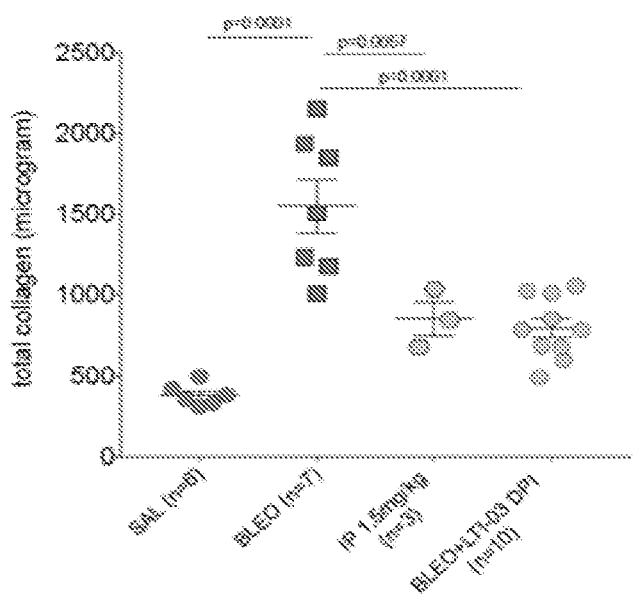
FIG. 32: Collagen Content of Murine Lung Tissue. Untreated, bleomycin treated, or bleomycin and CSP7 treated lung tissues were homogenized and collagen content was analyzed using the Quickzyme collagen assay. Graph depicts total collagen content of the lungs.

Lung tissues were homogenized and collagen content was analyzed using the Quickzyme collagen assay (FIG. 30). Bleomycin induction of fibrosis resulted in a significant increase in collagen in the lungs compared to saline treatment (P=0.0062) (FIG. 30). The Ashcroft score, a measure of lung fibrosis in mice, was lower in mice treated with CSP7 following bleomycin induction of lung fibrosis (FIG. 31).

RNA was also prepared from the homogenized lung tissues and used as described above.

TABLE 24

Thermal properties of spray dried CSP7 formulations

| Lot Number BREC-1923- | Formulation (w/w %) | Midpoint Tg (° C.) | Other Recorded Thermal Events |
|---|---|---|---|
| 001B | 100% LTI-003 | 132.4 ± 6.3 | Exo at 170° C. |
| 001C | 75/25 CSP7/Leucine | 97.4 ± 1.6 | Exo at 165° C. followed by Endo at 180° C. |
| 001D | 75/25 CSP7/Trehalose | 77.1 ± 2.2 | Exo at 130° C. followed by Endo at 170° C. |
| 001E | 75/25 CSP7/Sodium Citrate | 80.4 ± 0.4 | Exo at 150° C. followed by Endo at 170° C. |
| 001F | 75/15/10 CSP7/Leucine/Trehalose | 79.6 ± 2.3 | Exo at 100 and 150° C. followed by Endo at 155 and 170° C. |

Example 5—Formulation Suspension for Intramuscular/Subcutaneous Injection

TABLE 25

Composition of CSP7 suspension

| | |
|---|---|
| Sterile Water | — |
| CSP7 (Air-jet-milled*) | 1.2-1.4 mg/ml |
| CMC (low viscosity) | 1.5% (w/v) |
| Poloxamer 188 | 0.2% (w/v) |
| Tris | 20 mM |
| NaCl | 0.7% (w/v) |
| 1N HCl | ~285 µl to pH 7 |

*Air Jet Milled CSP7 exhibited the geometric particle size is Dv(10) = 0.75 µm; Dv(50) = 1.93 µm; Dv(90) = 4.29 µm, measured by laser diffraction.

For preparation:
1. Preparing 20 mM Tris buffer (should be pH ~10.3)
2. Dissolve 1.5% (w/w) CMC into 20 mM Tris buffer, with adding 0.2% (w/w) Poloxamer 188. Overnight stir at ~600 rpm
3. Add 0.7% (w/w) NaCl into the CMC solution
4. Adjust the solution pH to 7 by adding ~28.5 µl/ml of 1N HCl
5. Weigh and add certain amount of the air jet milled (collected from the collection bag in order to get a small particle size fractions) CSP7 powder in a clean vial
6. Use clean rod to grind the powder first, make sure there is no visibly agglomerated particles
7. Gradually add the prepared solution into the vial with milling/grinding with the rod
8. When the powder is completely wet and no visible agglomerated particles are found, q.s. to the target volume Result:

TABLE 26

Characterization of CSP7 suspension

| Actual Conc. of CSP7 | pH | Osmolarity | Chemical Potency at Day 1 | Chemical Potency at Day 8 | | |
|---|---|---|---|---|---|---|
| 1.35 mg/ml | 6.99 | 288 mOsm/kg | 101.5% | −20° C.: 99.9% | 4° C.: 101.7% | RT: 85.5% |

Example 6—Formulation Solution for Intramuscular/Subcutaneous Injection

For Preparation:
1. Preparing 20 mM Tris buffer (should be pH ~10.3)
2. Dissolve 1.5% (w/w) CMC into 20 mM Tris buffer, with adding 0.2% (w/w) Poloxamer 188. Overnight stir at ~600 rpm
3. Add 0.7% (w/w) NaCl into the CMC solution.
4. Add 1.2-1.4 mg/ml CSP7 (unprocessed powder) to the solution, vortex to dissolve. pH should be around 9, then adjust pH to 8.2-8.5 with adding ~50 µl 1N HCl

TABLE 27

Composition of CSP7 solution

| | |
|---|---|
| Sterile Water | — |
| CSP7 | 1.2-1.4 mg/ml |
| CMC (low viscosity) | 1.5% (w/v) |
| Poloxamer 188 | 0.2% (w/v) |
| Tris (called Trizma) | 20 mM |
| NaCl | 0.7% (w/v) |
| 1N HCl | ~50 µl to pH 8.2-8.5 |

Result:

TABLE 28

Characterization of CSP7 solution

| Actual Conc. of CSP7 | pH | Osmolarity | Chemical Potency at Day 0 | Chemical Potency at Day 7 | | |
|---|---|---|---|---|---|---|
| 1.18 mg/ml | 8.36 | 286 mOsm/kg | 101.5% | −20° C.: 99.6% | 4° C.: 95.6% | RT: 20.8% |

Example 7—Pre-Formulation Studies for Polypeptide Variants

Solubility study of variants was performed by adding variants powders into solvent in concentration of 5 mg/ml and then vortexing for 3 min. Observe the appearance of solutions in 5 min. Add more powder (~5 mg/ml each time) and repeat vortex and observe until precipitation or gelation occurs.

Results:

TABLE 29 pH-solubility of variants

| | Concentration (mg/ml) | | | | | | |
|---|---|---|---|---|---|---|---|
| pH | SEQ ID NO.2 | SEQ ID NO.4 | SEQ ID NO.7 | SEQ ID NO.8 | SEQ ID NO.10 | SEQ ID NO.21 | SEQ ID NO.22 |
| 4.5 | 0.15 ± 0.003$^a$ | 25.4 ± 0.8$^a$ | 32.0 ± 3.3$^b$ | 24.2 ± 3.7$^b$ | 33.9 ± 0.9$^a$ | 0.62 ± 0.04$^a$ | 57.17 ± 9.1$^a$ |
| 5.5 | 0.16 ± 0.015$^a$ | 4.0 ± 0.2$^a$ | 22.3 ± 0.1$^a$ | 23.6 ± 0.6$^a$ | 3.6 ± 0.8$^a$ | 0.14 ± 0.02$^a$ | 2.98 ± 0.1$^a$ |
| 6.5 | 0.16 ± 0.012$^a$ | 5.9 ± 0.4$^a$ | 30.5 ± 2.0$^b$ | 27.3 ± 1.2$^a$ | 5.5 ± 0.7$^a$ | 0.26 ± 0.07$^a$ | 3.49 ± 0.6$^a$ |
| 7.5 | 0.31 ± 0.013$^a$ | 16.7 ± 0.5$^a$ | 35.3 ± 0.6$^b$ | 28.3 ± 2.2$^a$ | 19.1 ± 0.1$^a$ | 0.25 ± 0.03$^a$ | 61.51 ± 1.7$^a$ |
| 8.5 | 1.43 ± 0.019$^a$ | 10.8 ± 1.1$^a$ | 23.8 ± 0.4$^b$ | 20.6 ± 2.4$^a$ | 14.6 ± 1.6$^a$ | 0.17 ± 0.04$^a$ | 29.13 ± 3.5$^a$ |

$^a$Precipitate: centrifuge solutions, then aliquot supernatant and dilute with buffer.
$^b$High viscous solution: take aliquot of solution and dilute with buffer.

TABLE 30

Appearance of solutions at pH 4.5

| SEQ ID NO | \ | \ | \ | \ | \ | Concentration (mg/ml) | \ | \ | \ | \ | \ | \ |
|---|---|---|---|---|---|---|---|---|---|---|---|---|
| | 5 | 10 | 15 | 20 | 25 | 30 | 35 | 40 | 45 | 50 | 55 | 60 |
| 4 | Clear | Clear | Clear | Clear | Clear | Translucent and colorless precipitate, viscous | — | — | — | — | — | — |
| 7 | Clear | Clear | Clear | Clear | Clear | Clear, slightly viscous | Clear Viscous | Gel | — | — | — | — |
| 8 | Clear | Clear | Clear | Clear | Gel | — | — | — | — | — | — | — |
| 10 | Clear | Clear | Clear | Clear | Clear | Translucent, colorless precipitate | Translucent and colorless precipitate, viscous | — | — | — | — | — |
| 21 | Turbid, viscous | — | — | — | — | — | — | — | — | — | — | — |
| 22 | Clear | Clear | Clear | Clear | Clear | Clear | Clear | Clear | Clear | Clear | Clear | Clear |

TABLE 31

Appearance of solutions at pH 5.5

| SEQ ID NO | Concentration (mg/ml) | | | | |
|---|---|---|---|---|---|
| | 5 | 10 | 15 | 20 | 25 |
| 4 | Turbid, viscous | — | — | — | — |
| 7 | Clear | Clear | Clear | Clear, viscous | Turbid, viscous |
| 8 | Clear | Clear, slightly viscous | Clear, slightly viscous | Translucent and colorless precipitate, viscous | Turbid, viscous |
| 10 | Turbid, viscous | — | — | — | — |
| 21 | Turbid, viscous | — | — | — | — |
| 22 | Turbid, viscous | — | — | — | — |

TABLE 32

Appearance of solutions at pH 7.5

| SEQ ID NO | 5 | 10 | 15 | 20 | 25 | 30 | 35 | 40 | 45 | 50 | 55 | 60 | 65 |
|---|---|---|---|---|---|---|---|---|---|---|---|---|---|
| 4 | Clear | Clear | Translucent and colorless precipitate, viscous | Translucent and colorless precipitate, viscous | — | — | — | — | — | — | — | — | — |
| 7 | Clear | Clear | Clear | Clear | Clear | Clear, slightly viscous | Clear, viscous | Clear, viscous | Translucent and colorless precipitate, viscous | — | — | — | — |
| 8 | Clear | Clear | Clear | Clear, slightly viscous | Clear, slightly viscous | Clear, viscous | Translucent and colorless precipitate, viscous | — | — | — | — | — | — |
| 10 | Clear | Clear | Clear | Clear | Translucent, colorless precipitate, viscous | — | — | — | — | — | — | — | — |
| 21 | Turbid, viscous | — | — | — | — | — | — | — | — | — | — | — | — |
| 22 | Clear | Clear | Clear | Clear | Clear | Clear | Clear | Clear | Clear | Clear | Clear | Clear | Turbid |

TABLE 33

Appearance of solutions at pH 8.5

| SEQ ID NO | Concentration (mg/ml) | | | | | | | |
|---|---|---|---|---|---|---|---|---|
| | 5 | 10 | 15 | 20 | 25 | 30 | 35 | 40 |
| 4 | Clear | Clear | Translucent and colorless precipitate, viscous | Translucent and colorless precipitate, viscous | — | — | — | — |
| 7 | Clear | Clear | Clear | Clear | Clear | Clear, viscous | Clear, viscous | Turbid, viscous |
| 8 | Clear | Clear | Clear | Clear | Translucent and colorless precipitate, viscous | Translucent and colorless precipitate, viscous | — | — |
| 10 | Clear | Clear | Clear | Turbid, viscous | — | — | — | — |
| 21 | Turbid viscous | — | — | — | — | — | — | — |
| 22 | Clear | Clear | Clear | Clear | Clear, viscous | Turbid, viscous | — | — |

Example 8—Pre-Formulation Study of CSP7 (Ammonium Counterion) Form

Solubility of neat (i.e., not milled) CSP7 ammonium counterion form (Table 35) was performed by adding excess amount of peptide powder into 3 mL different pH buffers (Table 36) and mixing on orbital shaker at 100 rpm for 24 hours at room temperature.

Figure 33:
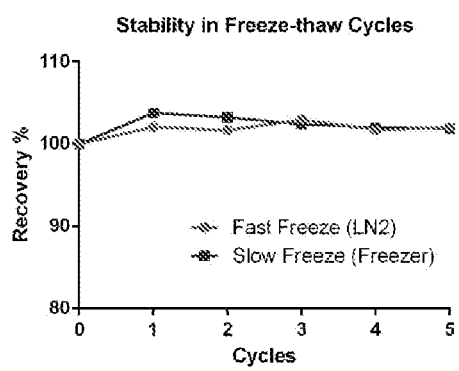
FIG. 33: Stability of CSP7 (ammonium counterion) following up to 5 freeze-thaw cycles.

For the freeze-thaw stability study (FIG. 33), 0.1 mg/mL CSP7 (ammonium counterion) peptide in phosphate buffer system (PBS, pH 7.4) was aliquoted into 15 mL/vial for fast and slow freezing, respectively. For fast and slow freezing, samples were either immersed into liquid nitrogen for at least 5 min or put into −20° C. freezer for at least 1.5 hours to ensure that the aliquot in the vial was frozen completely before then being thawed to room temperature. Each sample underwent 5 freeze-thaw cycles. Recovery % represents the percentage of each sample concentration compared to the original (untreated) concentration.

The solubility and freeze-thaw samples were filtered through a 0.45 μm membrane prior to being assayed by performing High Performance Liquid Chromatography (HPLC, Thermo Fisher Scientific, Fair Lawn, N.J.). Briefly, samples were analyzed using Dionex 3000 HPLC system equipped with a Waters® reversed phase C18 column 2.5 μm, 150 mm×4.60 mm. The HPLC column was heated to 60° C. for testing, and the peptide was detected at a wavelength of 215 nm and a 1 mL/min flow rate. The two mobile phases were A (0.1% acetic acid in water) and B (0.1% acetic acid in acetonitrile). The injection volume was 20 μL and the standard curve was plotted from 0.01-1 mg/ml.

TABLE 34

HPLC method details.

| Separation Column | XSelect CSH C18, 4.6 × 150 mm 2.5 um |
|---|---|
| Mobil Phase A | 0.1% Acetic acid in H2O |
| Mobil Phase B | 0.1% Acetic acid in ACN |
| Injection Volume | 20 μL |
| Run Time | 48 min |
| Column Temp. | 60° C. |
| Flow | 1.0 mL/min |
| Wavelength | 215 nm |

| Gradient | Time (min) | A % | B % |
|---|---|---|---|
| | 0 | 90 | 10 |
| | 30 | 75 | 25 |
| | 30.1 | 20 | 80 |
| | 39 | 20 | 80 |
| | 39.1 | 90 | 10 |
| | 48 | 90 | 10 |

TABLE 35 pH-solubility profile of CSP7 (ammonium counterion).

| pH | Conc. (mg/mL) |
|---|---|
| 3 | 0.17 |
| 4 | 0.07 |
| 5 | 0.05 |
| 6 | 0.07 |
| 7 | 0.10 |
| 8 | 0.38 |
| 9 | 2.30 |
| 10 | 7.87 |
| 11 | 14.43 |

TABLE 36

Buffer system and amount of CSP7 peptide added in 3 mL buffers at each pH

| pH | Buffer System | Add ~X mg to 3 ml |
|---|---|---|
| 3 | 100 mM Citrate | 2 mg |
| 4 | 100 mM Acetate | 2 mg |
| 5 | 100 mM Acetate | 1 mg |
| 6 | 20 mM Citrate | 1 mg |
| 7 | 30 mM Phosphate | 2 mg |
| 8 | 100 mM Tris | 4 mg |
| 9 | 100 mM Tris | 12 mg |
| 10 | 25 mM Carbonate | 30 mg |
| 11 | 25 mM Carbonate | 40 mg |

Example 9. Characterization and Stability Study of Milled CSP7 (Ammonium Counterion) Powder as Lot #UTA181028

A Model 00 Jet-O-Mizer™ (also known as Aljet mill, Fluid Energy, Telford, Pa.) was used to mill the CSP7 peptide. The feed rate, pushing pressure, and grinding pressure are 1 g/min, 60 psi, and 70 psi, respectively (Table 37). The batch size is 20 g, and the milled powder is collected from different sections of the jet mill, including: the tube after grinding chamber (bfC), the cyclone (C), the collection vessel adapter (D), the collection bag adapter (E), the collection bag (H), and the collection vessel (G). The collected powder was blended for 10 min using a Turbula mixer (Glen Mills Inc., Clifton, N.J., USA).

TABLE 37

Parameters for milling CSP7 (ammonium counterion) powder.

| Parameter | Value |
|---|---|
| Feeding Rate | 1 g/min |
| Pushing Pressure | 60 psi |
| Grinding Pressure | 70 psi |

Figure 34:
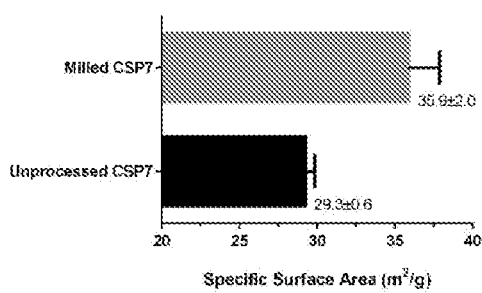
FIG. 34: Specific surface area of milled and neat CSP7 (ammonium counterion) powder.

Specific surface area of milled and CSP7 ammonium counterion neat powder. Specific surface areas of milled and unprocessed CSP7 powder are analyzed using Monosorb Rapid Surface Area Analyzer Model MS-21 (Quantachrome Instruments, Boynton Beach, Fla.) with single point BET method (FIG. 34). Samples are outgassed at 25° C. with nitrogen gas at 20 psi for 20-24 hours to remove water and other impurity molecules on the surface. A mixture of nitrogen/helium (50:50 v/v) is used as the adsorbate, and the equipment is calibrated with nitrogen before the test.

Figure 5:
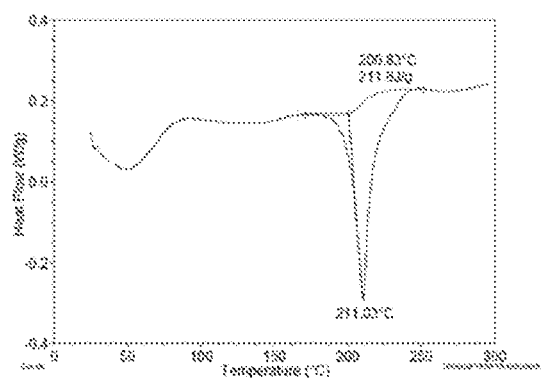
FIG. 5: Differential Scanning calorimetry of CSP7 Bulk Powder. Bulk CSP7 powder was analyzed by differential scanning calorimetry using TA instrument Q20 Differential Scanning calorimetry. Pictured is a curve from modulated-DSC with a frequency of 1° C./60 s and a rate of 2° C./min, ramping from 25 to 300° C.
Figure 6:
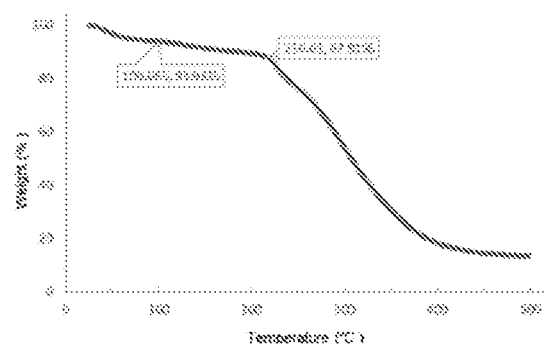
FIG. 6: Thermogravimetric Analysis of CSP7 Bulk Powder. Thermogravimetric analysis was performed using a Mettler Thermogravimetric Analyzer, Model TGA/DSC. Pictured is the TGA curve. The heating rate was set to 10° C./min, ramping from 25 to 500° C.
Figure 7:
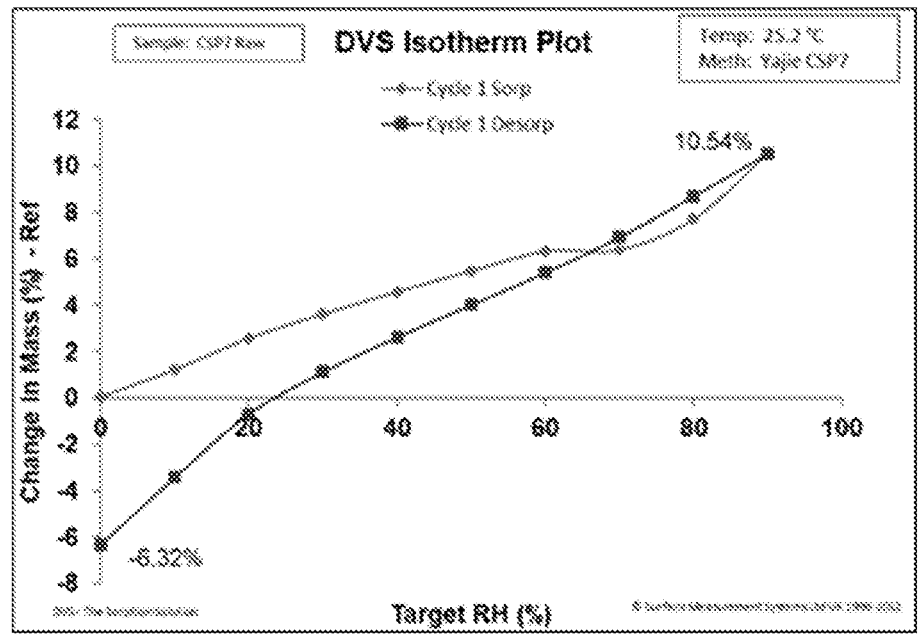
FIG. 7: Dynamic Vapor Sorption of CSP7 Bulk Powder. Bulk CSP7 powder was run on a Surface Measurement Systems DVS instrument for a full sorption/desorption cycle from 0% to 90% relative humidity in steps of 10% at 25° C. Moisture desorption at 0% humidity and mass change at 90% humidity are indicated.
Figure 35:
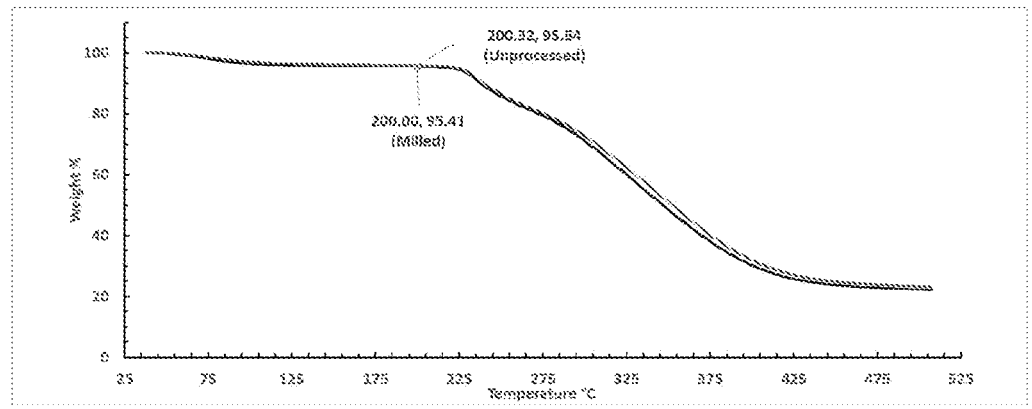
FIG. 35: Thermogravimetric Analysis of milled and neat CSP7 (ammonium counterion) powder.

Thermogravimetric Analysis of milled and CSP7 ammonium counterion neat powder. Using the method described in Example 2 for FIG. 5, except that the starting temperature was 35° C. instead of 25° C. The results are shown in FIG. 35.

Figure 36:
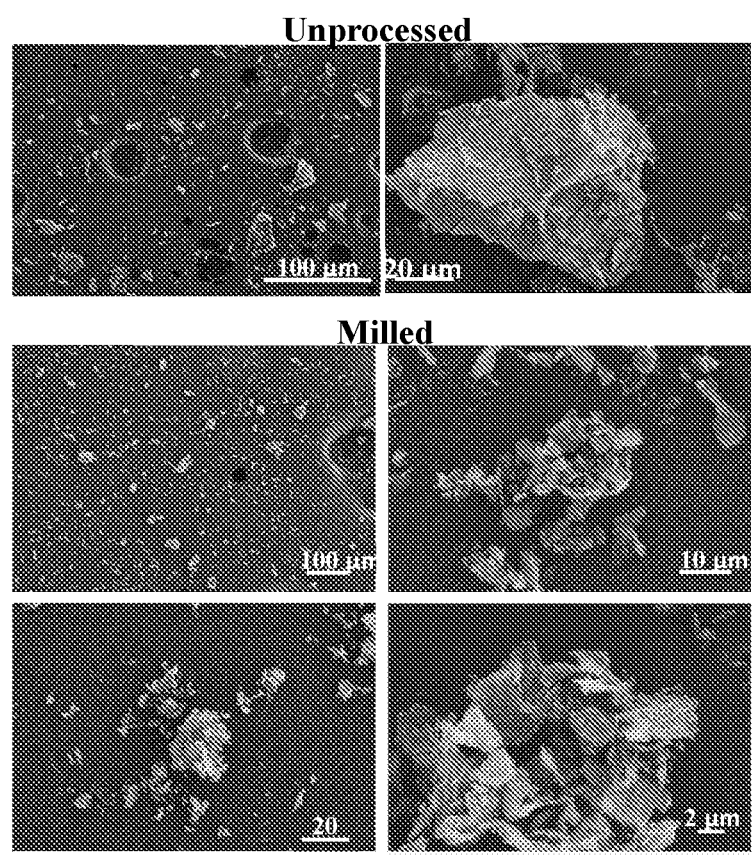
FIG. 36: SEM images of milled and neat CSP7 (ammonium counterion) powder.
Figure 37:
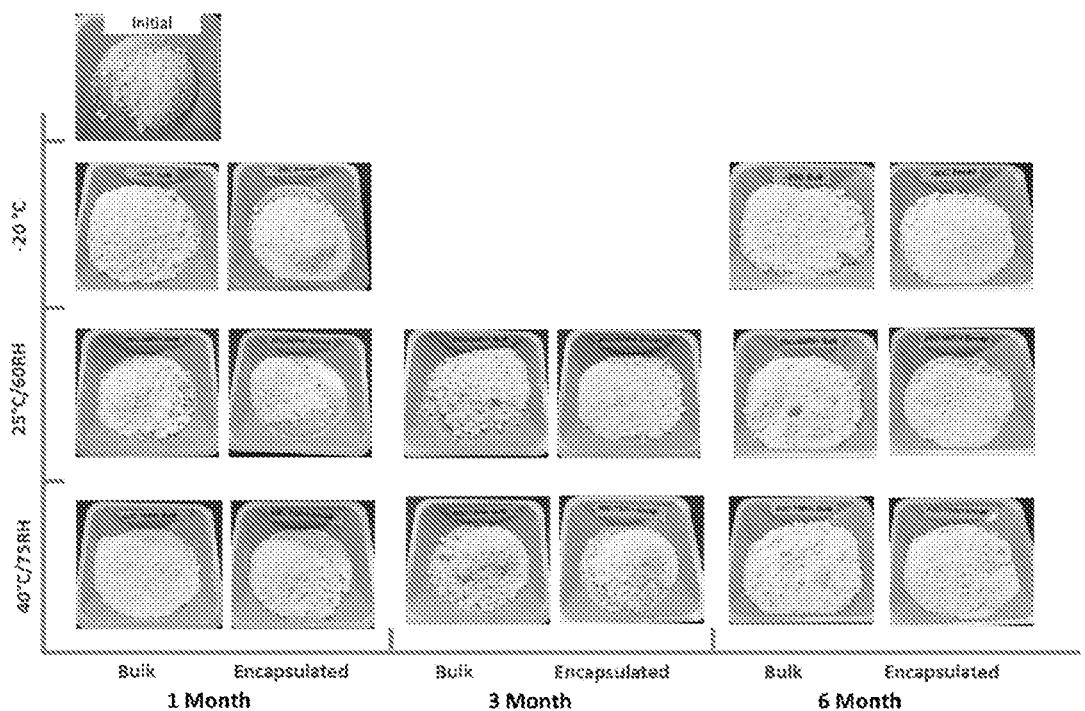
FIG. 37: Appearance of milled CSP7 (ammonium counterion) powder in stability study.

Scanning Electron Microscopy (SEM) Images of milled and neat CSP7 (ammonium counterion) powder. The morphology of CSP7 (FIG. 36) is analyzed with Zeiss Supra 40VP SEM (Carl Zeiss Microscopy GmbH, Jena, Germany). Samples are mounted on aluminum SEM stubs by a carbon conductive tape and coated with 12 nm of platinum/palladium (Pt/Pd) using a Cressington sputter coater 208 HR (Cressington Scientific Instruments Ltd., Watford, UK). Images are taken for neat (i.e., unprocessed) and post-milled CSP7 samples.

Stability study for milled CSP7 (ammonium counterion) from Lot #UTA181028. The stability of milled CSP7 powder was investigated under different storage conditions for a period of up to 6 months. Milled CSP7 peptide is packaged as two forms, bulk milled powder and encapsulated milled powder. For storage as bulk milled powder, 0.21-0.24 g peptide is filled in 20 mL scintillation vials (Kimble®, DWK Life Sciences, Millville, N.J., US) and stored within a heat-sealed foil pouch (Impak Corp, Los Angeles, Calif., US) containing two bags of 1 g silica gel desiccant (Tyvek®, Sorbco Packaging LLC, Belen, N. Mex., US) in each pouch. Milled peptide powder is also encapsulated in size 3 HPMC capsules (Capsugel, Morristown, N.J., US) in a weight of about 11±5% mg, and 22-26 capsules are then packaged in HDPE bottles (Drug Plastic, Boyertown, Pa., US), followed by sealing the HDPE bottle within a foil pouch (without desiccant). Packages are stored in stability chambers at the following storage conditions: −20° C., 25° C./60% RH, and 40° C./75% RH. Samples are removed for testing at 1, 3, and 6 months (Table 38). For tests except the aerodynamic particle size distribution, encapsulated powder was removed from the capsule and mixed in a glass vial by rotating the vial.

TABLE 38

Tests schedule for stability study.

| | Time (Months) | | | |
|---|---|---|---|---|
| Condition | Initial | 1 | 3 | 6 |
| −20° C. | 1-6 | 1-5 | Not Tested | 1-5 |
| 25° C./60% RH | | | 1-5 | |
| 40° C./75% RH | | | 1-7 | 1-6 |

| Test# | Test | Tentative Specification | Method |
|---|---|---|---|
| 1 | Appearance | Color and appearance (agglomerate) | Visual |
| 2 | Assay | % of mass balance | HPLC |
| 3 | Water Content | % water in sample | KF-C |
| 4 | GPSD | Dv 10, 50, 90; 1-5 µm % | LD |
| 5 | APSD | MMAD, GSD, EF %, FPD, FPF % | NGI |
| 6 | Crystallinity | Graph and % crystallinity | XRPD |

* Acronyms:
HPLC: High Performance Liquid Chromatography;
KF-C: Karl Fischer Coulometric;
GPSD: Geometric Particle Size Distribution;
LD: Laser Diffraction;
APSD: Aerodynamic Particle Size Distribution;
NGI: Next Generation Impactor;
SEM: Scanning Electron Microscope;
XRPD: X-ray Powder Diffraction.

Appearance of the milled powder. The appearance of the milled powder was recorded by taking pictures with regular camera (FIG. 30).

Chemical stability of the milled peptide. The powders were assayed using HPLC method described in Example 8. Results are shown below in Table 39. Percentage represents the assay amount compared to the mass balance. Assay was adjusted for water content.

TABLE 39

Assay of milled CSP7 ammonium counterion by HPLC in stability study.

| | Time Point | | | | | |
|---|---|---|---|---|---|---|
| | −20° C. | | 25° C./60 RH Initial 98.85% | | 40° C./75 RH | |
| | Bulk | Encapsulated | Bulk | Encapsulated | Bulk | Encapsulated |
| 1 Month | 98.9 ± 1.2 | 99.8 ± 1.2 | 98.8 ± 1.3 | 100.5 ± 1.4 | 100.1 ± 1.3 | 100.9 ± 1.3 |
| 3 Month | — | | 101.3 ± 0.4 | 100.0 ± 0.2 | 102.1 ± 0.2 | 96.9 ± 0.4 |
| 6 Month | 100.9 ± 0.3 | 101.5 ± 0.2 | 100.9 ± 0.2 | 101.7 ± 0.3 | 101.9 ± 0.1 | 100.2 ± 0.6 |

Moisture content of CSP powder. Coulometric Karl Fischer (Mettler Toledo C20 Leicester, Ohio, US) is used to determine the moisture content in the peptide powders (Table 40). The reliability of the equipment is tested with a Karl Fischer water content standard (Hydranal™ water standard, Honeywell, Charlotte, N.C., US). A known amount of powder is suspended in anhydrate methanol (Sigma, St. Louis, Mo.) and the suspension is injected to the anolyte solution (Hydranal™-Coulomat AG, H Honeywell, Charlotte, N.C., US) to trigger the titration in the presence of the catholyte solution (Hydranal™-Coulomat CG, H Honeywell, Charlotte, N.C., US). The result is recorded as the difference of water content in sample subtracting the blank anhydrous methanol solution.

TABLE 40

Moisture content in stability study powder samples.

| | Time Point | | | | | |
|---|---|---|---|---|---|---|
| | −20° C. | | 25° C./60 RH Initial 4.18 ± 0.05% | | 40° C./75 RH | |
| | Bulk | Encap. | Bulk | Encap. | Bulk | Encap. |
| 1 Month | 4.31 ± 0.29% | 4.94 ± 0.15% | 3.66 ± 0.33% | 4.43% | 3.91 ± 0.03% | 4.73 ± 0.08% |
| 3 Month | — | | 4.56 ± 0.31% | 5.51 ± 0.37% | 4.54 ± 0.08% | 5.86 ± 0.14% |
| 6 Month | 4.68 ± 0.08 | 5.61 ± 0.27 | 4.42 ± 0.32 | 5.76 ± 0.06 | 4.71 ± 0.21 | 6.20 0.18 |

Geometric particle size distribution. GPSD of CSP7 powder was analyzed before and after milling using a Sympatec HELOS laser diffraction instrument (Sympatec GmbH, Germany) equipped with RODOS dispersion. Measurements are taken every 10 ms following powder dispersion at 3 bar. Measurements that are between 5 and 25% optical density were averaged to determine particle size distribution. The particle sizes by volume are reported at percentiles of 10, 50, and 90 (e.g., Dv 10, Dv 50, and Dv 90), respectively, as well as the percentages of particles falling into 1-5 μm size range. The results are shown in 41.

TABLE 41

Geometric particle size distribution of milled CSP7 (ammonium counterion) in the stability study

| | Lot#UTA181028 | | Dv 10 (μm) | Dv 50 (μm) | Dv 90 (μm) | % 1-5 μm |
|---|---|---|---|---|---|---|
| | Unprocessed | | 1.2 ± 0 | 4.5 ± 0.1 | 15.7 ± 0.8 | 47.0 ± 0.9 |
| | Initial | | 0.8 ± 0 | 2.2 ± 0 | 4.6 ± 0 | 77.9 ± 0.3 |
| 1 Month | Bulk | −20° C. | 0.8 ± 0 | 2.2 ± 0 | 4.9 ± 0.1 | 74.9 ± 0.7 |
| | | 25° C./60 RH | 0.8 ± 0 | 2.1 ± 0 | 4.8 ± 0 | 74.3 ± 0.3 |
| | | 40° C./75 RH | 0.8 ± 0 | 2.1 ± 0 | 4.8 ± 0 | 74.6 ± 0 |
| | Encapsulated | −20° C. | 0.8 ± 0 | 2.1 ± 0 | 4.8 ± 0.1 | 74.1 ± 0.1 |
| | | 25° C./60 RH | 0.8 ± 0 | 2.1 ± 0.1 | 4.7 ± 0.1 | 73.6 ± 0.8 |
| | | 40° C./75 RH | 0.8 ± 0 | 2 ± 0 | 4.7 ± 0.1 | 72.8 ± 0.4 |
| 3 Month | Bulk | 25° C./60 RH | 0.8 ± 0 | 2.1 ± 0.1 | 4.7 ± 0.1 | 73.7 ± 0.3 |
| | | 40° C./75 RH | 0.8 ± 0 | 2.2 ± 0 | 4.8 ± 0 | 75 ± 0.5 |
| | Encapsulated | 25° C./60 RH | 0.8 ± 0 | 2.1 ± 0 | 4.7 ± 0 | 73.6 ± 0.4 |
| | | 40° C./75 RH | 0.8 ± 0 | 2.1 ± 0 | 4.7 ± 0 | 73.9 ± 0.1 |
| 6 Month | Bulk | −20° C. | 0.8 ± 0 | 2.2 ± 0.1 | 4.9 ± 0.1 | 73.8 ± 0.5 |
| | | 25° C./60 RH | 0.8 ± 0 | 2.2 ± 0 | 4.9 ± 0 | 74 ± 0.4 |
| | | 40° C./75 RH | 0.8 ± 0 | 2.1 ± 0 | 4.8 ± 0.1 | 73.6 ± 0.6 |
| | Encapsulated | −20° C. | 0.8 ± 0 | 2.2 ± 0 | 4.9 ± 0 | 74.4 ± 0.1 |
| | | 25° C./60 RH | 0.8 ± 0 | 2.1 ± 0 | 4.8 ± 0 | 73.9 ± 0.3 |
| | | 40° C./75 RH | 0.8 ± 0 | 2.1 ± 0 | 4.9 ± 0 | 73.8 ± 0.3 |

Aerodynamic particle size distribution: The aerodynamic particle size distribution was evaluated by performing NGI as described in Example 1, except that the powder weight in the tested capsule was 11±5% mg and pre-separator was removed in the assembly of the NGI in stability study. The results are given in Table 42.

TABLE 42

Aerodynamic particle size distribution of milled CSP7 (ammonium counterion) in the stability study.

| Lot#UTA181028 | | | FPD (mg) | FPF % | EF % | MMAD (μm) | GSD |
|---|---|---|---|---|---|---|---|
| | Unprocessed | | 4.2 ± 0.3 | 48.4 ± 3.1 | 92.8 ± 1.4 | 3.09 ± 0.07 | 4.67 ± 0.09 |
| | Initiate | | 8.3 ± 0.5 | 93.3 ± 3.3 | 83.5 ± 0.1 | 1.58 ± 0.10 | 1.91 ± 0.03 |
| 1 Month | Bulk | −20° C. | 8.0 ± 0.4 | 88.8 ± 2.9 | 84 ± 1.4 | 1.86 ± 0.16 | 1.86 ± 0.02 |
| | | 25° C./60 RH | 7.7 ± 0.5 | 92.2 ± 1.0 | 80.7 ± 1.8 | 1.69 ± 0.09 | 1.86 ± 0.01 |
| | | 40° C./75 RH | 8.0 ± 0.3 | 91.8 ± 0.6 | 85.2 ± 1.4 | 1.79 ± 0.08 | 1.86 ± 0.02 |
| | Encapsulation | −20° C. | 7.3 ± 0.1 | 87.8 ± 0.3 | 83.6 ± 1.3 | 1.85 ± 0.03 | 1.91 ± 0.01 |
| | | 25° C./60 RH | 7.6 ± 0.3 | 90.0 ± 1.4 | 81.6 ± 4 | 1.74 ± 0.08 | 1.90 ± 0.02 |
| | | 40° C./75 RH | 7.9 ± 0.3 | 89.6 ± 1.3 | 84.7 ± 1 | 1.80 ± 0.15 | 1.90 ± 0.02 |
| 3 Month | Bulk | 25° C./60 RH | 7.5 ± 0.5 | 92.2 ± 2.1 | 79.8 ± 0.3 | 1.55 ± 0.09 | 1.84 ± 0.06 |
| | | 40° C./75 RH | 7.7 ± 0.3 | 90.4 ± 1.6 | 82.9 ± 0.8 | 1.66 ± 0.18 | 1.91 ± 0.05 |
| | Encapsulation | 25° C./60 RH | 7.6 ± 0.3 | 89.4 ± 0.8 | 80.5 ± 1.9 | 1.76 ± 0.05 | 1.85 ± 0.01 |
| | | 40° C./75 RH | 7.4 ± 0.3 | 87.6 ± 0.6 | 83.4 ± 2.5 | 1.83 ± 0.06 | 1.92 ± 0.03 |
| 6 Month | Bulk | −20° C. | 7.2 ± 0.1 | 87.1 ± 1.5 | 79.1 ± 1.6 | 1.79 ± 0.10 | 1.90 ± 0.01 |
| | | 25° C./60 RH | 7.2 ± 0.2 | 87.1 ± 1.8 | 80.4 ± 2.1 | 1.85 ± 0.08 | 1.86 ± 0.01 |
| | | 40° C./75 RH | 7.3 ± 0.1 | 86.2 ± 0.8 | 81.9 ± 1.2 | 1.86 ± 0.01 | 1.92 ± 0.06 |
| | Encapsulation | −20° C. | 7.3 ± 0.1 | 85.3 ± 1.8 | 80.9 ± 1.3 | 1.90 ± 0.13 | 1.95 ± 0.06 |
| | | 25° C./60 RH | 7.4 ± 0.4 | 87.9 ± 0.5 | 80.0 ± 0.4 | 1.77 ± 0.02 | 1.90 ± 0.02 |
| | | 40° C./75 RH | 7.4 ± 0.0 | 85.6 ± 2.7 | 80.7 ± 1.1 | 1.81 ± 0.11 | 1.94 ± 0.03 |

Figure 38:
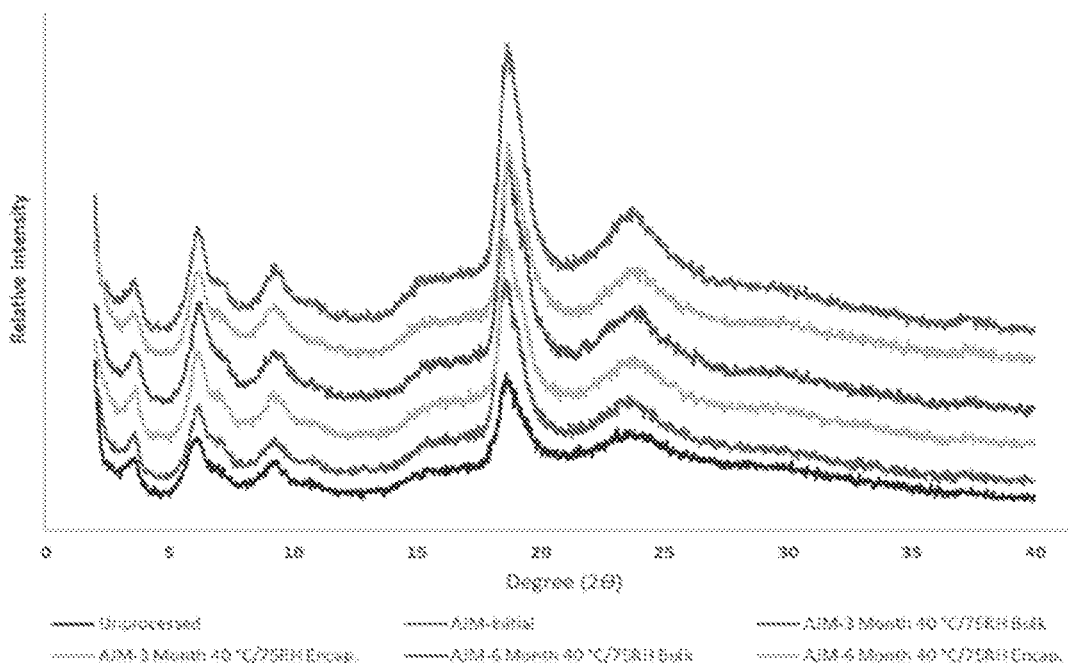
FIG. 38: Crystallinity of milled CSP7 (ammonium counterion) in the stability study.

Crystallinity of the CSP7 powders. Crystallinity of powders was evaluated by method described in Example 2 for FIG. 2, and the results are shown in FIG. 38.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Carvalho et al., "Influence of particle size on regional lung deposition—What evidence is there?" *Int. J. Pharma.* 406:1-10, 2011.

Hübner, R.-H.; Gitter, W.; El Mokhtari, N. E.; Mathiak, M.; Both, M.; Bolte, H.; Freitag-Wolf, S.; Bewig, B. Standardized quantification of pulmonary fibrosis in histological samples. *Biotechniques,* 44, 507-11, 514-7, 2008.

Surasarang et al., "Optimization of Formulation for a Novel Inhaled Candidate Therapeutic for Idiopathic Fibrosis," *Drug Development and Industrial Pharmacy,* 44(2):184-198, 2017.

Tepper, J. S.; Kuehl, P. J.; Cracknell, S.; Nikula, K. J.; Pei, L.; Blanchard, J. D. Symposium Summary: "breathe In, Breathe Out, Its Easy: What You Need to Know about Developing Inhaled Drugs." *Int. J. Toxicol.* 35, 376-392, 2016.

What is claimed is:

1. A dry powder composition comprising particles, wherein the particles comprise a peptide consisting of FTTFTVT (SEQ ID NO: 2) or a pharmaceutically acceptable salt thereof, wherein the particles have a median particle diameter of less than 5 μm, wherein the dry powder composition does not comprise a pharmaceutically acceptable carrier or excipient; and wherein the dry powder composition is formulated for use in a dry powder inhaler.

2. The dry powder composition of claim 1, wherein the dry powder composition is encapsulated.

3. The dry powder composition of claim 1, wherein the dry powder composition is encased in a shell capsule.

4. The dry powder composition of claim 1, wherein the pharmaceutically acceptable salt is an ammonium salt.

5. The dry powder composition of claim 1, wherein the pharmaceutically acceptable salt is an acetate salt.

6. The dry powder composition of claim 1, wherein the particles are amorphous.

7. The dry powder composition of claim 1, wherein the particles have a median particle diameter between about 1 μm to about 5 μm.

8. The dry powder composition of claim 1, wherein the particles have a median particle diameter of about 2 μm, about 2.5 μm, or about 3 μm.

9. The dry powder composition of claim 1, wherein the dry powder composition is stable for at least 1 month, at least 3 months, or at least 6 months.

10. The dry powder composition of claim 1, wherein the dry powder composition is stable for at least 6 months.

11. The dry powder composition of claim 1, wherein the dry powder is produced by a milling process.

12. The dry powder composition of claim 11, wherein the dry powder is produced by air jet milling.

13. The dry powder composition of claim 11, wherein the dry powder is produced by ball milling, wet milling, or cryogenic milling.

14. The dry powder composition of claim 1, wherein the dry powder is produced by a spray-drying process.

15. A dry powder inhaler comprising the dry powder composition of claim 1.

16. The dry powder composition of claim 1, wherein at least 70% of the particles have a particle size of about 1 μm to about 5 μm.

17. The dry powder composition of claim 1, wherein 75%-95% of the particles have a particle size less than 5 μm.

18. The dry powder composition of claim 1, wherein the median particle diameter of the particles is a mass median aerodynamic diameter (MMAD).

* * * * *